(12) United States Patent
Matsumura et al.

(10) Patent No.: US 11,622,694 B2
(45) Date of Patent: Apr. 11, 2023

(54) PULSE WAVE MEASUREMENT DEVICE, PULSE WAVE MEASUREMENT METHOD, AND BLOOD PRESSURE MEASUREMENT DEVICE

(71) Applicants: OMRON CORPORATION, Kyoto (JP); OMRON HEALTHCARE CO., LTD., Muko (JP)

(72) Inventors: Naomi Matsumura, Kyoto (JP); Kentaro Mori, Kyoto (JP); Naoki Matsumoto, Kyoto (JP); Yasuhiro Kawabata, Kyoto (JP); Kenji Fujii, Kyoto (JP)

(73) Assignees: OMRON CORPORATION, Kyoto (JP); OMRON HEALTHCARE CO., LTD., Muko (JP)

( * ) Notice: Subject to any disclaimer, the term of this patent is extended or adjusted under 35 U.S.C. 154(b) by 360 days.

(21) Appl. No.: 16/454,254

(22) Filed: Jun. 27, 2019

(65) Prior Publication Data
US 2019/0313924 A1    Oct. 17, 2019

Related U.S. Application Data

(63) Continuation of application No. PCT/JP2017/040323, filed on Nov. 8, 2017.

(30) Foreign Application Priority Data

Dec. 28, 2016    (JP) .............................. JP2016-256024

(51) Int. Cl.
*A61B 5/021*    (2006.01)
*A61B 5/0225*    (2006.01)
(Continued)

(52) U.S. Cl.
CPC ........ *A61B 5/02116* (2013.01); *A61B 5/0225* (2013.01); *A61B 5/02125* (2013.01); *A61B 5/681* (2013.01)

(58) Field of Classification Search
CPC ............ A61B 5/02116; A61B 5/02125; A61B 5/0225; A61B 5/681; A61B 5/02225
See application file for complete search history.

(56) References Cited

U.S. PATENT DOCUMENTS 7,780,605 B2 *    8/2010    Yamashita ......... A61B 5/02141
                                                                    600/490
9,072,436 B2 *    7/2015    Kobayashi ............. A61B 5/021
(Continued)

FOREIGN PATENT DOCUMENTS

CN    103222860 A    7/2013
CN    106028917 A    10/2016
(Continued)

OTHER PUBLICATIONS

Jan. 9, 2018 International Search Report issued in Patent Application No. PCT/JP2017/040323.
(Continued)

*Primary Examiner* — Nathan J Jenness
*Assistant Examiner* — Justin Xu
(74) *Attorney, Agent, or Firm* — Oliff PLC

(57) ABSTRACT

A pulse wave measurement device including: a belt to be worn around a measurement target site; first and second pulse wave sensors that are mounted on the belt spaced from each other with respect to a width direction of the belt, and that detect pulse waves of opposing portions of an artery passing through the measurement target site; a pressing unit that is mounted on the belt is capable of changing pressing forces of the pulse wave sensors against the measurement target site; a waveform comparing unit that acquires pulse
(Continued)

wave signals which are time-sequentially output by the pulse wave sensors respectively, and compares waveforms of the pulse wave signals; and a pulse wave sensor pressing force setting unit that variably sets the pressing forces by the pressing unit such that the waveforms of the pulse wave signals compared by the waveform comparing unit become identical to each other.

11 Claims, 36 Drawing Sheets

(51) Int. Cl.
*A61B 5/00* (2006.01)
*A61B 5/022* (2006.01)

(56) References Cited

U.S. PATENT DOCUMENTS

| | | | | |
|---|---|---|---|---|
| 2002/0147401 A1* | 10/2002 | Oka | ............ | A61B 5/02125 600/490 |
| 2005/0015015 A1* | 1/2005 | Mizukoshi | ......... | A61B 5/02233 600/499 |
| 2010/0076328 A1* | 3/2010 | Matsumura | ............ | A61B 5/021 600/500 |
| 2010/0268092 A1* | 10/2010 | Kobayashi | ........... | A61B 5/0285 600/483 |
| 2012/0253209 A1 | 10/2012 | Ukawa et al. | | |
| 2015/0025399 A1* | 1/2015 | Nishibayashi | ..... | A61B 5/02141 600/492 |
| 2017/0340209 A1* | 11/2017 | Klaassen | ................ | A61B 5/021 |

FOREIGN PATENT DOCUMENTS

| | | | |
|---|---|---|---|
| JP | H2-213324 A | 8/1990 | |
| JP | H2-305547 A | 12/1990 | |
| JP | H10-328151 A | 12/1998 | |
| JP | 2007-44363 A | 2/2007 | |
| JP | 2013-236836 A | 11/2013 | |
| WO | 2014155750 A1 | 10/2014 | |
| WO | WO-2016040253 A1 * | 3/2016 | ............. A61B 5/021 |
| WO | WO-2016097271 A2 * | 6/2016 | ............ A61B 5/6824 |

OTHER PUBLICATIONS

Jun. 2, 2020 Office Action issued in Japanese Patent Application No. 2016-256024.

May 26, 2021 Office Action issued in Chinese Patent Application No. 201780081210.X.

* cited by examiner

FIG.36

$$r = \frac{\sum_{i=1}^{n}(x_i - \bar{x})(y_i - \bar{y})}{\{(\sum_{i=1}^{n}(x_i - \bar{x})^2)(\sum_{i=1}^{n}(y_i - \bar{y})^2)\}^{1/2}} \qquad \cdots (\text{Eq.1})$$

FIG.37

$$EBP = \frac{\alpha}{DT^2} + \beta \qquad \cdots (\text{Eq.2})$$

FIG.38

$$EBP = \frac{\alpha}{DT^2} + \frac{\beta}{DT} + \gamma DT + \delta \qquad \cdots (\text{Eq.3})$$

FIG.39

$$EBP = \frac{\alpha}{DT} + \beta RR + \gamma VR + \delta \qquad \cdots (\text{Eq.4})$$

PULSE WAVE MEASUREMENT DEVICE, PULSE WAVE MEASUREMENT METHOD, AND BLOOD PRESSURE MEASUREMENT DEVICE

CROSS-REFERENCE TO RELATED APPLICATION

This is a continuation application of International Application No. PCT/JP2017/040323, with an International filing date of Nov. 8, 2017, which claims priority of Japanese Patent Application No. 2016-256024 filed on Dec. 28, 2016, the entire content of which is hereby incorporated by reference.

TECHNICAL FIELD

The present invention relates to a pulse wave measurement device and a pulse wave measurement method, and more particularly, to a pulse wave measurement device and a pulse wave measurement method that non-invasively measure the transit time of a pulse wave transiting through an artery (Pulse Transit Time; PTT).

The present invention also relates to a blood pressure measurement device that includes such a pulse wave measurement device and calculates blood pressure by using a correspondence equation between the pulse transit time and the blood pressure.

BACKGROUND ART

For example, as disclosed in Patent Literature 1 (Japanese Patent Laid-Open No. 2-213324), there has been conventionally known a technique in which a small cuff 13 and a middle cuff 12 are fixedly arranged in a cuff 10 while the small cuff 13 and the middle cuff 12 are apart from each other in a width direction of the cuff 10 (corresponding to a longitudinal direction of an upper arm), and a time difference (pulse transit time) between pulse wave signals detected by the small cuff 13 and the middle cuff 12 is measured. A large cuff 11 for measuring blood pressure by an oscillometric method is placed along the space between the small cuff 13 and the middle cuff 12 in the cuff 10.

SUMMARY OF THE INVENTION

In Patent Literature 1, measurement of the pulse transit time is performed while an operation of applying pressure and reducing pressure is executed so that the pressure in the small cuff 13 and the pressure in the middle cuff 12 are equal to the pressure in the large cuff 11. However, since the arrangement of tissues in an arm is different among users (subjects), proper values of the pressure in the middle cuff 12 located upstream side of the brachial artery (on a side closer to the heart) and the pressure in the small cuff 13 located downstream side of the brachial artery (on a side farther from the heart) are different among the users (subjects). Accordingly, when the pressure in the middle cuff 12 and the pressure in the small cuff 13 are maintained at the same pressure as disclosed in Patent Literature 1, appropriate measurement conditions are not acquired in some cases. For this reason, there is a problem that measurement accuracy of the pulse transit time is not good.

For example, there is assumed an aspect in which two pulse wave sensors are mounted on a wrist wearing belt (or cuff) of a wearable device while being apart from each other in the width direction of the belt (corresponding to the longitudinal direction of the wrist), and the time difference (pulse transit time) between the pulse wave signals detected by the two pulse wave sensors respectively is measured. In this aspect, the width of the belt is limited to mitigate discomfort of wearing, and thus the distance between the two pulse wave sensors is limited to be relatively short.

Therefore, it is particularly required to enhance the measurement accuracy of the pulse transit time, and the pressing force of the pulse wave sensor located upstream side of the artery and the pressing force of the pulse wave sensor located downstream side of the artery are required to be appropriately set.

Therefore, an object of the present invention is to provide a pulse wave measurement device and a pulse wave measurement method that can enhance the measurement accuracy of a pulse transit time.

Another object of the present invention is to provide a blood pressure measurement device that includes such a pulse wave measurement device and calculates blood pressure by using a correspondence equation between the pulse transit time and the blood pressure.

In order to achieve the foregoing objects, a pulse wave measurement device according to the present disclosure includes:

a belt to be worn so as to be wound around a measurement target site;

first and second pulse wave sensors that are mounted on the belt to be spaced from each other with respect to a width direction of the belt, and that detect pulse waves of opposing portions of an artery passing through the measurement target site;

a pressing unit that is mounted on the belt and is capable of changing pressing forces of the first and second pulse wave sensors against the measurement target site to press the measurement target site;

a waveform comparing unit that acquires first and second pulse wave signals which are time-sequentially output by the first and second pulse wave sensors respectively, and compares waveforms of the first and second pulse wave signals; and a pulse wave sensor pressing force setting unit that variably sets the pressing forces by the pressing unit such that the waveforms of the first and second pulse wave signals compared by the waveform comparing unit become identical to each other.

In the present specification, the "measurement target site" indicates a site through which an artery passes. The measurement target site may be, for example, an upper limb such as a wrist or an upper arm, or a lower limb such as an ankle or a thigh. Furthermore, in the present specification, "with respect to" the width direction of the belt indicates a positional relationship in the width direction of the belt.

Furthermore, "belt" indicates a belt-like member which is mounted to be wound around the measurement target site regardless of the name. For example, in place of the belt, the name such as "band" or "cuff" is possible.

The "width direction" of the belt corresponds to the longitudinal direction of the measurement target site.

BRIEF DESCRIPTION OF DRAWINGS

The present invention will become more fully understood from the detailed description given hereinbelow and the accompanying drawings which are given by way of illustration only, and thus are not limitative of the present invention, and wherein:

FIG. 36 is a diagram showing an equation representing a cross-correlation coefficient r between a data string $\{x_i\}$ and a data string $\{y_i\}$.

FIG. 37 is a diagram showing an example of a predetermined correspondence equation between the pulse transit time and the blood pressure.

FIG. 38 is a diagram showing another example of the predetermined correspondence equation between the pulse transit time and the blood pressure.

FIG. 39 is a diagram showing still another example of the predetermined correspondence equation between the pulse transit time and the blood pressure.

DESCRIPTION OF EMBODIMENT

Hereinafter, embodiments of the present invention will be described in detail with reference to the drawings.

First Embodiment

First, a first embodiment according to a blood pressure measurement device including a pulse wave measurement device of the present invention will be described in detail with reference to the drawings.

(Configuration of Sphygmomanometer)

Figure 1:
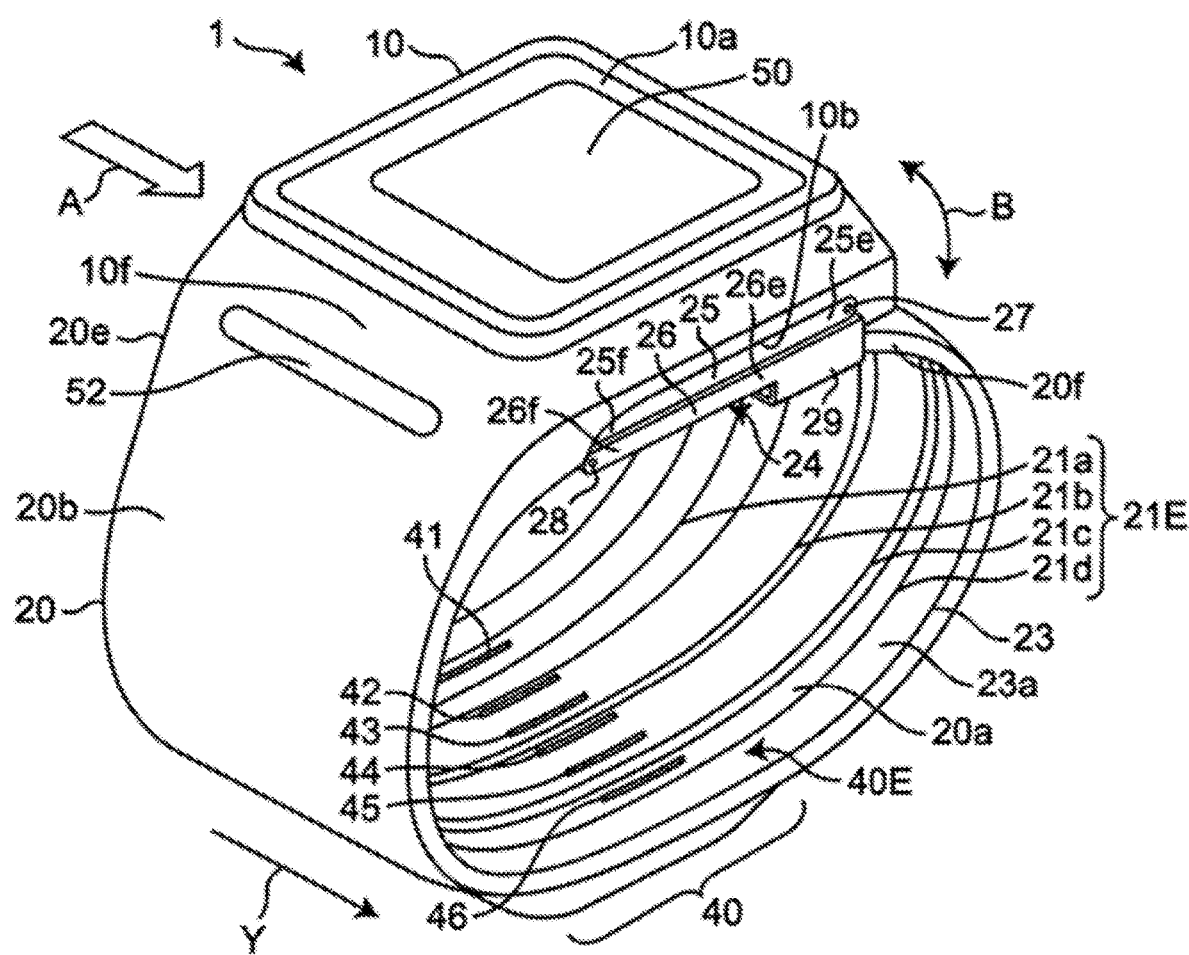
FIG. 1 is a perspective view showing the appearance of a wrist-type sphygmomanometer according to a first embodiment according to a blood pressure measurement device provided with a pulse wave measurement device of the present invention.
Figure 2:
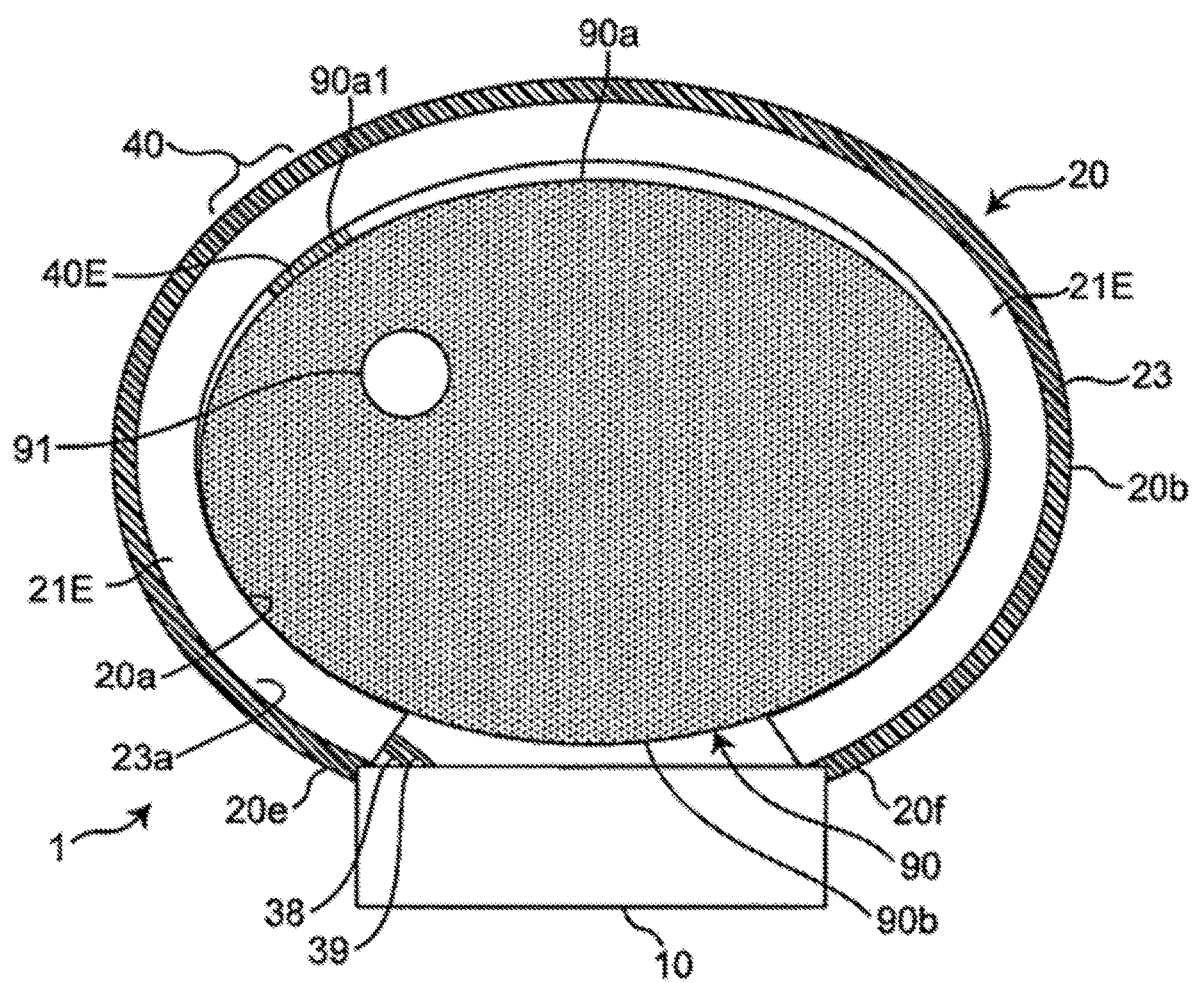
FIG. 2 is a diagram schematically showing a cross-section perpendicular to the longitudinal direction of a wrist in a state where the sphygmomanometer is worn on a left wrist.

FIG. 1 is a perspective view showing an appearance of a wrist type sphygmomanometer (generally indicated by reference sign 1) of the first embodiment. FIG. 2 schematically shows a cross-section perpendicular to a longitudinal direction of a left wrist 90 in a state where a sphygmomanometer 1 is worn on the left wrist 90 as a measurement target site (hereinafter referred to as "wearing state").

As shown in these figures, the sphygmomanometer 1 roughly includes a belt 20 to be worn so as to surround the user's left wrist 90, and a main body 10 integrally fitted to the belt 20.

As can be well understood from FIG. 1, the belt 20 has an elongated band-like shape so as to surround the left wrist 90 along a circumferential direction. The belt 20 includes a strip 23 forming an outer peripheral surface 20b, and a press cuff group 21E which is fitted along an inner peripheral surface 23a of the strip 23 and forms an inner peripheral surface 20a to be in contact with the left wrist 90 (see FIG. 2). The press cuff group 21E acting as a pressing unit is divided with respect to a width direction Y of the belt 20, and includes a press cuff 21a as a third pressing member, a press cuff 21b as a first pressing member, a press cuff 21c as a second pressing member and a press cuff 21d as a fourth pressing member. The press cuff group 21E will be described in detail later. The dimension (width dimension) in the width direction Y of the belt 20 is set to about 30 mm in this example.

The main body 10 is integrally provided to one end portion 20e of the belt 20 in the circumferential direction thereof by integral molding in this example. Note that the belt 20 and the main body 10 may be formed separately from each other and then the main body 10 may be integrally fitted to the belt 20 via a fitting member (for example, a hinge or the like). In this example, a site where the main body 10 is arranged is scheduled to meet a back side surface (a surface on a back side of a hand) 90b of a left wrist 90 in a wearing state (see FIG. 2). A radial artery 91 passing near a palmar side surface (a surface on a palm side) 90a in the left wrist 90 is shown in FIG. 2.

As can be well understood from FIG. 1, the main body 10 has a three-dimensional shape having a thickness in a direction perpendicular to the outer peripheral surface 20b of the belt 20. The main body 10 is formed to be compact and thin so as not to disturb user's daily activities. In this example, the main body 10 has a contour having a truncated quadrangular pyramid shape projecting outward from the belt 20.

A display unit 50 serving as a display screen is provided on the top surface (a surface farthest from a measurement target site) 10a of the main body 10. An operation unit 52 for inputting an instruction from the user is provided along a side surface 10f of the main body 10 (a side surface on a left front side in FIG. 1).

An impedance measurement unit 40 constituting first and second pulse wave sensors is provided on an inner peripheral surface 20a of the press cuff group 21E which is a site between the one end portion 20e and the other end portion 20f of the belt 20 in the circumferential direction and serves as an inner peripheral surface 20a of the belt 20. Six plate-like (or sheet-like) electrodes 41 to 46 (these electrodes are generally referred to as an "electrode group" and indicated by reference sign 40E) are arranged on the inner peripheral surface 20a of the site where the impedance measurement unit 40 is arranged in a state where the electrodes are spaced from one another with respect to the width direction Y of the belt 20) (which will be described in detail later). In this example, a site where the electrode group 40E is arranged is scheduled to meet the radial artery 91 of the left wrist 90 under the wearing state (see FIG. 2).

As shown in FIG. 1, the bottom surface (a surface closest to the measurement target site) 10b of the main body 10 and the end portion 20f of the belt 20 are connected to each other by a threefold buckle 24. The buckle 24 includes a first plate-like member 25 arranged on an outer peripheral side and a second plate-like member 26 arranged on an inner peripheral side. One end portion 25e of the first plate-like member 25 is rotatably fitted to the main body 10 via a connecting rod 27 extending along the width direction Y. The other end portion 25f of the first plate-like member 25 is rotatably fitted to one end portion 26e of the second plate-like member 26 via a connecting rod 28 extending along the width direction Y. The other end portion 26f of the second plate-like member 26 is fixed in the neighborhood of the end portion 20f of the belt 20 by a fixing portion 29. Note that the fitting position of the fixing portion 29 in the circumferential direction of the belt 20 is variably set in advance in accordance with the circumferential length of the left wrist 90 of the user. Thus, the sphygmomanometer 1 (belt 20) is configured in a substantially annular shape as a whole, and the bottom surface 10b of the main body 10 and the end portion 20f of the belt 20 can be opened and closed in an arrow B direction by the buckle 24.

When the user wears the sphygmomanometer 1 on the left wrist 90, the user inserts the left hand through the belt 20 in a direction indicated by an arrow A in FIG. 1 in a state where the buckle 24 is opened to increase the diameter of the ring of the belt 20. Then, as shown in FIG. 2, the user adjusts the angular position of the belt 20 around the left wrist 90 to position the impedance measurement unit 40 of the belt 20 on the radial artery 91 passing through the left wrist 90. As a result, the electrode group 40E of the impedance measurement unit 40 is set to abut against a portion 90a1 of the palmar side surface 90a of the left wrist 90 which meets the radial artery 91. In this state, the user closes and fixes the buckle 24. Thus, the user wears the sphygmomanometer 1 (belt 20) on the left wrist 90.

As shown in FIG. 2, in this example, the strip 23 is made of a plastic material which is flexible in the thickness direction and substantially non-stretchable in the circumferential direction (longitudinal direction). In this example, the press cuff group 21E is configured as a fluid bag by confronting two stretchable polyurethane sheets in the thickness direction and welding peripheral edge portions thereof. As described above, the electrode group 40E of the impedance measurement unit 40 is arranged at a site of the inner peripheral surface 20a of the press cuff group 21E (belt 20) which meets the radial artery 91 of the left wrist 90.

Figure 3:
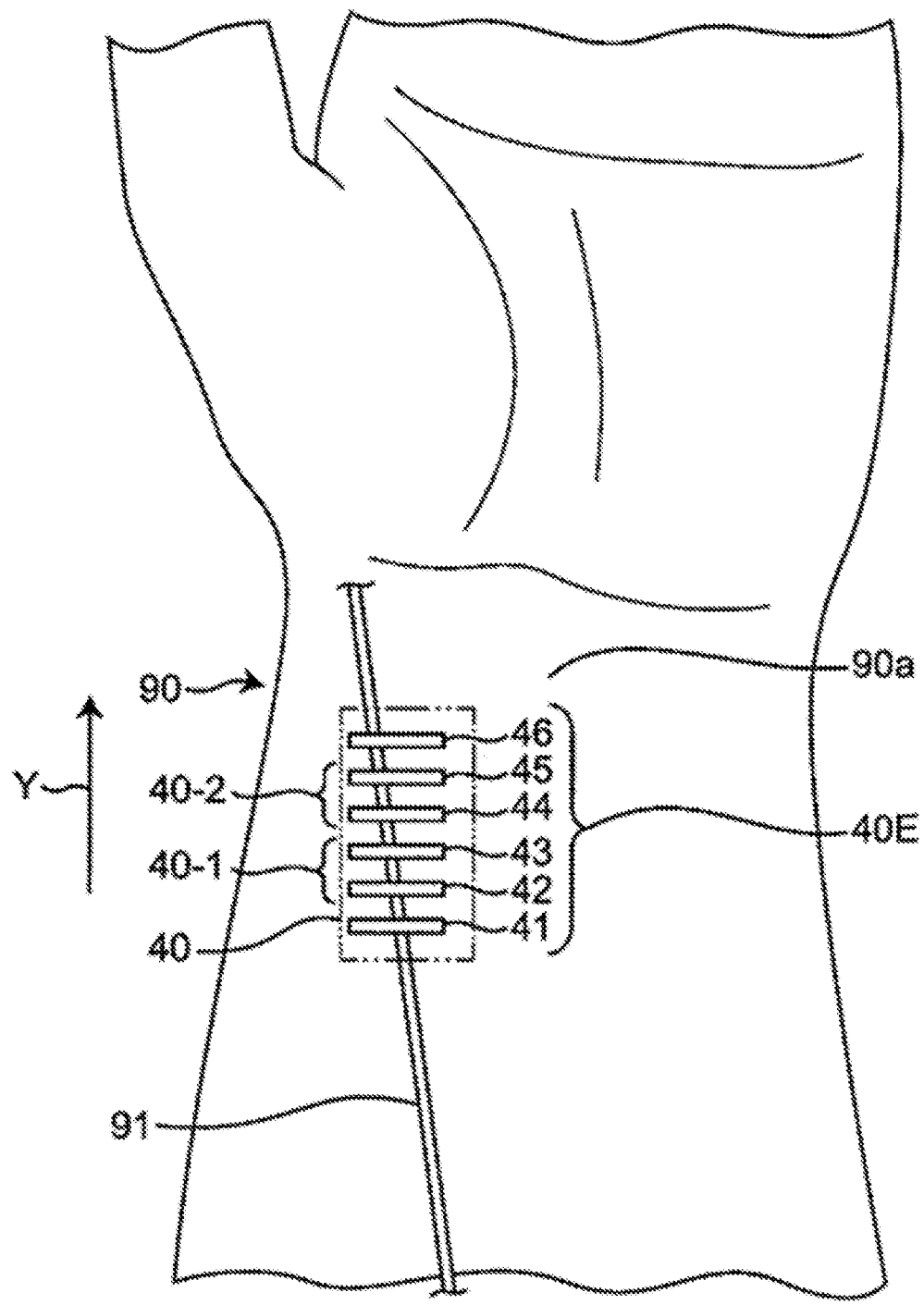
FIG. 3 is a diagram showing a planar layout of impedance measurement electrodes constituting first and second pulse wave sensors in a state where the sphygmomanometer is worn on the left wrist.

As shown in FIG. 3, under the wearing state, the electrode group 40E of the impedance measurement unit 40 is set to be arranged in line along the longitudinal direction of the wrist (corresponding to the width direction Y of the belt 20) so as to meet the radial artery 91 of the left wrist 90. The electrode group 40E has paired current electrodes 41 and 46 for energization arranged on both sides with respect to the width direction Y, paired first detection electrodes 42 and 43 constituting a first pulse wave sensor 40-1 for voltage detection, and paired second detection electrodes 44 and 45 constituting a second pulse wave sensor 40-2 for voltage detection, the paired first detection electrodes 42 and 43 and the paired second detection electrodes 44 and 45 being arranged between the paired current electrodes 41 and 46. The paired second detection electrodes 44 and 45 are arranged so as to meet a further downstream portion of blood flow of the radial artery 91 with respect to the paired first detection electrodes 42 and 43. With respect to the width direction Y, the distance D (see FIG. 5A) between the center of the paired first detection electrodes 42 and 43 and the center of the paired second detection electrodes 44 and 45 is set to 20 mm in this example. This distance D corresponds to a substantial interval between the first pulse wave sensor 40-1 and the second pulse wave sensor 40-2. Furthermore, with respect to the width direction Y, the interval between the paired first detection electrodes 42 and 43 and the interval between the paired second detection electrodes 44 and 45 are both set to 2 mm in this example.

Such an electrode group 40E may be configured to be flat. Therefore, in the sphygmomanometer 1, the belt 20 may be configured to be thin as a whole.

Figure 4:
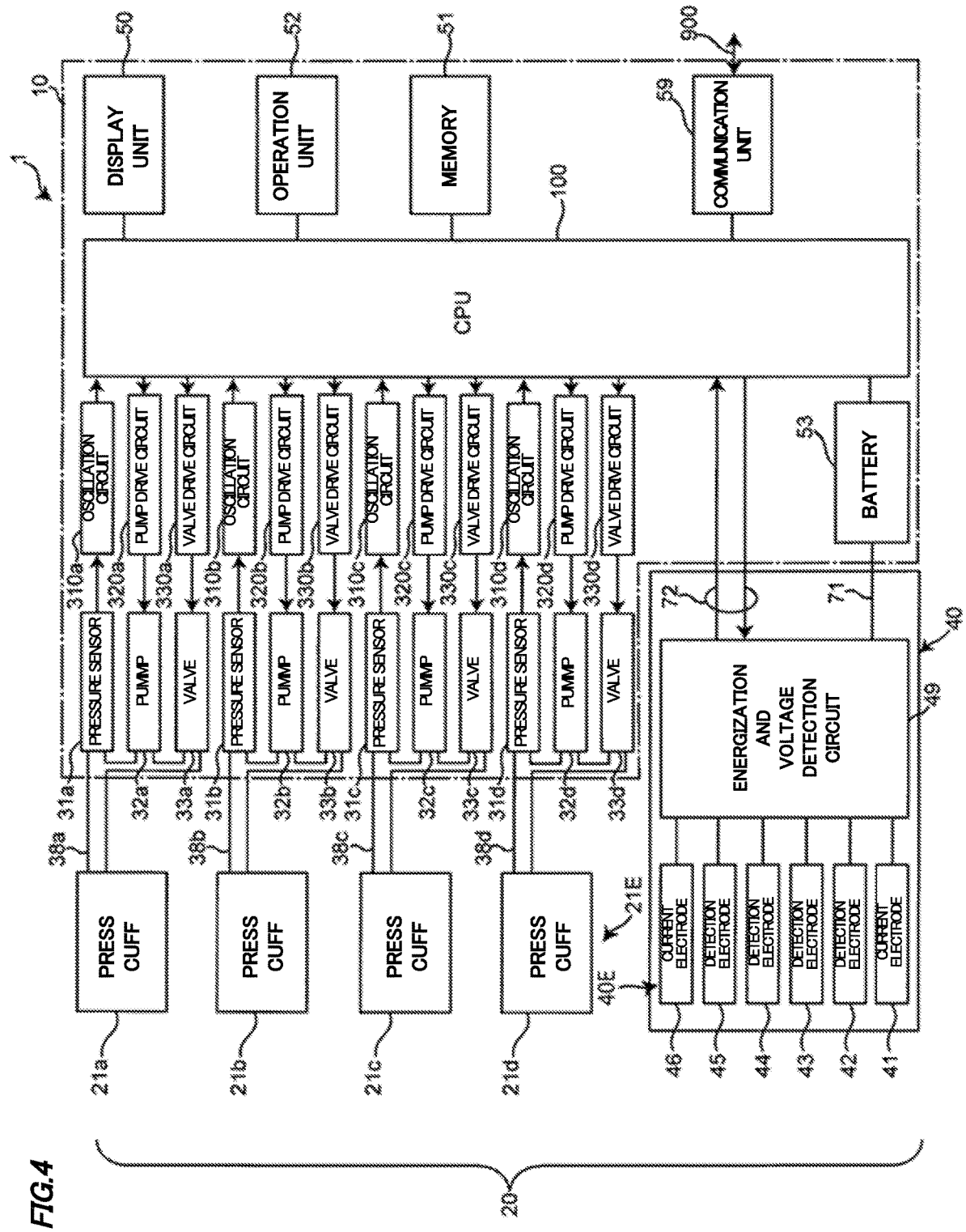
FIG. 4 is a diagram showing a block configuration of a control system of the sphygmomanometer.

FIG. 4 shows a block configuration of a control system of the sphygmomanometer 1. In addition to the display unit 50 and the operation unit 52 described above, a central processing unit (CPU) 100 as a control unit, a memory 51 as a storage unit, and a communication unit 59 are mounted in the main body 10 of the sphygmomanometer 1. Furthermore, pressure sensors 31a, 31b, 31c, and 31d, pumps 32a, 32b, 32c, and 32d, and valves 33a, 33b, 33c, and 33d are mounted in the main body 10 (note that, in the following description, these units may be collectively referred to as a pressure sensor 31, a pump 32, and a valve 33). In the main body 10 are also mounted oscillation circuits 310a, 310b, 310c, and 310d for converting respective outputs from the pressure sensors 31a, 31b, 31c, and 31d into frequencies, pump drive circuits 320a, 320b, 320c, and 320d for driving the pumps 32a, 32b, 32c, and 32d respectively, and valve drive circuits 330a, 330b, 330c, and 330d for driving the valves 33a, 33b, 33c, and 33d, respectively (note that, in the following description, these units may be collectively referred to as an oscillation circuit 310, a pump drive circuit 320, and a valve drive circuit 330). In addition to the electrode group 40E described above, an energization and voltage detection circuit 49 is mounted in the impedance measurement unit 40.

In this example, the display unit 50 includes an organic electro luminescence (EL) display, and displays information on blood pressure measurement such as blood pressure measurement results and other information according to a control signal from the CPU 100. Note that the display unit 50 is not limited to the organic EL display, and may be another type of display unit such as a liquid crystal display (LCD).

In this example, the operation unit 52 is a push type switch, and inputs an operation signal corresponding to a user's instruction to start or stop blood pressure measurement to the CPU 100. Note that the operation unit 52 is not limited to the push type switch, and may be, for example, a pressure-sensitive (resistive) type or proximity (electrostatic capacitive) type touch panel switch or the like. Furthermore, a microphone (not shown) may be provided to input an instruction for starting the blood pressure measurement with a user's voice.

The memory 51 non-temporarily stores data of a program for controlling the sphygmomanometer 1, data used to control the sphygmomanometer 1, setting data for setting various functions of the sphygmomanometer 1, data of measurement results of blood pressure values, etc. The memory 51 is also used as a work memory or the like when the program is executed.

The CPU 100 executes various functions as a control unit in accordance with the program which is stored in the memory 51 and controls the sphygmomanometer 1. For example, when the blood pressure measurement based on the oscillometric method is performed, CPU 100 performs control of driving the pump 32 (and the valve 33) based on a signal from the pressure sensor 31 in response to an instruction for starting the blood pressure measurement from the operation unit 52. Furthermore, in this example, the CPU 100 performs control of calculating a blood pressure value based on a signal from the pressure sensor 31.

The communication unit 59 is controlled by the CPU 100 to transmit predetermined information to an external device via a network 900, and receive information from the external device via the network 900 to deliver the information to the CPU 100. Communication via the network 900 may be performed wirelessly or via a wire. In this embodiment, the network 900 is the Internet. However, the network 900 is not limited to the Internet, but may be another type of network such as an in-hospital local area network (LAN), or one-to-one communication using a USB cable or the like. The communication unit 59 may include a micro USB connector.

In this example, the pump 32 includes a piezoelectric pump, and supplies air as a pressuring fluid to the press cuff group 21E in order to increase the pressure (cuff pressure) in the press cuff group 21E. The valve 33 is opened or closed to discharge or enclose the air from or in the press cuff group 21E to control the cuff pressure. The pump drive circuit 320 drives the pump 32 based on a control signal supplied from the CPU 100. The valve drive circuit 330 opens or closes the valve 33 based on a control signal supplied from the CPU 100.

In this example, the pressure sensor 31 is a piezoresistive pressure sensor, and is connected to the pump 32, the valve 33, and the press cuff group 21E via an air pipe 38 (38a, 38b, 38c, and 38d). The pressure sensor 31 detects the pressure of the belt 20 (the press cuff group 21E), in this example, the pressure with the atmospheric pressure as a reference (zero) through the air pipe 38, and outputs the detected pressure as a time-sequential signal. The oscillation circuit 310 oscillates in response to an electrical signal value based on a change in electrical resistance caused by a piezoresistive effect from the pressure sensor 31, and outputs a frequency signal having a frequency corresponding to the electrical signal value of the pressure sensor 31 to the CPU 100. In this example, the output of the pressure sensor 31 is used to control the pressure of the press cuff group 21E and calculate a blood pressure value (containing systolic blood pressure (SBP) and diastolic blood pressure (DBP)) by the oscillometric method.

When the blood pressure is measured according to a general oscillometric method, the following operation is generally performed. That is, the cuff is wound around a measurement target site (an arm or the like) of a subject in advance, and at the time of measurement, the CPU 100 controls the pump 32 and the valve 33 so that the cuff pressure is increased to be higher than the maximum blood pressure and then gradually reduced. In the pressure-reducing step, the cuff pressure is detected by the pressure sensor, and fluctuation in arterial volume occurring in the artery at the measurement target site is extracted as a pulse wave signal. The maximum blood pressure (systolic blood pressure) and the lowest blood pressure (diastolic blood pressure) are calculated based on the change (mainly rising and falling) of the amplitude of the pulse wave signal which accompanies the change of the cuff pressure at that time. Furthermore, when the pressure of the press cuff group 21E is controlled for the blood pressure measurement based on the pulse transit time, the CPU 100 controls the pump 32 and the valve 33 to increase or reduce the cuff pressure according to various conditions. Details will be described later.

A battery 53 is an element mounted in the main body 10, and in this example, the battery 53 supplies power to each element of the CPU 100, the pressure sensor 31, the pump 32, the valve 33, the display unit 50, the memory 51, the communication unit 59, the oscillation circuit 310, and the pump drive circuit 320. The battery 53 also supplies power to the energization and voltage detection circuit 49 of the impedance measurement unit 40 through a wiring 71. The wiring 71 is provided so as to extend between the main body 10 and the impedance measurement unit 40 along the circumferential direction of the belt 20 in a state where the wiring 71 is interposed between the strip 23 of the belt 20 and the press cuff group 21E together with a wiring 72 for signals.

Figure 5A:
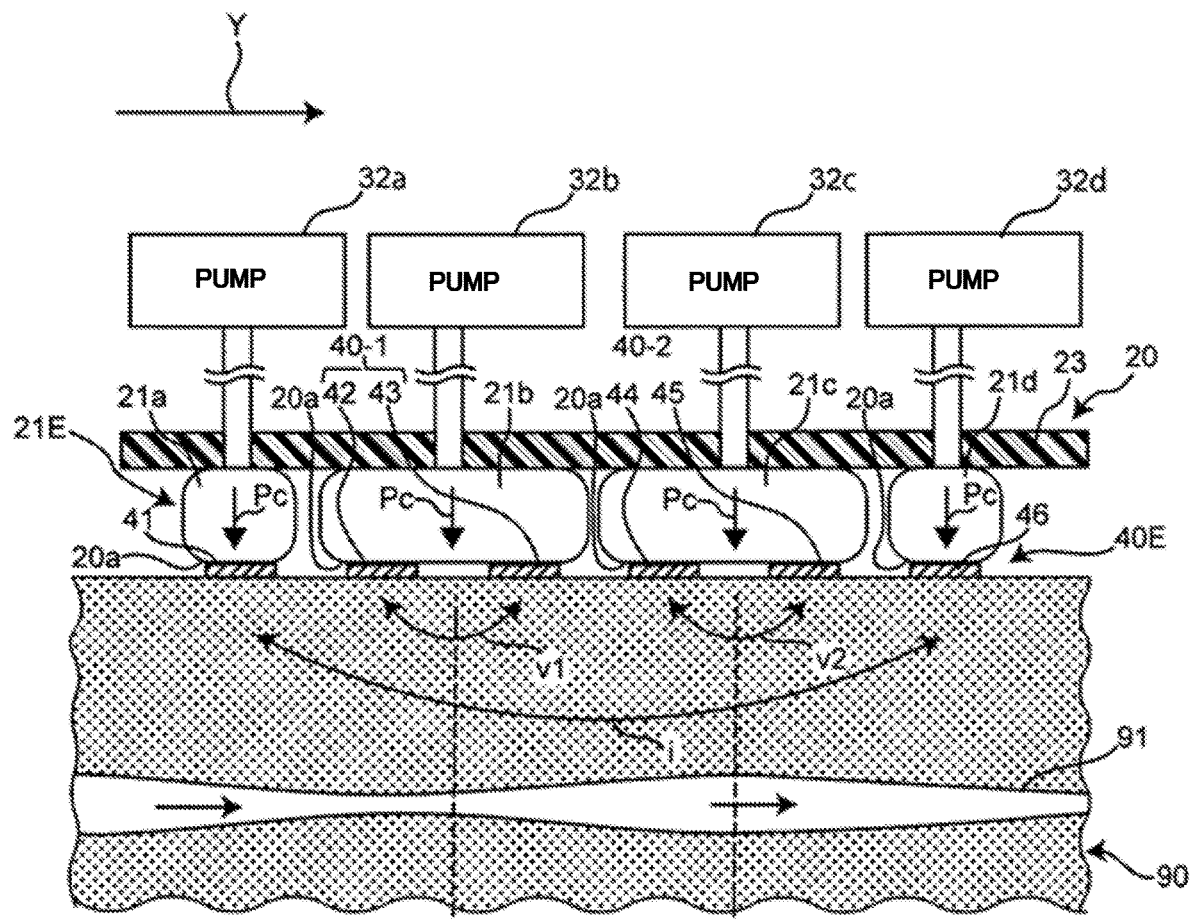
FIG. 5A is a diagram schematically showing a cross-section along the longitudinal direction of the wrist in a state where the sphygmomanometer is worn on the left wrist.
Figure 5B:
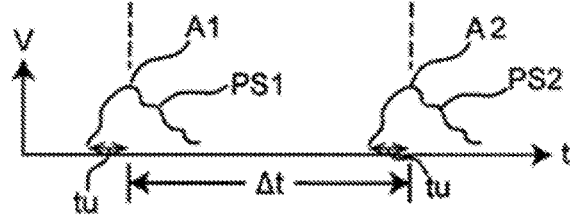
FIG. 5B is a diagram showing waveforms of first and second pulse wave signals output from the first and second pulse wave sensors, respectively.

FIG. 5A schematically shows a cross-section along the longitudinal direction of the wrist in a state where the sphygmomanometer 1 is worn on the left wrist 90. FIG. 5B shows the waveforms of a first pulse wave signal PS1 and a second pulse wave signal PS2 output by the first pulse wave sensor 40-1 and the second pulse wave sensor 40-2, respectively. The energization and voltage detection circuit 49 of the impedance measurement unit 40 is controlled by the CPU 100, and during the operation thereof, in this example, a high frequency constant current i having a frequency of 50 kHz and a current value of 1 mA is made to flow between the paired current electrodes 41 and 46 arranged on both sides with respect to the longitudinal direction of the wrist (corresponding to the width direction Y of the belt 20) as shown in FIG. 5A. Under this state, the energization and voltage detection circuit 49 detects a voltage signal v1 between the paired first detection electrodes 42 and 43 constituting the first pulse wave sensor 40-1 and a voltage signal v2 between the paired second detection electrodes 44 and 45 constituting the second pulse wave sensor 40-2. These voltage signals v1 and v2 represent changes in electrical impedance caused by pulse waves of blood flow of the radial artery 91 at portions of the palmar side surface 90a of the left wrist 90 which are opposed to the first pulse wave sensor 40-1 and the second pulse wave sensor 40-2, respectively (impedance system). The energization and voltage detection circuit 49 rectifies, amplifies and filters these voltage signals v1 and v2 to time-sequentially output a first pulse wave signal PS1 and a second pulse wave signal PS2 having mountain-like waveforms as shown in FIG. 5B. In this example, the voltage signals v1 and v2 are approximately 1 mV. The peaks A1 and A2 of the first pulse wave signal PS1 and the second pulse wave signal PS2 are approximately 1 V in this example.

Note that assuming that the pulse wave velocity (PWV) of the blood flow of the radial artery 91 is in the range of 1000 cm/s to 2000 cm/s, the time difference Δt between the first pulse wave signal PS1 and the second pulse wave signal PS2 is in the range of 1.0 ms to 2.0 ms because the substantial distance D between the first pulse wave sensor 40-1 and the second pulse wave sensor 40-2 is equal to 20 mm.

As shown in FIG. 5A, the press cuffs 21a and 21d are separated from each other in connection with the paired current electrodes 41 and 46 respectively, and the paired current electrodes 41 and 46 are arranged on the inner peripheral surfaces 20a of the press cuffs 21a and 21d (the belt 20). Therefore, when pressure is applied to the press cuffs 21a and 21d by the pumps 32a and 32d, the press cuffs 21a and 21d press the paired current electrodes 41 and 46 against the palmar side surface 90a of the left wrist 90. Likewise, the press cuffs 21b and 21c are separated from each other in connection with the first pulse wave sensor 40-1 and the second pulse wave sensor 40-2 respectively, and the first pulse wave sensor 40-1 and the second pulse wave sensor 40-2 are arranged on the inner peripheral surfaces 20a of the press cuffs 21b and 21c (the belt 20). Accordingly, when pressure is applied to the press cuffs 21b and 21c by the pumps 32b and 32c, the press cuffs 21b and 21c press the first pulse wave sensor 40-1 and the second pulse wave sensor 40-2 against the palmar side surface 90a of the left wrist 90. In this example, the pumps 32a, 32b, 32c, and 32d can individually increase the pressure of the press cuffs 21a, 21b, 21c, and 21d under the control of the CPU 100. Accordingly, the pressing forces of the paired current electrodes 41 and 46, the first pulse wave sensor 40-1, and the second pulse wave sensor 40-2 against the palmar side surface 90a of the left wrist 90 can be set to a proper value.

(Blood Pressure Measurement Operation Based on Oscillometric Method)

Figure 6:
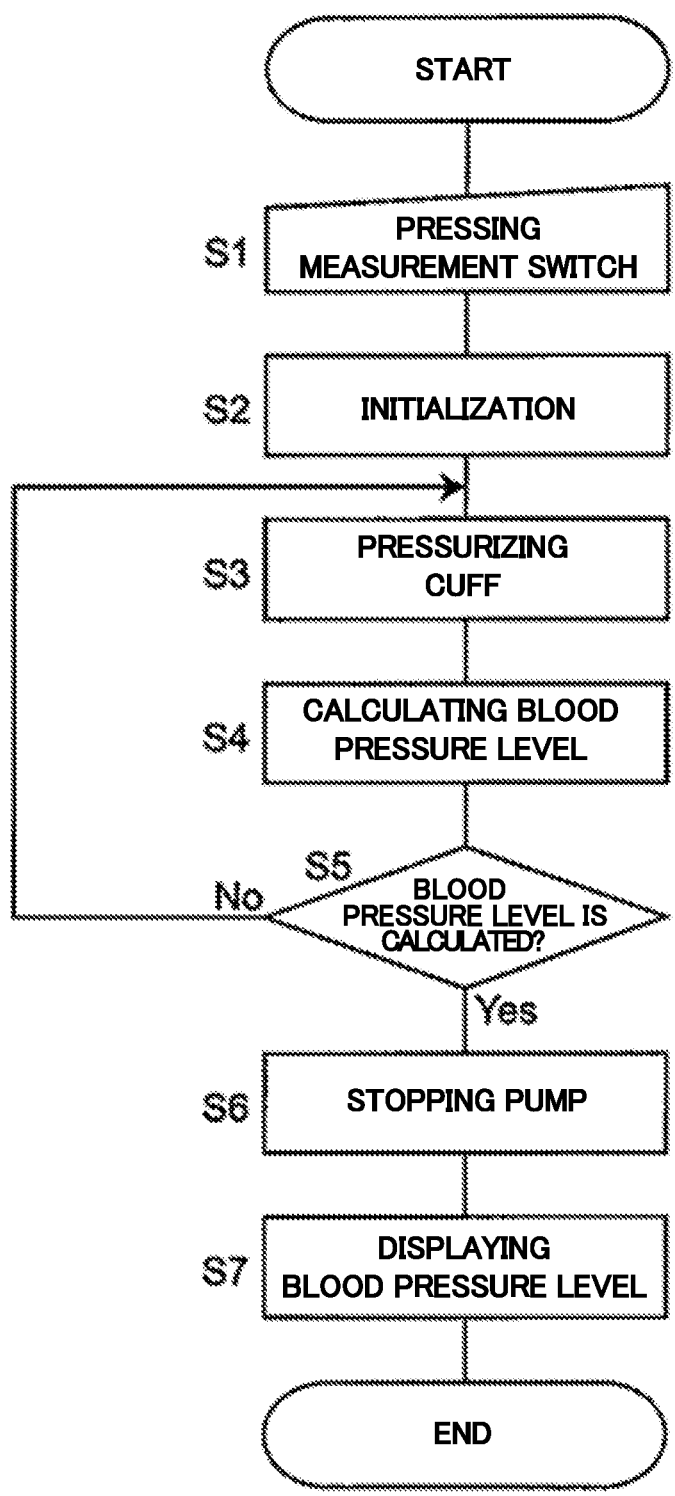
FIG. 6 is a diagram showing an operation flow when the sphygmomanometer performs blood pressure measurement by an oscillometric method.

FIG. 6 shows an operation flow when the sphygmomanometer 1 performs blood pressure measurement based on the oscillometric method.

When the user instructs blood pressure measurement based on the oscillometric method with the push type switch as the operation unit 52 provided to the main body 10 (step S1), the CPU 100 starts to operate and initializes a processing memory area (step S2). Furthermore, the CPU 100 outputs a control signal to the valve drive circuit 330. The valve drive circuit 330 opens the valve 33 based on the control signal to exhaust air in the press cuff group 20E. Subsequently, the CPU 100 performs control to set an output value of the pressure sensor 31 at the present time as a value corresponding to the atmospheric pressure (0 mmHg adjustment). In this example, the CPU 100 performs this control for all the press cuffs 21a, 21b, 21c, and 21d.

Subsequently, CPU 100 works as a pressure control unit to close the valve 33 via the valve drive circuit 330, and then performs control to drive the pump 32 via the pump drive circuit 320 to feed air to the press cuff group 21E. As a result, the press cuff group 21E is expanded and the cuff pressure Pc (see FIG. 7) is gradually increased (step S3 in FIG. 6). In this example, the CPU 100 performs this control for all the press cuffs 21a, 21b, 21c, and 21d.

Figure 7:
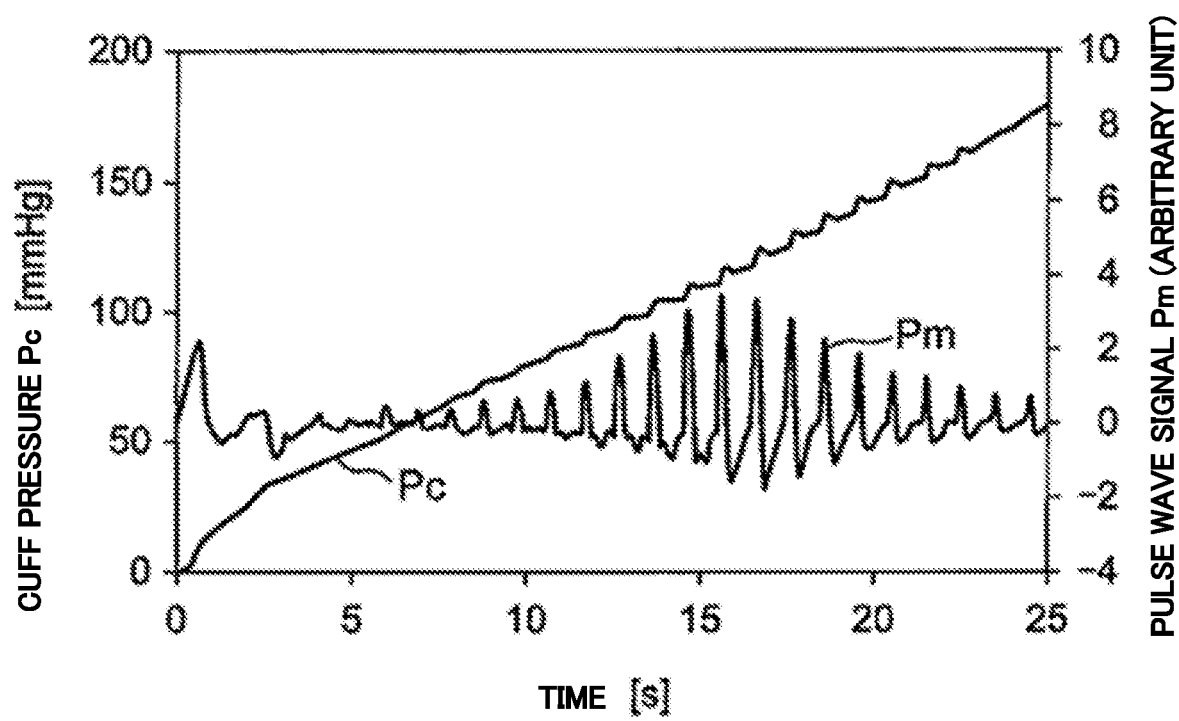
FIG. 7 is a diagram showing variations in cuff pressure and pulse wave signal according to the operation flow of FIG. 6.

In this pressure-increasing step, the CPU 100 monitors the cuff pressure Pc by the pressure sensor 31 to calculate the blood pressure value, and acquire a fluctuation component of the arterial volume occurring in the radial artery 91 of the left wrist 90 as the measurement target site as a pulse wave signal Pm as shown in FIG. 7. Note that the CPU 100 may monitor all the cuff pressures Pc of the press cuffs 21a, 21b, 21c, and 21d and calculate an average value thereof, or may monitor the cuff pressure Pc of any press cuff of the press cuffs 21a, 21b, 21c, and 21d.

Next, in step S4 in FIG. 6, the CPU 100 works as a second blood pressure calculation unit, and attempts calculating a blood pressure value (a systolic blood pressure SBP and a diastolic blood pressure DBP) by applying a publicly-known algorithm according to the oscillometric method based on the pulse wave signal Pm which has been acquired at this time.

When no blood pressure value can be calculated at this time point because of insufficient data (NO in step S5), the processing of steps S3 to S5 is repeated unless the cuff pressure Pc has reached an upper limit pressure (which is predetermined to, for example, 300 mmHg for safety).

When the blood pressure value can be calculated in this way (YES in step S5), the CPU 100 performs control to stop the pump 32 via the pump drive circuit 320 and open the valve 33 via the valve drive circuit 330 to exhaust air in the press cuff group 21E (step S6). Finally, the measurement result of the blood pressure value is displayed on the display unit 50 and recorded in the memory 51 (step S7).

Note that the calculation of the blood pressure value is not limitedly performed in the pressure-increasing step, but may be performed in the pressure-reducing step.

(Blood Pressure Measurement Operation Based on Pulse Transit Time)

Figure 8:
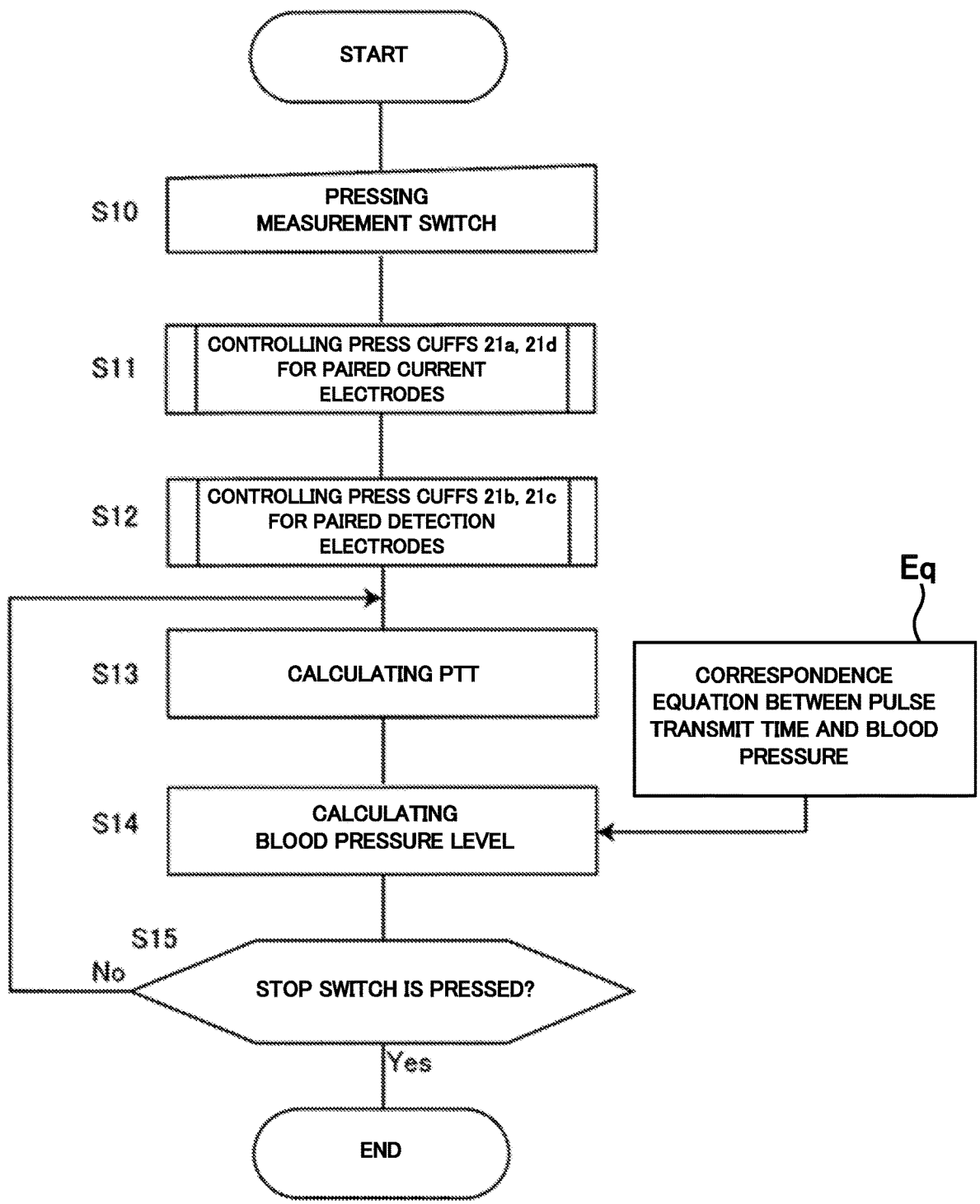
FIG. 8 is a diagram showing an operation flow when the sphygmomanometer executes a pulse wave measurement method according to an embodiment to acquire a pulse transit time (PTT) and performs blood pressure measurement (estimation) based on the pulse transit time.

FIG. 8 shows an operation flow when the sphygmomanometer 1 executes a pulse wave measurement method according to an embodiment to acquire a pulse transit time (PTT) and performs blood pressure measurement (estimation) based on the pulse transit time.

Figure 9:
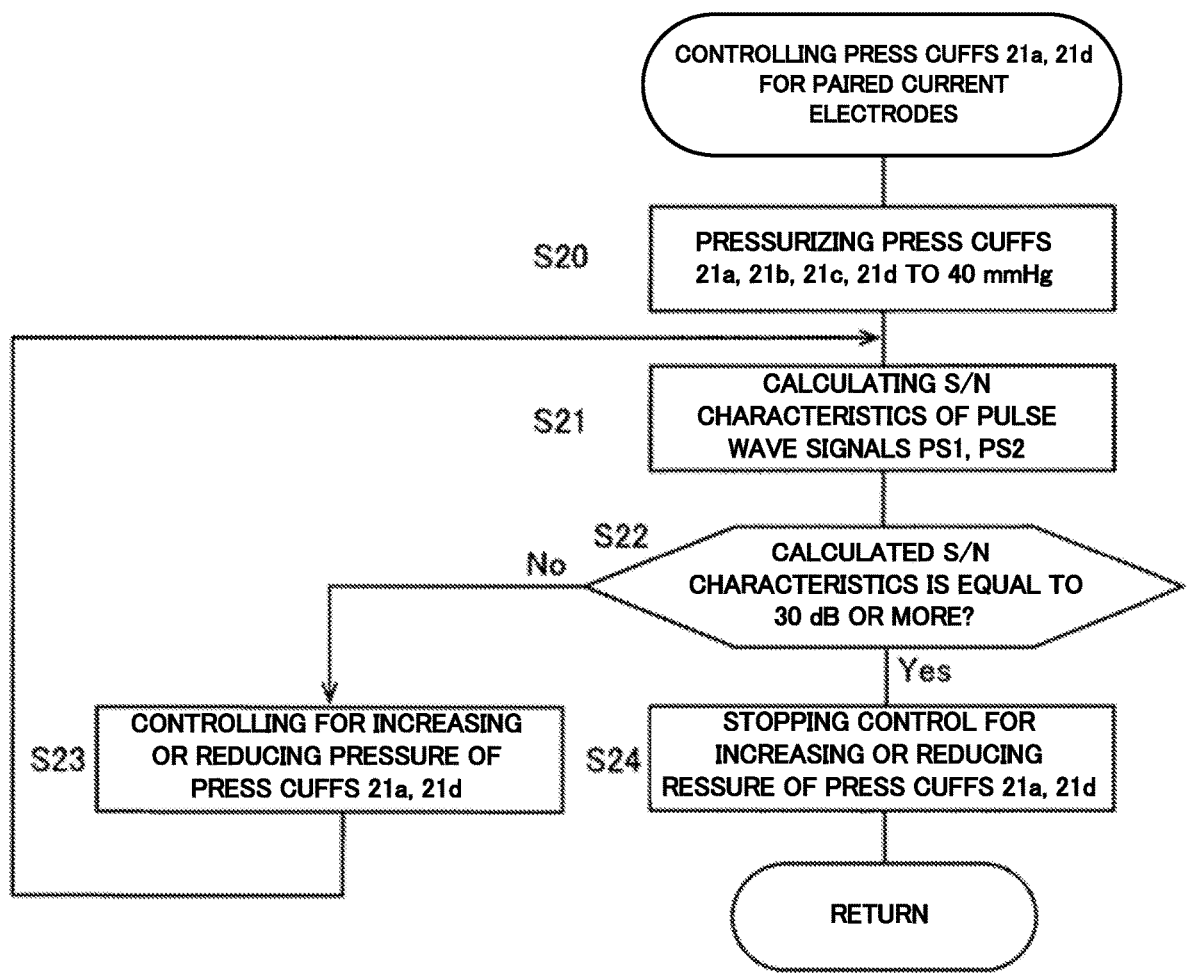
FIG. 9 is a diagram showing an operation flow when cuffs for a current electrode pair shown in the operation flow of FIG. 8 are controlled.

When the user instructs PTT-based blood pressure measurement by means of the push type switch as the operation unit 52 provided to the main body 10 (step S10 in FIG. 8), the CPU 100 starts to control the press cuffs 21a and 21d corresponding to the paired current electrodes 41 and 46 (step S11 in FIG. 8). FIG. 9 shows an operation flow when the sphygmomanometer 1 controls the press cuffs 21a and 21d.

The operation flow shown in FIG. 9 has been created based on experimental results achieved by the inventors. In the case where the pulse wave is measured by the impedance method as in the case of the present embodiment, when the degree of close contact between the paired current electrodes 41 and 46, the first pulse wave sensor 40-1 and the second pulse wave sensor 40-2 and the skin of the left wrist 90 as the measurement target site is poor, the contact resistance increases, and thus the rate of change in impedance of the artery to be originally detected decreases, so that the S/N characteristic of the measured pulse wave signal (Signal-to-Noise ratio) gets worse. Therefore, the inventors of the present invention have performed experiments for the relationship between the pressing forces of the paired current electrodes 41 and 46, the first pulse wave sensor 40-1, and the second pulse wave sensor 40-2 against the left wrist 90 and the S/N characteristic of the pulse wave signal. As a result, it has been found that when the cuff pressure Pc is increased from about 40 mmHg, the S/N characteristics of the first and second pulse wave signals which are time-sequentially output from the first pulse wave sensor 40-1 and the second pulse wave sensor 40-2 respectively trend to be generally enhanced, and when the cuff pressure Pc decreases to be lower than 40 mmHg, the S/N characteristics may fall below 30 dB. It has been also found that the S/N characteristics tend to be better by user setting the cuff pressure Pc of each of the paired current electrodes 41 and 46, the first pulse wave sensor 40-1, and the second pulse wave sensor 40-2 so that a difference is provided between the cuff pressures Pc at upstream and downstream sides of the artery as compared with a case where the cuff pressures Pc are set to the same pressure.

This operation flow is based on an idea that it is easier to acquire a value of 30 dB or more as the S/N characteristics of the first and second pulse wave signals PS1 and PS2 by first setting initial values of the cuff pressures Pc of all the press cuffs 21a, 21b, 21c, and 21d to 40 mmHg and then adjusting the cuff pressures Pc while the cuff pressures Pc of the press cuffs 21a and 21d corresponding to the paired current electrodes 41 and 46 are balanced with one another. Note that the adjustment of the cuff pressure Pc of each of the first pulse wave sensor 40-1 and the second pulse wave sensor 40-2 is performed after the pressing force of the paired current electrodes 41 and 46 is set.

As shown in FIG. 9, when the control of the press cuffs 21a and 21d corresponding to the paired current electrodes 41 and 46 is started, the CPU 100 works as a current electrode pressing force setting unit and performs control to feed air to the press cuff group 21E by closing the valve 33 via the valve drive circuit 330 and then turning on the pump 32 via the pump drive circuit 320. As a result, the press cuff group 21E is expanded and also the cuff pressure Pc (see FIG. 5A) is gradually increased to 40 mmHg (step S20 in FIG. 9). In this example, the cuff pressure Pc is continuously increased at a constant speed (=5 mmHg/s).

In this pressure-increasing step, the CPU 100 acquires first and second pulse wave signals PS1 and PS2 which are time-sequentially output by the first pulse wave sensor 40-1 and the second pulse wave sensor 40-2 respectively, and calculates the S/N characteristics of the first and second pulse wave signals PS1 and PS2 in real time (step S21 in FIG. 9).

At the same time, the CPU 100 determines whether the calculated S/N characteristic is equal to 30 dB or more (step S22 in FIG. 9). Note that in this example, a value of 30 dB or more is used as a reference value for the determination on the S/N characteristic, but it is possible to use a predetermined value as needed. Here, when the S/N characteristic is less than 30 dB (NO in step S22 in FIG. 9), the CPU 100 drives or stops the pumps 32a and 32d via the pump drive circuits 320a and 320d, or opens or closes the valves 33a and 33d via the valve drive circuits 330a and 330d to increase or reduce the pressures of the press cuffs 21a and 21d (step S23 in FIG. 9). As described above, in this example, the adjustment is performed while balancing the cuff pressures Pc of the press cuffs 21a and 21d corresponding to the paired current electrodes 41 and 46. The processing in steps S21 to S23 is repeated until the S/N characteristic has reached 30 dB or more unless the cuff pressure Pc has reached the upper limit pressure (which is predetermined to, for example, 300 mmHg for safety).

When the S/N characteristic becomes 30 dB or more (YES in step S22 in FIG. 9), the CPU 100 stops the pumps 32a and 32d via the pump drive circuits 320a and 320d (step S23 in FIG. 9), and sets the cuff pressures Pc to values at that time point, that is, values at the time point when the S/N characteristics of the first and second pulse wave signals PS1 and PS2 become 30 dB or more. As described above, the control of the press cuffs 21a and 21d corresponding to the paired current electrodes 41 and 46 (step S11 in FIG. 8) is terminated.

Figure 10:
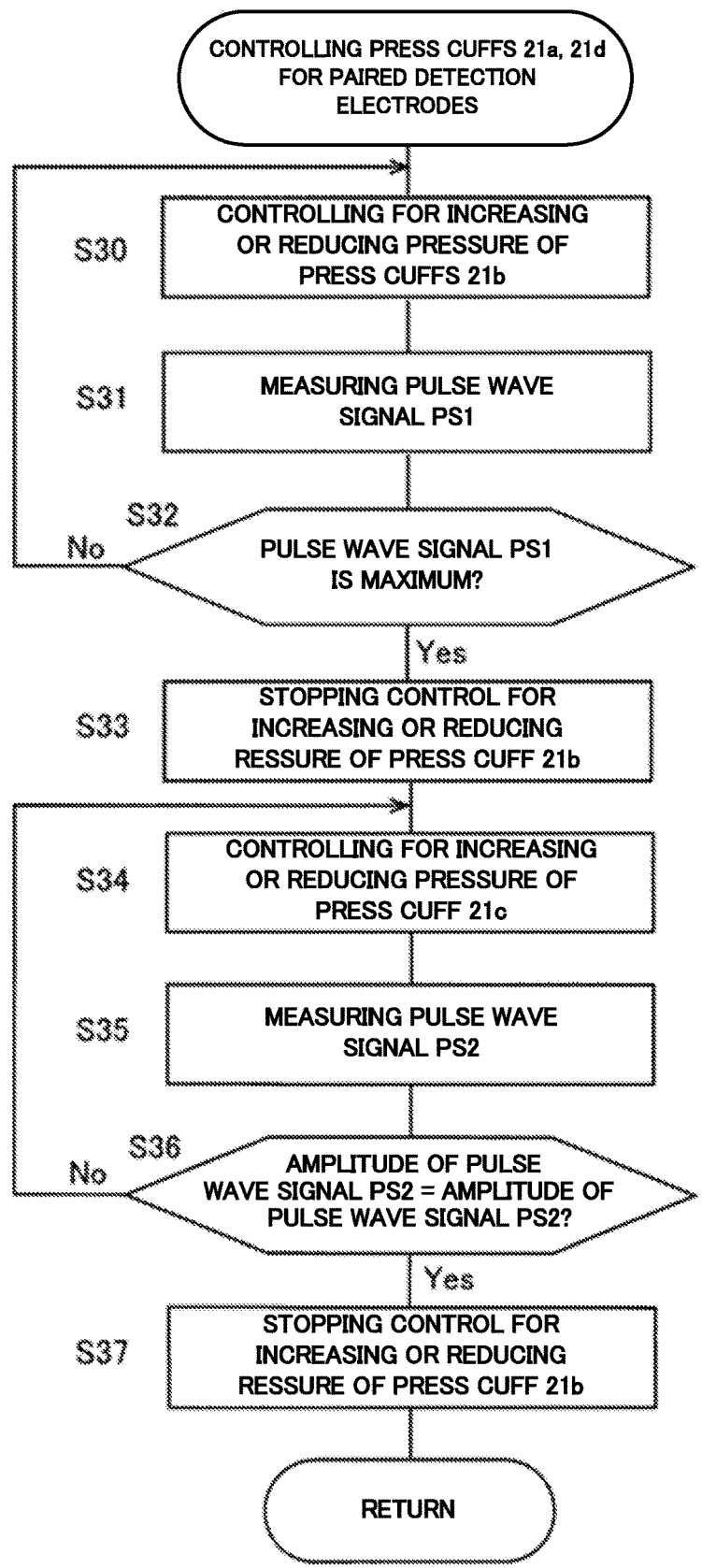
FIG. 10 is a diagram showing an example of an operation flow when the cuffs for a detection electrode pair shown in the operation flow of FIG. 8 are controlled.

Under this state, CPU 100 works as a pulse wave sensor pressing force setting unit, and starts to control the press cuffs 21b and 21c corresponding to the paired first detection electrodes 42 and 43 constituting the first pulse wave sensor 40-1 and the paired second detection electrodes 44 and 45 constituting the second pulse wave sensor 40-2 (step S12 in FIG. 8). FIG. 10 shows an operation flow when the sphygmomanometer 1 controls the press cuffs 21b and 21c.

The operation flow shown in FIG. 10 has been created based on the experimental results achieved by the inventors. Acquisition of the pulse transit time (PTT) is performed, for example by measuring the time difference Δt (see FIG. 5B) between the peak A1 of the first pulse wave signal PS1 and the peak A2 of the second pulse wave signal PS2. Accordingly, it is preferable that the waveform of the first pulse wave signal PS1 and the waveform of the second pulse wave signal PS2 are identical to each other. According to the experiments by the inventors, it has been found that it is easier to acquire the same waveform as the waveform of the first pulse wave signal PS1 and the waveform of the second pulse wave signal PS2 by providing a difference between the cuff pressure Pc of the first pulse wave sensor 40-1 located on the upstream side of the artery and the cuff pressure Pc of the second pulse wave sensor 40-2 located on the downstream side of the artery as compared with a case where the cuff pressure Pc of the first pulse wave sensor 40-1 and the cuff pressure Pc of the second pulse wave sensor 40-2 are set to the same pressure. It has been also found that the relationship in magnitude between the respective cuff pressures Pc necessary to acquire the same waveform is different among users. It is considered that this is based on the fact that the living tissue in the left wrist 90 as the measurement target site is different depending on the user. This operation flow is based on an idea that the same waveform is acquired as the waveform of the first pulse wave signal PS1 and the waveform of the second pulse wave signal PS2 by changing the cuff pressure Pc of each of the press cuffs 21b and 21c corresponding to the first pulse wave sensor 40-1 and the second pulse wave sensor 40-2.

When the control of the press cuffs 21b and 21c corresponding to the first paired detection electrodes 42 and 43 and the paired second detection electrodes 44 and 45 shown in the operation flow of FIG. 10 is started, the cuff pressures Pc of the press cuffs 21a and 21d are set to the values at the time point when the S/N characteristic becomes 30 dB or more as described above (Step S24 in FIG. 9) as described with respect to the control of the press cuffs 21a and 21d corresponding to the paired current electrodes 41 and 46. As shown in FIG. 10, when the control of the press cuffs 21b and 21c is started, the CPU 100 works as a pulse wave sensor pressing force setting unit to drive the pump 32b via the pump drive circuit 320b and increase the pressure of the press cuff 21b corresponding to the first pulse wave sensor 40-1 (step S30 in FIG. 10).

In this pressure-increasing step, CPU 100 acquires the first pulse wave signal PS1 which is time-sequentially output by the first pulse wave sensor 40-1 (step S31 in FIG. 10), and the CPU 100 also determines whether the amplitude of the acquired first pulse wave signal PS1 is maximum (step S32 in FIG. 10).

When the amplitude of the first pulse wave signal PS1 is not maximum (NO in step S32 in FIG. 10), the CPU 100 drives or stops the pump 32b via the pump drive circuit 320b, or opens or closes the valve 33b via the valve drive circuit 330b to increase or reduce the pressure of the press cuff 21b (step S30 in FIG. 10). The processing of steps S30 to S32 is repeated until the amplitude of the first pulse wave signal PS1 becomes maximum unless the cuff pressure Pc has reached the upper limit pressure (which is predetermined to, for example, 300 mmHg for safety). Note that not only increase of pressure, but also reduction of pressure is performed on the press cuff 21b for the following reason. When the pressing force of the first pulse wave sensor 40-1 is increased, the amplitude of the first pulse wave signal PS1 gradually increases, but when the pressing force is increased even after the amplitude of the first pulse wave signal PS1 exhibits a maximum value, there is a tendency that blood vessels collapse and the amplitude of the first pulse wave signal PS1 gradually decrease. Therefore, in this example, not only increase of the pressure of the press cuff 21b, but also reduction of the pressure of the press cuff 21b is performed to acquire the cuff pressure Pc at which the amplitude of the first pulse wave signal PS1 becomes maximum.

When the amplitude becomes maximum (YES in step S32 in FIG. 10), the CPU 100 stops the pump 32b via the pump drive circuit 320b (step S33 in FIG. 10), and sets the cuff pressure Pc of the press cuff 21b to a value at that time point, that is, a value at the time point when the amplitude of the first pulse wave signal PS1 becomes maximum.

Next, the CPU 100 drives the pump 32c via the pump drive circuit 320c to increase the pressure of the press cuff 21c corresponding to the second pulse wave sensor 40-2 (step S34 in FIG. 10).

In this pressure-increasing step, the CPU 100 acquires the second pulse wave signal PS2 which is time-sequentially output by the second pulse wave sensor 40-2 (step S35 in FIG. 10), and the CPU 100 works as a waveform comparing unit to determine whether the amplitude of the acquired second pulse wave signal PS2 is identical to the maximum amplitude of the first pulse wave signal PS1 set as described above (step S36 in FIG. 10). Note that in this example, an allowable range when "identical" is determined is set to a range of ±10%.

When the amplitude of the second pulse wave signal PS2 is not maximum (NO in step S36 in FIG. 10), the CPU 100 drives or stops the pump 32c via the pump drive circuit 320c, or opens or closes the valve 33c via the valve drive circuit 330c to increase or reduce the pressure of the press cuff 21c (step S34 in FIG. 10). The processing of the steps S34 to S36 is repeated until the amplitude of the second pulse wave signal PS2 is equal to the maximum amplitude of the first pulse wave signal PS1 unless the cuff pressure Pc has reached the upper limit pressure (which is predetermined to, for example, 300 mmHg for safety). Note that not only increase of the pressure of the press cuff 21c, but also reduction of the pressure of the press cuff 21c is performed because the relationship between the amplitude of the second pulse wave signal PS2 and the pressing force is similar to the relationship between the amplitude of the first pulse wave signal PS1 and the pressing force.

When the amplitude of the second pulse wave signal PS2 becomes equal to the maximum amplitude of the first pulse wave signal PS1 (YES in step S36 in FIG. 10), the CPU 100 stops the pump 32c via the pump drive circuit 320c (step S37 in FIG. 10), and sets the cuff pressure Pc of the press cuff 21c to a value at that time point, that is, a value at the time point when the amplitude of the second pulse wave signal PS2 becomes equal to the maximum amplitude of the first pulse wave signal PS1. As described above, the control (step S12 in FIG. 8) of the press cuffs 21b and 21c which correspond to the paired first detection electrodes 42 and 43 constituting the first pulse wave sensor 40-1 and the paired second detection electrodes 44 and 45 constituting the second pulse wave sensor 40-2 is terminated.

In this state, the CPU 100 works as a measurement processing unit to acquire the time difference Δt (see FIG. 5B) between the first and second pulse wave signals PS1 and PS2 as a pulse transit time (PTT) (step S13 in FIG. 8). More specifically, in this example, the time difference Δt between the peak A1 of the first pulse wave signal PS1 and the peak A2 of the second pulse wave signal PS2 is acquired as the pulse transit time (PTT).

In the case as described above, the pulse transit time is measured based on the first and second pulse wave signals PS1 and PS2 which have the S/N characteristics of 30 dB or more and the same waveform, so that the measurement accuracy of the pulse transit time can be enhanced. Furthermore, the pulse transit time can be acquired without needlessly increasing the cuff pressure Pc. As a result, a physical burden on a user can be reduced.

Next, the CPU 100 works as a first blood pressure calculation unit, and uses a predetermined correspondence equation Eq between the pulse transit time and the blood pressure to calculate (estimate) the blood pressure based on the pulse transit time (PTT) acquired in step S13 (step S14 in FIG. 8). Here, when the predetermined correspondence equation Eq between the pulse transit time and the blood pressure is provided, for example, as a publicly-known fractional function including a term of $1/DT^2$ as represented by an equation (Eq. 2) in FIG. 32 when the pulse transit time is represented by DT and the blood pressure is represented by EBP (see, for example, Japanese Patent Laid-Open No. 10-201724). In the equation (Eq. 2), each of α and β represents a known coefficient or constant.

When the blood pressure is calculated (estimated) in the above manner, the measurement accuracy of the pulse transit time is enhanced as described above, and thus the measurement accuracy of the blood pressure can be enhanced. Note that the measurement result of the blood pressure value is displayed on the display unit 50 and recorded in the memory 51.

In this example, when stop of measurement is not instructed by the push type switch as the operation unit 52 in step S15 in FIG. 8 (NO in step S15 in FIG. 8), the calculation of the pulse transit time (PTT) (step S13 in FIG. 8) and the calculation (estimation) of the blood pressure (step S14 in FIG. 8) are periodically repeated each time the first and second pulse wave signals PS1 and PS2 are input according to the pulse wave. The CPU 100 updates and displays the measurement result of the blood pressure value on the display unit 50, and accumulates and records the measurement result in the memory 51. When the stop of measurement is instructed in step S15 in FIG. 8 (YES in step S15 in FIG. 8), the CPU 100 opens the valve 33 via the valve drive circuit 330 to control exhaustion of air in the press cuff group 21E, and terminates the measurement operation.

According to the sphygmomanometer 1, the blood pressure can be continuously measured over a long period of time by the blood pressure measurement based on the pulse transit time (PTT) in a state where the physical burden on the user is light.

According to the sphygmomanometer 1, the blood pressure measurement (estimation) based on the pulse transit time and the blood pressure measurement by the oscillometric method can be performed by an integrated device. Therefore, the convenience of the user can be enhanced.

(First Modification)

Figure 11:
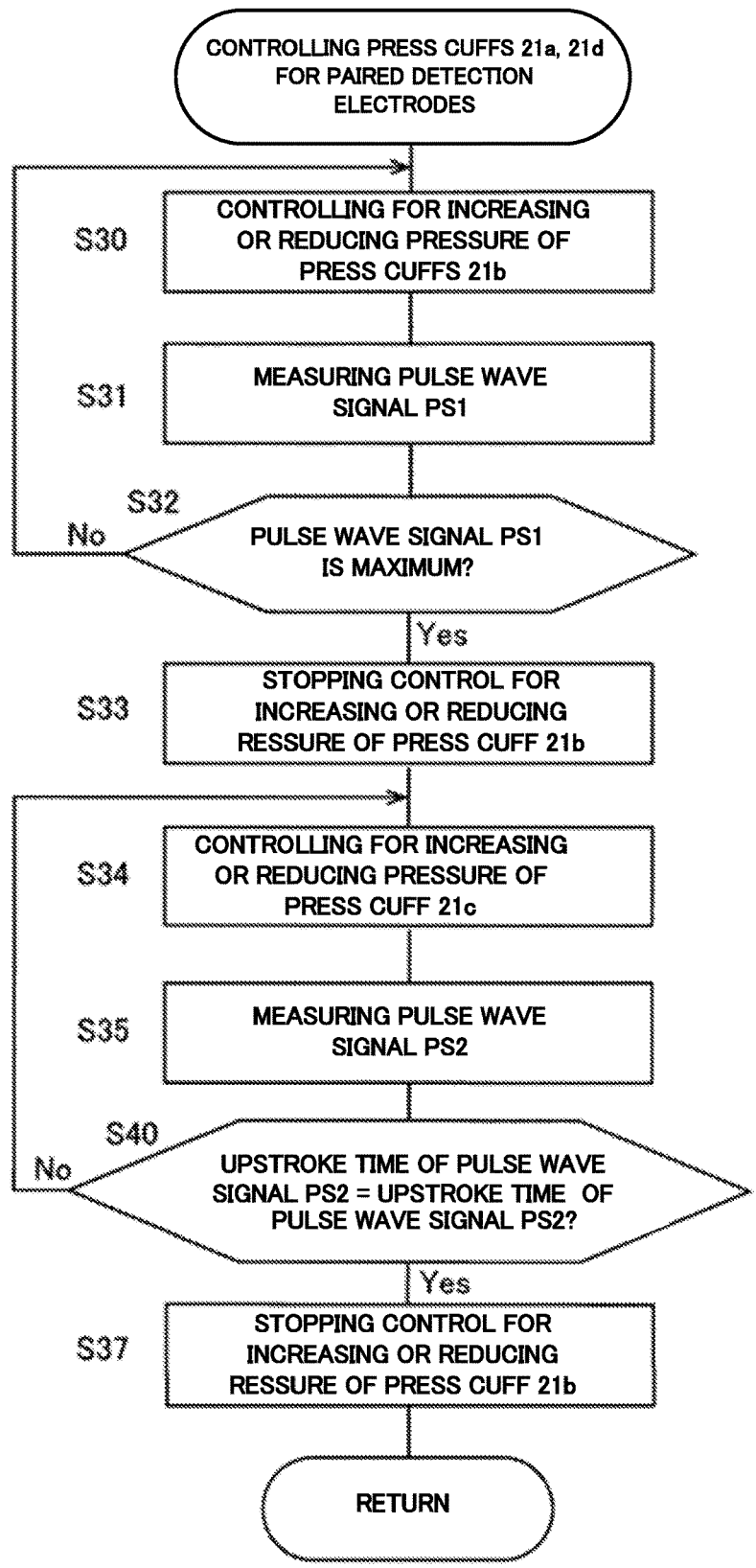
FIG. 11 is a diagram showing another example of the operation flow when the cuffs for the detection electrode pair shown in the operation flow of FIG. 8 are controlled.

FIG. 11 shows another example of the operation flow when the sphygmomanometer 1 controls the press cuffs 21b and 21c. In the example shown in FIG. 10, whether the waveform of the second pulse wave signal PS2 and the waveform of the first pulse wave signal PS1 having the maximum amplitude are identical to each other is determined based on the amplitude of each of the waveforms in step S36. However, the determination is not limited to this manner. For example, as shown in step S40 in FIG. 11, the respective waveforms may be determined to be identical to each other based on whether an upstroke time of the second pulse wave signal PS2 is identical to an upstroke time of the first pulse wave signal PS1 having the maximum amplitude. Here, the upstroke time means, for example, a time to from a rising point of the first pulse wave signal PS1 to the peak A1 (the same applies to the second pulse wave signal PS2) (see FIG. 5B).

As shown in FIG. 11, in this operation flow as well as the operation flow of FIG. 10, the CPU 100 sets the cuff pressure Pc of the press cuff 21b while increasing or reducing the pressure of the press cuff 21b corresponding to the first pulse wave sensor 40-1 so that the amplitude of the first pulse wave signal PS1 becomes maximum (steps S30 to S33 in FIG. 11). In this case, when the CPU 100 determines that the amplitude of the first pulse wave signal PS1 is maximum in the operation flow of FIG. 11 (YES in step S32 in FIG. 11), the CPU 100 records the upstroke time tu of the first pulse wave signal PS1 in the memory 51.

Next, the CPU 100 drives the pump 32c via the pump drive circuit 320c to increase the pressure of the press cuff 21c corresponding to the second pulse wave sensor 40-2 (step S34 in FIG. 11). In this pressure-increasing step, the CPU 100 acquires the second pulse wave signal PS2 which is time-sequentially output by the second pulse wave sensor 40-2 (step S35 in FIG. 11), and the CPU 100 also works as a waveform comparing unit to determine whether the upstroke time tu of the acquired second pulse wave signal PS2 and the upstroke time tu of the first pulse wave signal PS1 recorded in the memory 51 are identical to each other (step S40 in FIG. 11). Note that in this example, an allowable range when it is determined that the upstroke times tu are "identical" is set to a range of ±1%.

Here, when the upstroke time tu of the second pulse wave signal PS2 and the upstroke time tu of the first pulse wave signal PS1 are not identical to each other (NO in step S40 in FIG. 11), the processing of steps S34 to S40 is repeated until the upstroke times tu are identical to each other unless the cuff pressure Pc has reached an upper limit pressure (which is predetermined to, for example, 300 mmHg for safety). When the upstroke times tu become the same (YES in step S40 in FIG. 11), the CPU 100 stops the pump 32c (step S37 in FIG. 11), and sets the cuff pressure Pc of the press cuff 21c to a value at that time, that is, a value at the time point when the upstroke times tu become the same. As a result, the pulse transit time is measured based on the first and second pulse wave signals PS1 and PS2 having the same waveform, so that the measurement accuracy of the pulse transit time can be further enhanced.

Figure 12:
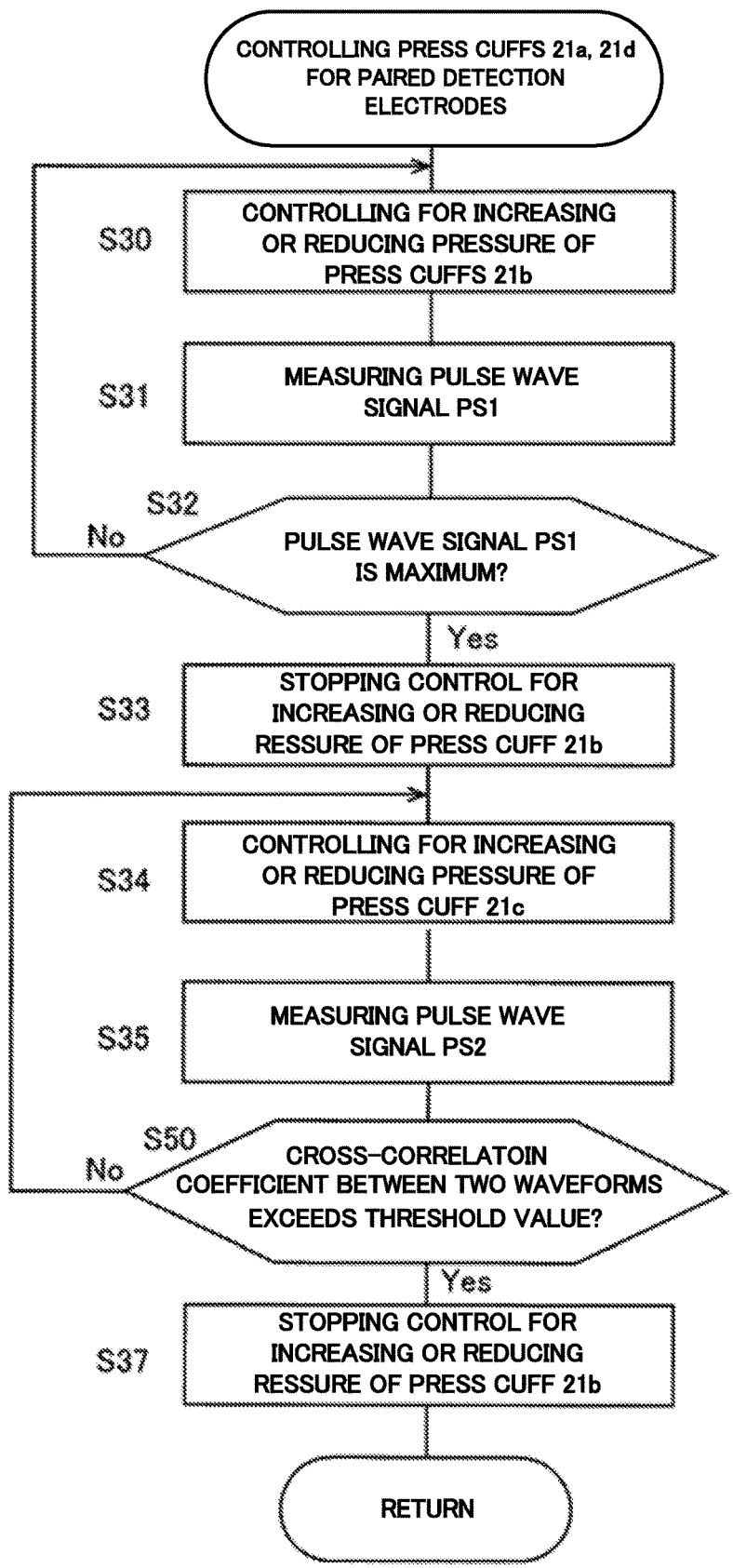
FIG. 12 is a diagram showing another example of the operation flow when the cuffs for the detection electrode pair shown in the operation flow of FIG. 8 are controlled.

FIG. 12 shows still another example of the operation flow when the sphygmomanometer 1 controls the press cuffs 21b and 21c. Whether the waveform of the second pulse wave signal PS2 and the waveform of the first pulse wave signal PS1 having the maximum amplitude are identical to each other is determined based on the amplitude of each of the respective waveforms in the operation flow of FIG. 10, or based on the respective upstroke times in the operation flow of FIG. 11. However, the determination is not limited to this manner. For example, as shown in step S50 in FIG. 12, the two waveforms may be determined to be identical to each other when the cross-correlation coefficient r between the two waveforms (see the equation Eq. 1 in FIG. 36) exceeds a threshold value.

Figure 13:
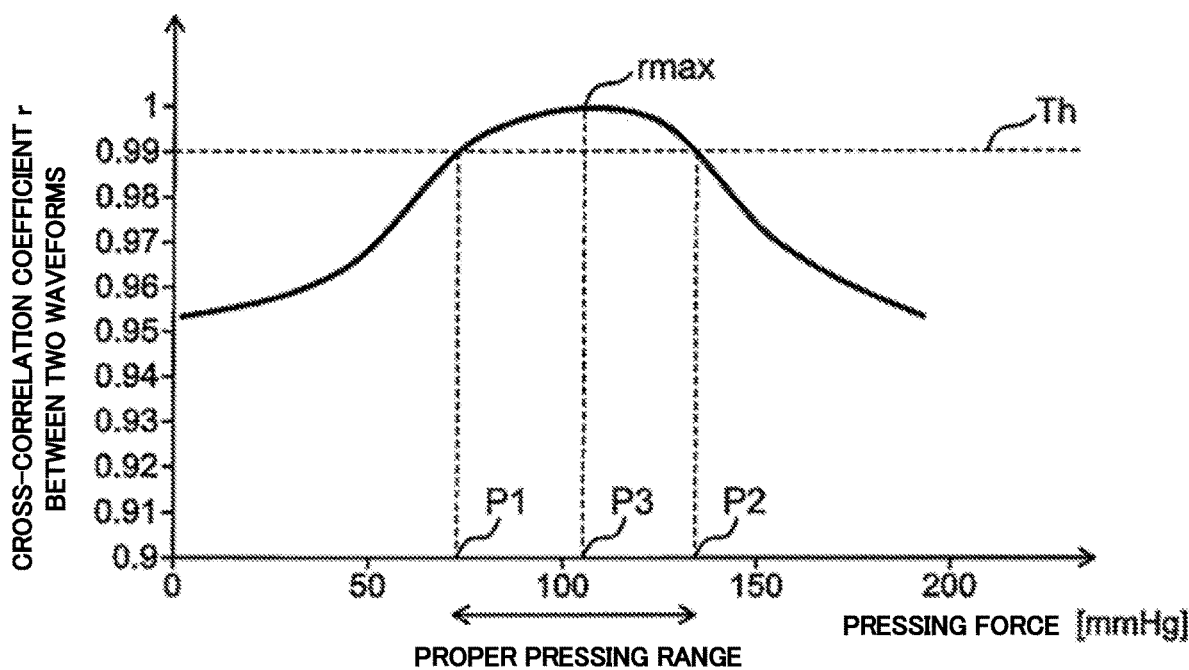
FIG. 13 is a diagram showing a relationship between pressing force on the paired detection electrodes and a cross-correlation coefficient between the waveforms of the first and second pulse wave signals output by the first and second pulse wave sensors, respectively.

The operation flow shown in FIG. 12 has been created based on the experimental results achieved by the inventors. That is, according to the experiments by the inventors, as shown in FIG. 13, it has been found that when the pressing forces of the first pulse wave sensor 40-1 (containing the paired first detection electrodes 42 and 43) and the second pulse wave sensor 40-2 (containing the paired second detection electrodes 44 and 45) against the left wrist 90 as the measurement target site (which are equal to the cuff pressures Pc by the press cuffs 21b and 21c) gradually increases from zero, the cross-correlation coefficient r between the waveforms of the first and second pulse wave signals PS1 and PS2 gradually increases in connection with the gradual increase of the pressing forces, exhibits a maximum value rmax, and then gradually decreases. This operation flow is based on an idea that a range in which the cross-correlation coefficient r exceeds a predetermined threshold value Th (in this example, Th=0.99) is an appropriate range of the pressing force (this is referred to as "proper pressing range"). In this example, the proper pressing range is a range of pressing force (cuff pressure Pc) from a lower limit value P1≅72 mmHg to an upper limit value P2≅135 mmHg.

As shown in FIG. 12, in this operation flow as well as the operation flows of FIGS. 10 and 11, the CPU 100 sets the cuff pressure Pc of the press cuff 21b while increasing or reducing the pressure of the press cuff 21b corresponding to the first pulse wave sensor 40-1 so that the amplitude of the first pulse wave signal PS1 becomes maximum (steps S30 to S33 in FIG. 12). In this example, the CPU 100 accumulates and records data necessary for calculation of the cross-correlation coefficient r in the memory 51 with respect to the first pulse wave signal PS1 having the maximum amplitude.

Next, the CPU 100 drives the pump 32c via the pump drive circuit 320c to increase the pressure of the press cuff 21c corresponding to the second pulse wave sensor 40-2 (step S34 in FIG. 12). In this pressure-increasing step, the CPU 100 acquires the second pulse wave signal PS2 which is time-sequentially output by the second pulse wave sensor 40-2 (step S35 in FIG. 12), calculates the cross-correspondence coefficient r between the waveforms of the first and second pulse wave signals PS1 and PS2 in real time based on the acquired data and the data of the first pulse wave signal PS1 accumulated and recorded in the memory 51, and determines whether the calculated cross-correlation coefficient r exceeds the predetermined threshold value Th (=0.99) (step S50 in FIG. 12).

Here, when the cross-correlation coefficient r is equal to or less than the threshold value Th (NO in step S50 in FIG. 12), the processing of steps S34 to S50 is repeated until the cross-correlation coefficient r exceeds the threshold value Th unless the cuff pressure Pc has reached an upper limit pressure (which is predetermined to, for example, 300 mmHg for safety). When the cross-correlation coefficient r exceeds the threshold value Th (YES in step S50 in FIG. 12), the CPU 100 stops the pump 32c (step S37 in FIG. 12), and sets the cuff pressure Pc of the press cuff 21c to a value at that time, that is, a value at the time when the cross-correlation coefficient r exceeds the threshold value Th. In this example, the cuff pressure Pc is set to the value at the time point when the cross-correlation coefficient r exceeds the threshold value Th, that is, P1 (≅72 mmHg) shown in FIG. 13.

In this case, the pulse transit time is measured based on the first and second pulse wave signals PS1 and PS2 having the same waveform, so that the measurement accuracy of the pulse transit time can be further enhanced. In addition, the cuff pressure Pc is set to a value at the time point when the cross-correlation coefficient r exceeds the threshold value Th, so that the pulse transit time can be acquired without needlessly increasing the cuff pressure Pc. As a result, the physical burden on the user can be reduced.

(Verification of Effect by Setting of Pressing Force)

Figure 14A:
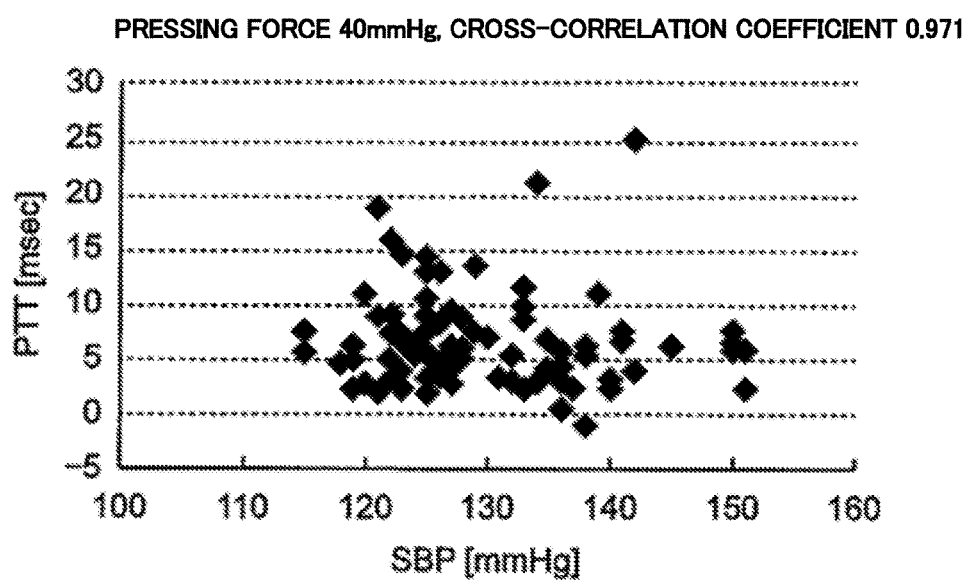
FIG. 14A is a scatter diagram showing a relationship between a pulse transit time (PTT) acquired under a condition in which pressing force (cuff pressure) was set to 40 mmHg by the sphygmomanometer and a systolic blood pressure (SBP) acquired by blood pressure measurement based on an oscillometric method for various users (subjects).

A scatter diagram of FIG. 14A shows the relationship between the pulse transit time (PTT) acquired under a condition that the pressing force (cuff pressure Pc) is set to 40 mmHg (less than the lower limit value P1 shown in FIG. 13) by the sphygmomanometer 1 and the systolic blood pressure (SBP) acquired by the blood pressure measurement based on the oscillometric method (step S5 in FIG. 6) for various users (subjects). The cross-correlation coefficient r between the waveforms of the first and second pulse wave signals PS1 and PS2 under the pressing force setting condition described above was equal to 0.971, which was lower than the threshold value Th (=0.99). As can be seen from FIG. 14A, there is almost no correlation between pulse transit time (PTT) and the systolic blood pressure (SBP). When fitting was performed by using the equation (Eq. 2) in FIG. 32 to calculate the correlation coefficient, the correlation coefficient was equal to −0.07.

Figure 14B:
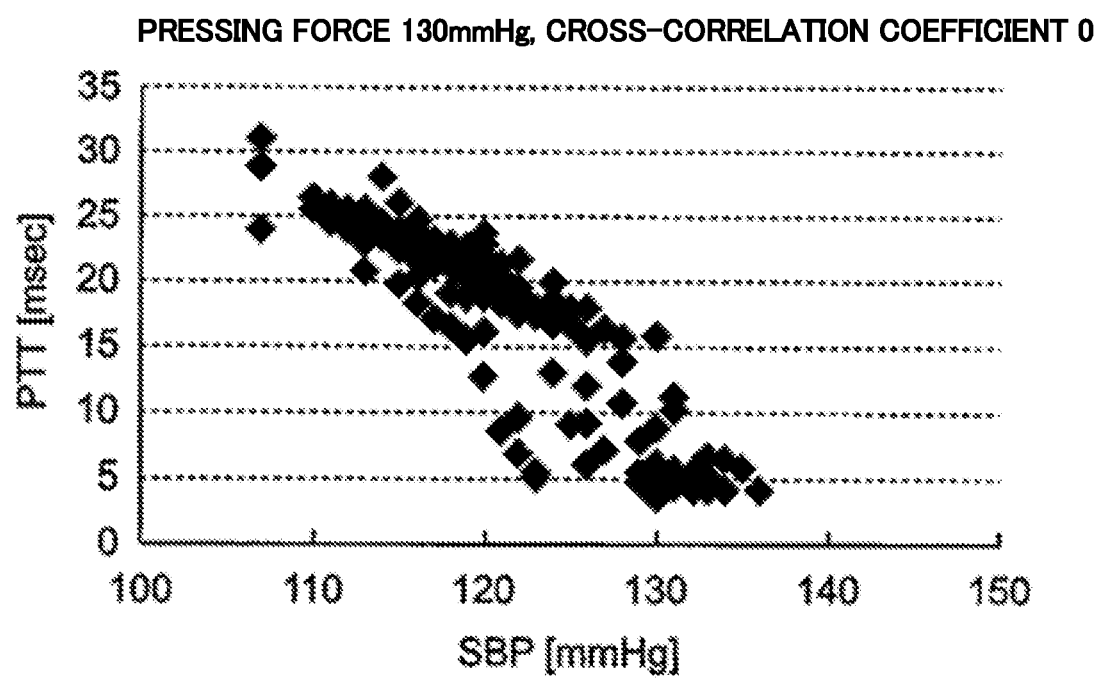
FIG. 14B is a scatter diagram showing a relationship between a pulse transit time (PTT) acquired under a condition in which pressing force (cuff pressure) was set to 130 mmHg by the sphygmomanometer and a systolic blood pressure (SBP) acquired by blood pressure measurement based on the oscillometric method for various users.

On the other hand, a scatter diagram of FIG. 14B shows the relationship between the pulse transit time (PTT) acquired under a condition that the pressing force (cuff pressure Pc) is set to 130 mmHg (within a proper pressing range between the lower limit value P1 and the upper limit value P2 shown in FIG. 13) by the sphygmomanometer 1, and the systolic blood pressure (SBP) acquired by the blood pressure measurement based on the oscillometric method (step S5 in FIG. 6) for the above various users. The cross-correlation coefficient r between the waveforms of the first and second pulse wave signals PS1 and PS2 under the above pressing force setting condition was equal to 0.9901, which exceeded the threshold value Th (=0.99). As can be seen from FIG. 14B, the correlation between the pulse transit time (PTT) and the systolic blood pressure (SBP) is strong. When fitting was performed by using the equation (Eq. 2) in FIG. 32 to calculate the correlation coefficient, the correlation coefficient was equal to −0.90.

According to the results of FIGS. 14A and 14B, it could be verified that the correlation between the pulse transit time (PTT) and the systolic blood pressure (SBP) could be enhanced by setting the pressing force (cuff pressure Pc) to a value at which the cross-correlation coefficient r exceeds the threshold value Th (=0.99) and acquiring the pulse transit time (PTT). It is considered that the correlation between the pulse transit time (PTT) and the systolic blood pressure (SBP) is thus enhanced because the measurement accuracy of the pulse transit time (PTT) is enhanced by setting the pressing force according to the present invention. As a result, the measurement accuracy of blood pressure can be enhanced.

Second Embodiment

Next, a second embodiment of the blood pressure measurement device including the pulse wave measurement device of the present invention will be described in detail with reference to the drawings. The description of the same parts as those in the first embodiment will be omitted.

(Configuration of Sphygmomanometer)

Figure 15:
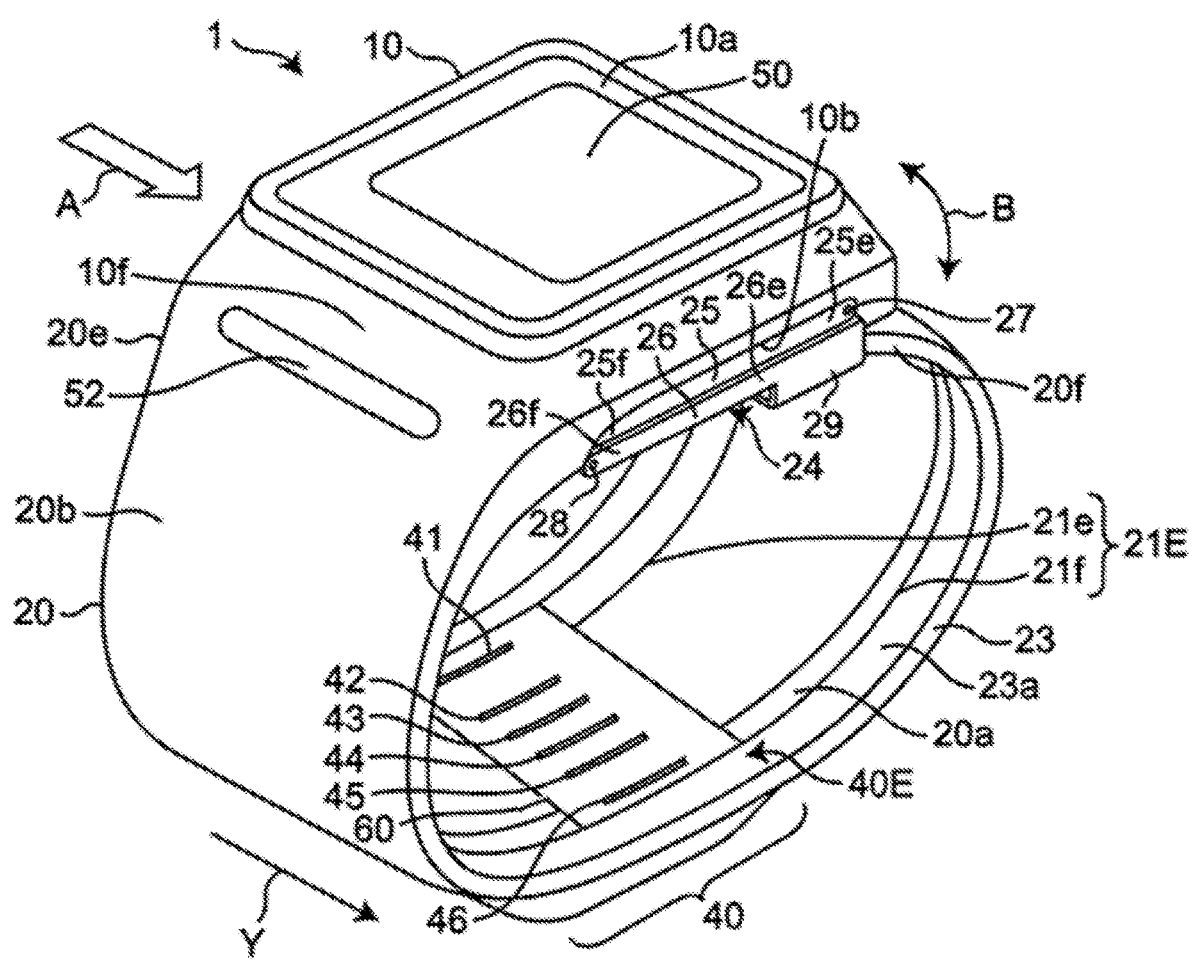
FIG. 15 is a perspective view showing an appearance of a wrist type sphygmomanometer according to a second embodiment according to the blood pressure measurement device including the pulse wave measurement device of the present invention.
Figure 16:
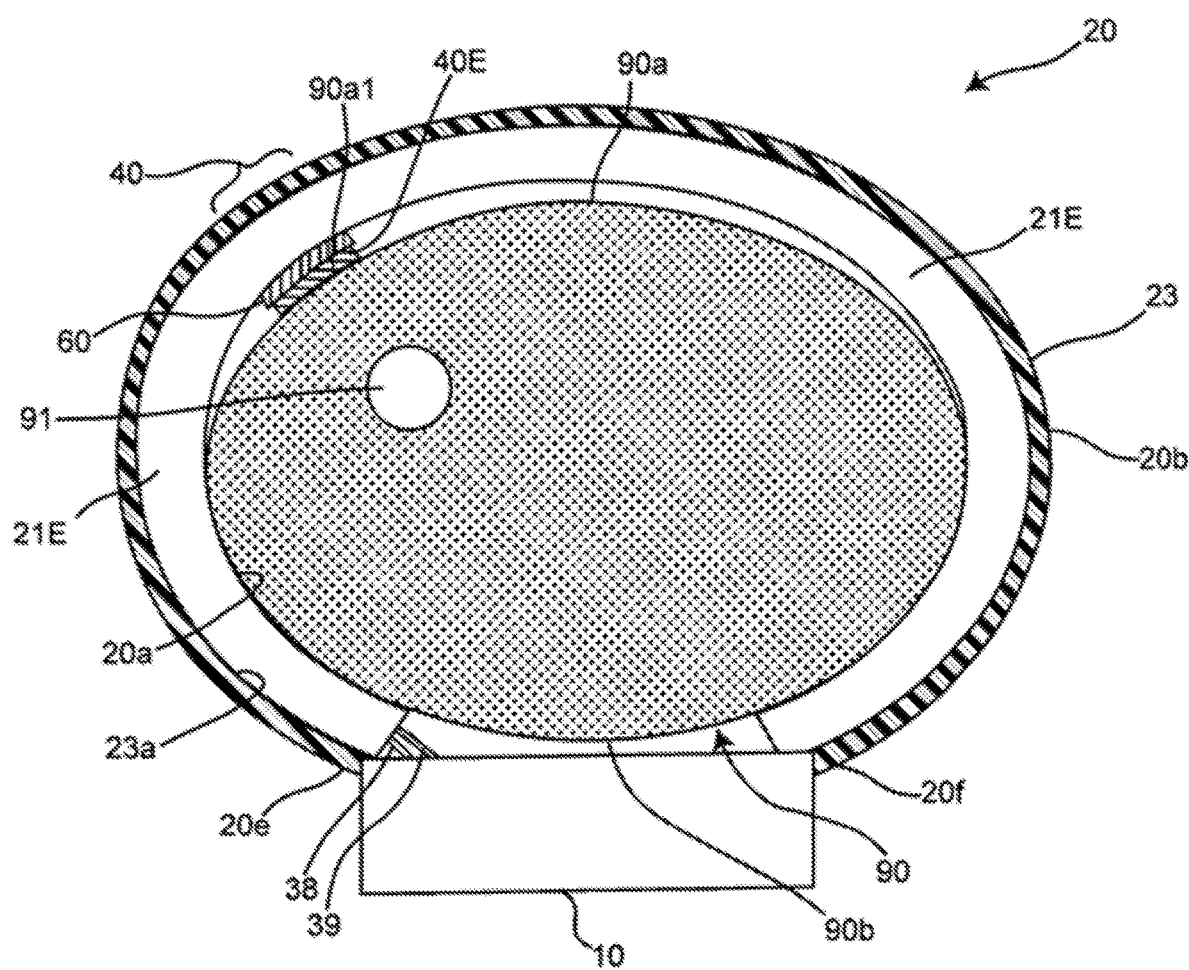
FIG. 16 is a diagram schematically showing a cross-section perpendicular to the longitudinal direction of the wrist in a state where the sphygmomanometer shown in FIG. 15 is worn on the left wrist.

FIG. 15 shows an appearance of the sphygmomanometer 1 according to the second embodiment when the sphygmomanometer 1 is viewed from an oblique side. FIG. 16 schematically shows a cross-section perpendicular to the longitudinal direction of the left wrist 90 in a state where the sphygmomanometer 1 is worn on the left wrist 90 as the measurement target site.

As well understood from FIG. 15, the press cuff group 21E working as the pressing unit in the second embodiment is divided with respect to the width direction Y of the belt 20, and includes a press cuff 21e as a fifth pressing member and a press cuff 21f as a sixth pressing member. A solid 60 is provided at positions corresponding to the impedance measurement unit 40 on the inner peripheral surfaces 20a of the press cuffs 21e and 21f (the belt 20). In this example, the solid 60 is made of plate-like resin (in this example, ABS) having a thickness of about 7 mm. An electrode group 40E is provided on the inner peripheral surface of the solid 60.

In this example, the press cuff group 21E is also configured as a fluid bag by confronting two stretchable polyurethane sheets in the thickness direction and welding the peripheral edge portions thereof. As shown in FIG. 16, the solid 60 is arranged on a site of the inner peripheral surface 20a of the press cuff group 21E (belt 20) which meets the radial artery 91 of the left wrist 90, and the electrode group 40E of the impedance measurement unit 40 is arranged on the inner peripheral surface of the solid 60.

Figure 17:
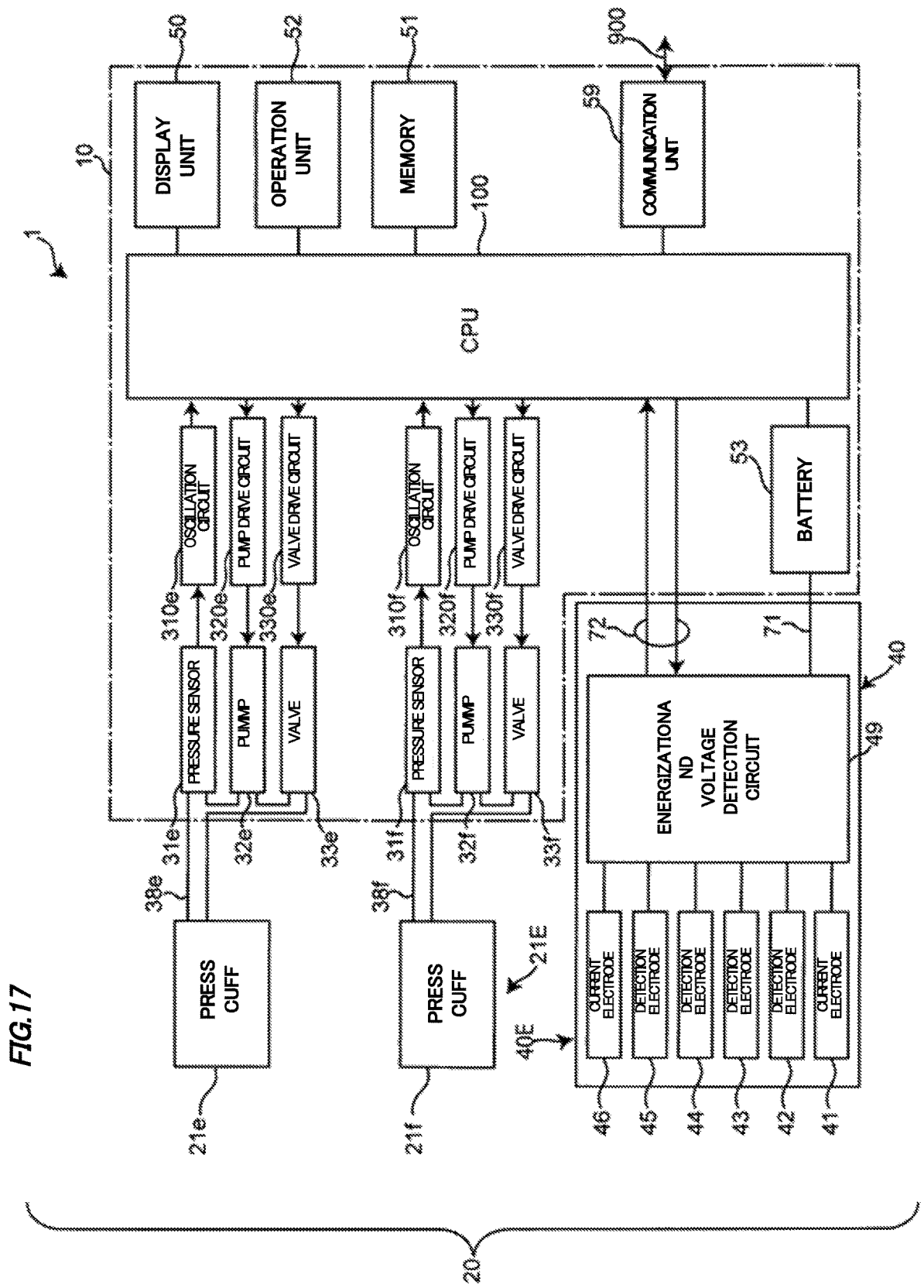
FIG. 17 is a diagram showing a block configuration of a control system of the sphygmomanometer shown in FIG. 15.

FIG. 17 shows a block configuration of a control system of the sphygmomanometer 1 in the second embodiment. Like the sphygmomanometer 1 of the first embodiment, in addition to the display unit 50 and the operation unit 52, the CPU 100 as the control unit, the memory 51 as the storage unit, and the communication unit 59 are mounted in the main body 10 of the sphygmomanometer 1. In the main body 10 are also mounted pressure sensors 31e and 31f, pumps 32e and 32f, and valves 33e and 33f (note that in the following description, these units may be collectively referred to as the pressure sensor 31, the pump 32, and the valve 33). Furthermore, in the main body 10 are mounted oscillation circuits 310e and 310f for converting outputs from the pressure sensors 31e and 31f into frequencies, pump drive circuits 320e and 320f for driving the pumps 32e and 32f respectively, and valve drive circuits 330e and 330f for driving the valves 33e and 33f respectively (note that in the following description, these units may be collectively referred to as the oscillation circuit 310, the pump drive circuit 320, and the valve drive circuit 330.). In this example, a piezoresistive pressure sensor is also used as the pressure sensor 31, and it is connected to the pump 32, the valve 33 and the press cuff group 21E through the air pipe 38 (38e, 38f).

Figure 18A:
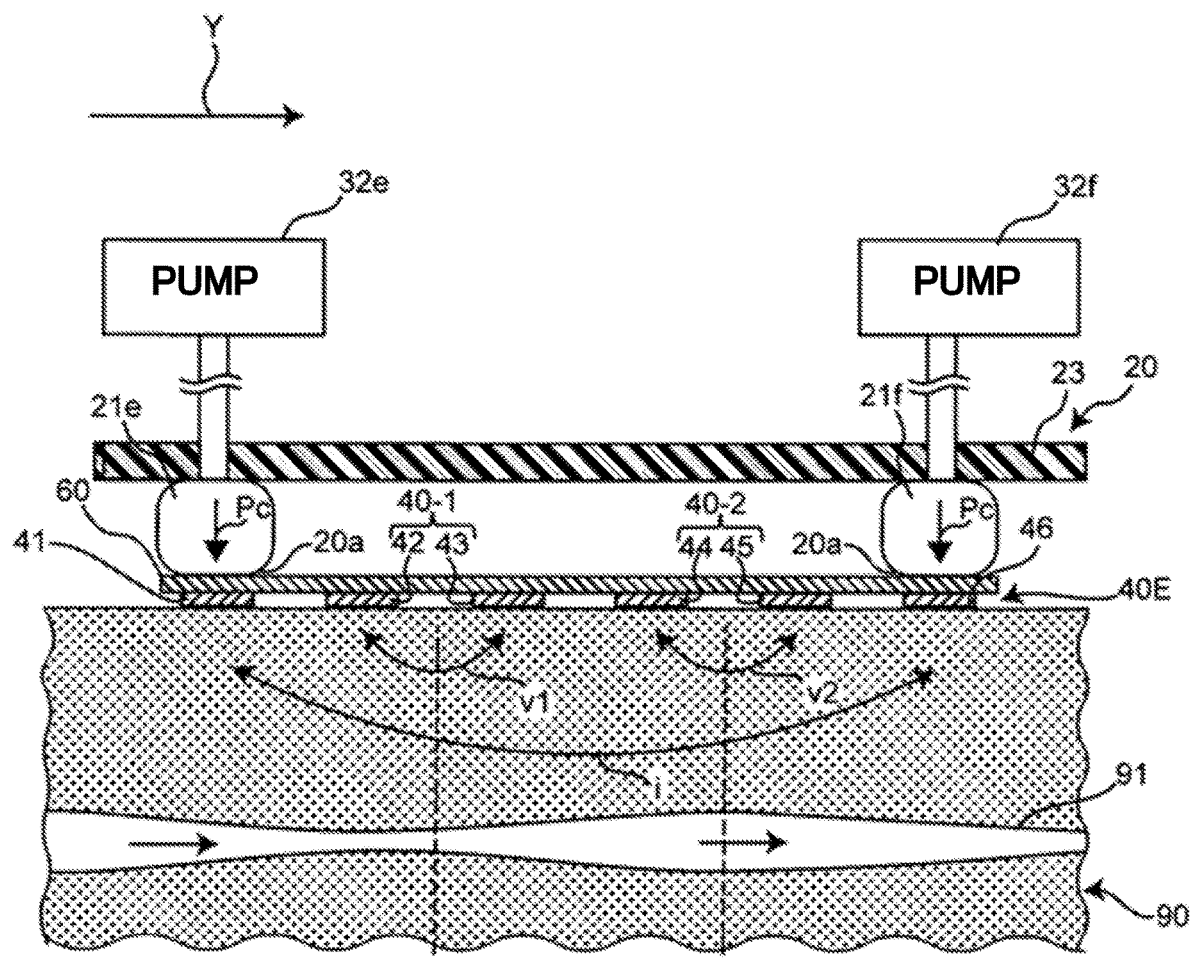
FIG. 18A is a diagram schematically showing a cross-section along the longitudinal direction of the wrist in a state where the sphygmomanometer shown in FIG. 15 is worn on the left wrist.
Figure 18B:
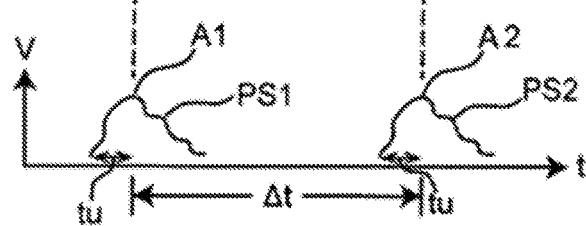
FIG. 18B is a diagram showing waveforms of first and second pulse wave signals output from the first and second pulse wave sensors, respectively.

FIG. 18A schematically shows a cross-section along the longitudinal direction of the wrist in a state where the sphygmomanometer 1 is worn on the left wrist 90. FIG. 18B shows the waveforms of the first pulse wave signal PS1 and the second pulse wave signal PS2 which are output by the first pulse wave sensor 40-1 and the second pulse wave sensor 40-2, respectively. As shown in FIG. 18A, the solid 60 as a solid material is arranged across the first pulse wave sensor 40-1 and the second pulse wave sensor 40-2 with respect to the artery direction of the radial artery 91. The press cuff 21e constituting the fifth pressing member and the press cuff 21f constituting the sixth pressing member are provided at positions where the press cuff 21e and the press cuff 21f respectively press outer portions of the solid 60 than the first pulse wave sensor 40-1 and the second pulse wave sensor 40-2 with respect to the arterial direction. In this example, the press cuffs 21e and 21f are provided at positions corresponding to the paired current electrodes 41 and 46. Therefore, when the press cuffs 21e and 21f are pressurized by the pumps 32e and 32f, the press cuffs 21e and 21f press the solid 60, and the solid 60 presses the paired current electrodes 41 and 46, the first pulse wave sensor 40-1, and the second pulse wave sensor 40-2 against the palmar side surface 90a of the left wrist 90. In this example, the pumps 32e and 32f can independently pressurize the press cuffs 21e and 21f under the control of the CPU 100. Accordingly, the pressing forces of the paired current electrodes 41 and 46, the first pulse wave sensor 40-1, and the second pulse wave sensor 40-2 against the palmar side surface 90a of the left wrist 90 can be set to a proper value so as to follow a certain pressure gradient.

(Operation of Blood Pressure Measurement by Oscillometric Method)

The blood pressure measurement by the oscillometric method in the sphygmomanometer 1 according to the second embodiment is performed according to the operation flow shown in FIG. 6 as in the case of the first embodiment.

When the CPU 100 exhausts the air in the press cuff group 21E (step S2 in FIG. 6), the CPU 100 performs control of exhaust on the press cuffs 21e and 21f. Furthermore, when the CPU 100 gradually increases the cuff pressure Pc of the press cuff group 21E, the CPU 100 performs control of increase of pressure on the press cuffs 21e and 21f. When the CPU 100 calculates the blood pressure value (steps S3 to S5 in FIG. 6), the cuff pressures Pc of both the press cuffs 21e and 21f may be monitored to calculate an average thereof, or the cuff pressure Pc of any one of the press cuffs 21e and 21f may be monitored. The other control in the operation flow of FIG. 6 is similar to the control of the first embodiment, and thus the description thereof is omitted. Note that in this example, the calculation of the blood pressure value is not limitedly performed in the pressure-increasing step, but may be performed in the pressure-reducing step.

(Operation of Blood Pressure Measurement Based on Pulse Transit Time)

Figure 19:
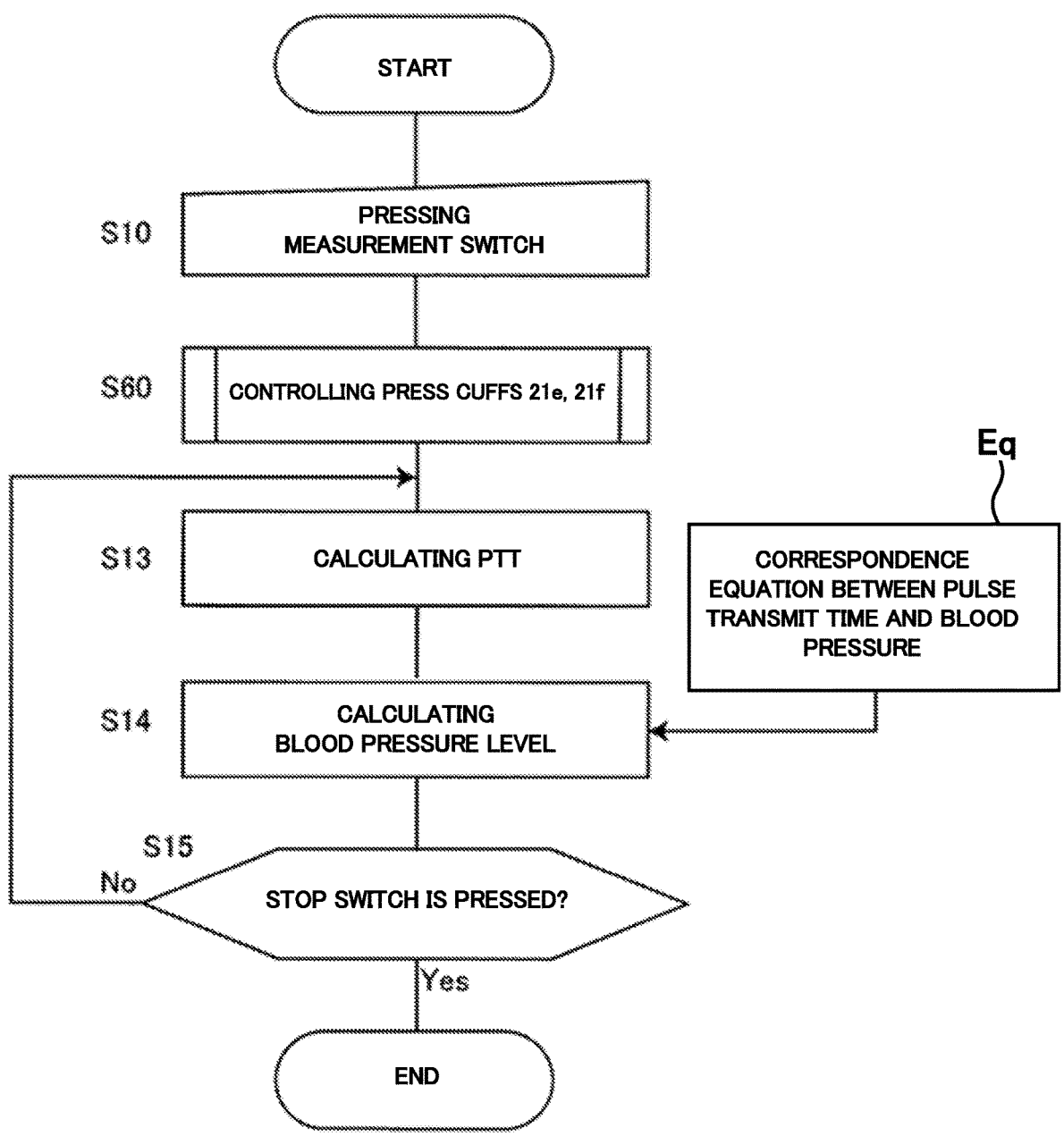
FIG. 19 is a diagram showing an operation flow when the sphygmomanometer executes the pulse wave measurement method according to an embodiment to acquire a pulse transit time (PTT) and performs blood pressure measurement (estimation) based on the pulse transit time.

FIG. 19 shows an operation flow when the sphygmomanometer 1 of the second embodiment performs the blood pressure measurement (estimation) based on the pulse transit time.

Figure 20:
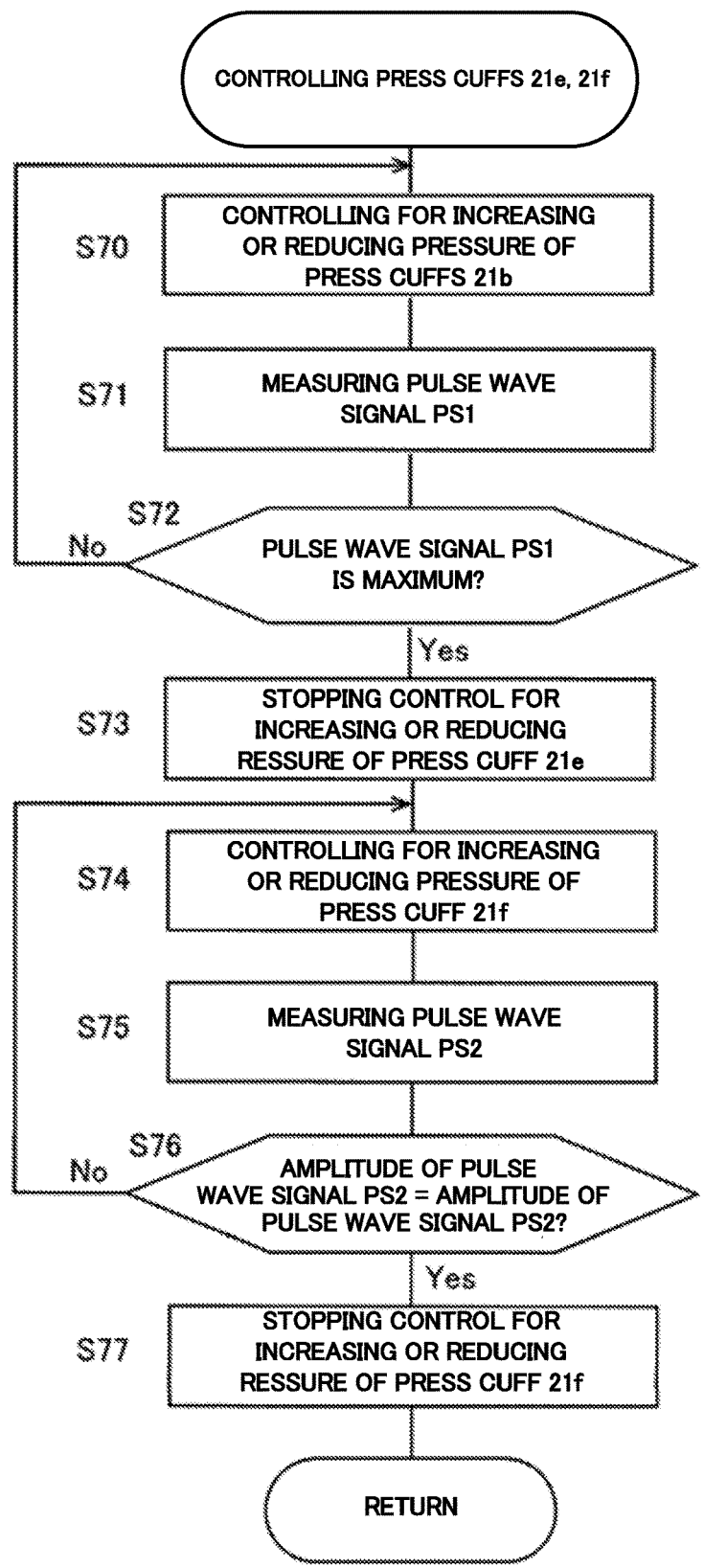
FIG. 20 is a diagram showing an example of an operation flow when cuffs for a detection electrode pair shown in the operation flow of FIG. 19 is controlled.

In the second embodiment, as shown in FIG. 19, when the user instructs the blood pressure measurement based on PTT with the push type switch as the operation unit 52 provided in the main body 10 (step S10 in FIG. 19), the CPU 100 works as a pulse wave sensor pressing force setting unit to start control of the press cuffs 21e and 21f (step S60 in FIG. 19). FIG. 20 shows an operation flow when the sphygmomanometer 1 controls the press cuffs 21e and 21f.

An operation flow shown in FIG. 20 has been created based on the experimental results achieved by the inventors. According to the experiments by the inventors, it has been found that when the pressing forces of the first pulse wave sensor 40-1 and the second pulse wave sensor 40-2 against the left wrist 90 as the measurement target site are set to different values so as to follow a certain pressure gradient, it is easier to achieve a state in which the waveforms of the first pulse wave signal PS1 and the second pulse wave signal PS2 are identical to each other. It has been also found that the pressure gradient is different among users. It is considered that this is based on the fact that living tissues in the left wrist 90 as the measurement target site are different among users. This operation flow is based on an idea that the pressing forces of the first pulse wave sensor 40-1 and the second pulse wave sensor 40-2 are set to different values so as to follow a certain pressure gradient by changing the respective cuff pressures Pc of the press cuffs 21e and 21f to press the first pulse wave sensor 40-1 and the second pulse wave sensor 40-2 via the solid 60, thereby acquiring the same waveform as the waveforms of the first pulse wave signal PS1 and the second pulse wave signal PS2.

As shown in FIG. 20, when control of the press cuffs 21e and 21f is started, the CPU 100 works as a pulse wave sensor pressing force setting unit to close the valve 33e via the valve drive circuit 330e, drives the pump 32e via the pump drive circuit 320e and increase the pressure of the press cuff 21e (step S70 in FIG. 20). In this example, the cuff pressure Pc of the press cuff 21e is continuously increased at a constant speed (=5 mmHg/s). As a result, the press cuff 21e presses the solid 60, and the solid 60 presses the current electrode 41 and the first pulse wave sensor 40-1.

In this pressure-increasing step, the CPU 100 acquires the first pulse wave signal PS1 which is time-sequentially output by the first pulse wave sensor 40-1 (step S71 in FIG. 20), and also the CPU 100 determines whether the amplitude of the acquired first pulse wave signal PS1 is the maximum (step S72 in FIG. 20).

When the amplitude of the first pulse wave signal PS1 is not maximum (NO in step S72 in FIG. 20), the CPU 100 drives or stops the pump 32e via the pump drive circuit 320e, or opens or closes the valve 33e via the valve drive circuit 330e to increase or reduce the pressure of the press cuff 21e (step S70 in FIG. 20). The processing of steps S70 to S72 is repeated until the amplitude of the first pulse wave signal PS1 becomes maximum unless the cuff pressure Pc has reached the upper limit pressure (which is predetermined to, for example, 300 mmHg for safety). Note that as in the case of the first embodiment, not only increase of the pressure of the press cuff 21e, but also reduction of the pressure of the press cuff 21e is performed because when the pressing force is increased even after the amplitude of the first pulse wave signal PS1 exhibits a maximum value, there is a tendency that blood vessels collapse and the amplitude of the first pulse wave signal PS1 gradually decreases. Therefore, in this example, not only the increase of the pressure of the press cuff 21e, but also the reduction of the pressure of the press cuff 21e is performed to acquire the cuff pressure Pc at which the amplitude of the first pulse wave signal PS1 becomes maximum.

When the amplitude becomes maximum (YES in step S72 in FIG. 20), the CPU 100 stops the pump 32e (step S73 in FIG. 20), and sets the cuff pressure Pc of the press cuff 21e to a value at that time point, that is, a value at the time point when the amplitude of the first pulse wave signal PS1 becomes maximum.

Next, the CPU 100 closes the valve 33f via the valve drive circuit 330f and drives the pump 32f via the pump drive circuit 320f to increase the pressure of the press cuff 21f (step S74 in FIG. 20). In this example, the cuff pressure Pc of the press cuff 21f is continuously increased at a constant speed (=5 mmHg/s). As a result, the press cuff 21f presses the solid 60, and the solid 60 presses the current electrode 46 and the second pulse wave sensor 40-2. In addition, since the solid 60 also presses the current electrode 41 and the first pulse wave sensor 40-1, a pressure gradient occurs between the pressing force of the first pulse wave sensor 40-1 and the pressing force of the second pulse wave sensor 40-2.

In this pressure-increasing step, the CPU 100 acquires the second pulse wave signal PS2 which is time-sequentially output by the second pulse wave sensor 40-2 (step S75 in FIG. 20), and also the CPU 100 works as a waveform comparing unit to determine whether the amplitude of the acquired second pulse wave signal PS2 and the maximum amplitude of the first pulse wave signal PS1 set as described above are identical to each other (step S37 in FIG. 20). Note that in this example, an allowable range when "identical" is determined is set to a range of ±10%.

When the amplitude of the second pulse wave signal PS2 is not maximum (NO in step S76 in FIG. 20), the CPU 100 drives or stops the pump 32f via the pump drive circuit 320f, or opens or closes the valve 33f via the valve drive circuit 330f to increase or reduce the pressure of the press cuff 21f (step S74 in FIG. 20). The processing of steps S74 to S76 is repeated until the amplitude of the second pulse wave signal PS2 becomes equal to the maximum amplitude of the first pulse wave signal PS1 unless the cuff pressure Pc has reached the upper limit pressure (which is predetermined to, for example, 300 mmHg for safety). Note that not only increase of the pressure of the press cuff 21f, but also reduction of the pressure of the press cuff 21f is performed because the relationship between the amplitude of the second pulse wave signal PS2 and the pressing force is also similar to the relationship between the amplitude of the first pulse wave signal PS1 and the pressing force described above.

When the amplitude of the second pulse wave signal PS2 becomes equal to the maximum amplitude of the first pulse wave signal PS1 (YES in step S76 in FIG. 20), the CPU 100 stops the pump 32f (step S77 in FIG. 20), and sets the cuff pressure Pc of the press cuff 21f to a value at that time point, that is, a value at the time point when the amplitude of the second pulse wave signal PS2 becomes equal to the maximum amplitude of the first pulse wave signal PS1. The control of the press cuffs 21e and 21f (step S60 in FIG. 19) is terminated with the operation flow described above.

Under this state, the CPU 100 works as a measurement processing unit to acquire the time difference Δt (see FIG. 5B) between the first and second pulse wave signals PS1 and PS2 as a pulse transit time (PTT) (step S14 in FIG. 19). More specifically, in this example, the time difference Δt between the peak A1 of the first pulse wave signal PS1 and the peak A2 of the second pulse wave signal PS2 is acquired as the pulse transit time (PTT).

In this case, since the pulse transit time is measured based on the first and second pulse wave signals PS1 and PS2 having the same waveform, the measurement accuracy of the pulse transit time can be enhanced. Furthermore, the pulse transit time can be acquired without needlessly increasing the cuff pressure Pc. As a result, the physical burden on the user can be reduced.

Next, the CPU 100 works as a first blood pressure calculation unit, and uses a predetermined correspondence equation Eq between the pulse transit time and the blood pressure to calculate (estimate) the blood pressure based on the pulse transit time (PTT) acquired in step S13 (step S14 in FIG. 19). Here, as in the case of the first embodiment, the predetermined correspondence equation Eq between the pulse transit time and the blood pressure is provided, for example, as a publicly-known fractional function including a term of $1/DT^2$ as indicated by the equation (Eq. 2) in FIG. 32.

When the blood pressure is calculated (estimated) as described above, the measurement accuracy of the blood pressure can be enhanced because the measurement accuracy of the pulse transit time is enhanced as described above. Note that the measurement result of the blood pressure value is displayed on the display unit 50 and recorded in the memory 51.

In this example, when stop of measurement is not instructed by the push type switch as the operation unit 52 in step S15 in FIG. 19 (NO in step S15 in FIG. 19), calculation of the pulse transit time (PTT) (Step S13 in FIG. 19) and calculation (estimation) of the blood pressure (step S14 in FIG. 19) are periodically repeated every time the first and second pulse wave signals PS1 and PS2 are input according to the pulse wave. The CPU 100 updates and displays the measurement result of the blood pressure value on the display unit 50, and accumulates and records the measurement result in the memory 51. When stop of measurement is instructed in step S15 in FIG. 19 (YES in step S15 in FIG. 19), the CPU 100 performs control to open the valves 33e and 33f via the valve drive circuits 330e and 330f and exhaust the air in the press cuffs 21e and 21f, and then terminates the measurement operation.

According to the sphygmomanometer 1, blood pressure can be continuously measured over a long period of time by the blood pressure measurement based on the pulse transit time (PTT) with a light physical burden on users.

According to the sphygmomanometer 1, the blood pressure measurement (estimation) based on the pulse transit time and the blood pressure measurement by the oscillometric method can be performed by an integrated device. Therefore, the convenience of the users can be enhanced.

According to the sphygmomanometer 1, as compared with the first embodiment, the press cuff, the pressure sensor, the oscillation circuit, the pump, the pump drive circuit, the valve, and the valve drive circuit can be reduced, so that the configuration can be simplified.

(Second Modification)

Figure 21:
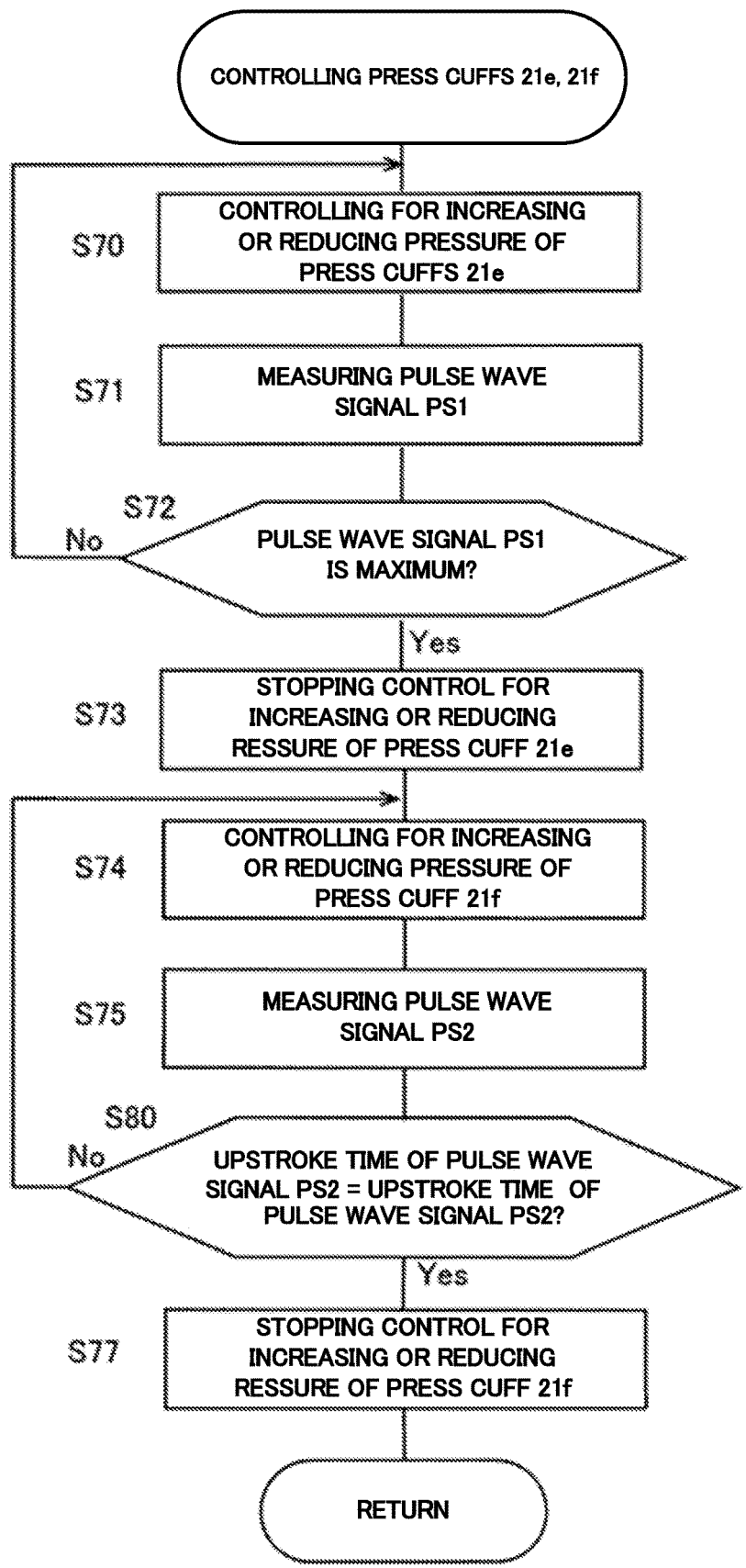
FIG. 21 is a view showing another example of the operation flow when the cuffs for the detection electrode pair shown in the operation flow of FIG. 19 is controlled.

FIG. 21 shows another example of the operation flow when the sphygmomanometer 1 controls the press cuffs 21e and 21f. In the example shown in FIG. 20, whether the waveform of the second pulse wave signal PS2 and the waveform of the first pulse wave signal PS1 having the maximum amplitude are identical to each other based on the amplitude of each waveform in step S76. However, the determination is not limited to this manner. For example, as shown in step S80 in FIG. 21, whether the respective waveforms are the same is determined based on whether the upstroke time of the second pulse wave signal PS2 is equal to the upstroke time of the first pulse wave signal PS1 having the maximum amplitude.

As shown in FIG. 21, in this operation flow as well as the operation flow of FIG. 20, the CPU 100 sets the cuff pressure Pc of the press cuff 21e so that the amplitude of the first pulse wave signal PS1 becomes maximum while increasing or reducing the pressure of the press cuff 21e (steps S70 to S72 in FIG. 21). In this case, when the CPU 100 determines that the amplitude of the first pulse wave signal PS1 is maximum in the operation flow of FIG. 21 (YES in step S72 in FIG. 21), the CPU 100 records the upstroke time tu of the first pulse wave signal PS1 in the memory 51. In this example, an allowable range when it is determined that the upstroke times are "identical" is set to a range of ±1%.

Next, the CPU 100 closes the valve 33f via the valve drive circuit 330f, and drives the pump 32f via the pump drive circuit 320f to increase the pressure of the press cuff 21f corresponding to the second pulse wave sensor 40-2 (step S74 in FIG. 21). In this pressure-increasing step, the CPU 100 acquires the second pulse wave signal PS2 which is time-sequentially output by the second pulse wave sensor 40-2 (step S75 in FIG. 21), and also the CPU 100 works as the waveform comparing unit to determine whether the upstroke time tu of the acquired second pulse wave signal PS2 is identical to the upstroke time tu of the first pulse wave signal PS1 recorded in the memory 51 (step S80 in FIG. 21). Note that in this example, an allowable range when it is determined that the upstroke times tu are "identical" is set to a range of ±1%.

Here, when the upstroke time tu of the second pulse wave signal PS2 and the upstroke time tu of the first pulse wave signal PS1 are not identical to each other (NO in step S80 in FIG. 21), the processing of steps S74 to S80 is repeated until the upstroke times tu are identical to each other unless the cuff pressure Pc has reached the upper limit pressure (which is predetermined to, for example, 300 mmHg for safety). When the upstroke times tu become equal to each other (YES in step S80 in FIG. 21), the CPU 100 stops the pump 32f (step S77 in FIG. 21), and sets the cuff pressure Pc of the press cuff 21f to a value at that time point, that is, a value at the time point when the upstroke times tu are equal to each other. As a result, since the pulse transit time is measured based on the first and second pulse wave signals PS1 and PS2 which have the same waveform, the measurement accuracy of the pulse transit time can be further enhanced.

Figure 22:
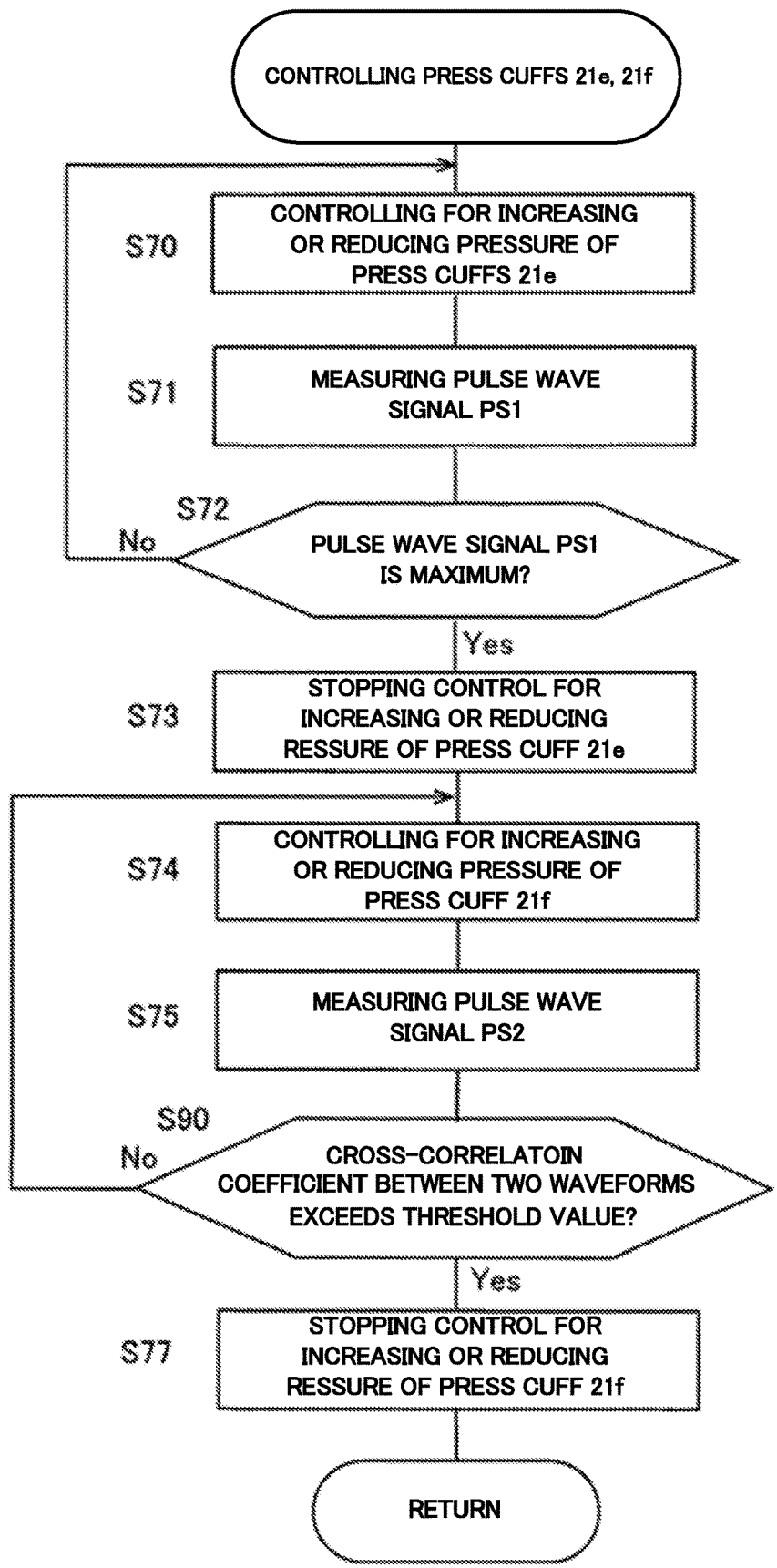
FIG. 22 is a diagram showing another example of the operation flow when the cuffs for the detection electrode pair shown in the operation flow of FIG. 19 is controlled.

FIG. 22 shows still another example of the operation flow when the sphygmomanometer 1 controls the press cuffs 21e and 21f. Whether the waveform of the second pulse wave signal PS2 and the waveform of the first pulse wave signal PS1 having the maximum amplitude are identical to each other is determined based on the amplitude of each waveform in the operation flow of FIG. 20 or based on each upstroke time in the operation flow of FIG. 21. However, the determination is not limited to this manner. For example, as shown in step S90 in FIG. 22, it may be determined that the two waveforms are identical to each other when the cross-correlation coefficient r between the two waveforms (see the equation Eq. 1 in FIG. 36) exceeds a threshold value.

The operation flow shown in FIG. 22 is also based on an idea that the range in which the cross-correlation coefficient r exceeds the predetermined threshold value Th (Th=0.99 in this example) is a proper pressing range. In this example, the proper pressing range is set to a range in which the pressing force (cuff pressure Pc) ranges from the lower limit value P1≅72 mmHg to the upper limit value P2≅135 mmHg.

As shown in FIG. 22, in this operation flow as well as the operation flow in FIGS. 20 and 21, the CPU 100 sets the cuff pressure Pc of the press cuff 21e so that the amplitude of the first pulse wave signal PS1 becomes maximum while increasing or reducing the pressure of the press cuff 21e corresponding to the first pulse wave sensor 40-1 (steps S70 to S73 in FIG. 22). Note that in this example, the CPU 100 accumulates and records data necessary for calculation of the cross-correlation coefficient r in the memory 51 for the first pulse wave signal PS1 having the maximum amplitude.

Next, the CPU 100 closes the valve 33f via the valve drive circuit 330f, and drives the pump 32f via the pump drive circuit 320f to increase the pressure of the press cuff 21f corresponding to the second pulse wave sensor 40-2 (step S74 in FIG. 22). In this pressure-increasing step, the CPU 100 acquires the second pulse wave signal PS2 which is time-sequentially output by the second pulse wave sensor 40-2 (step S75 in FIG. 22), calculates the cross-correlation coefficient r between the waveforms of the first and second pulse wave signals PS1 and PS2 in real time based on the acquired data and the data of the first pulse wave signal PS1 accumulated and recorded in the memory 51, and determines whether the calculated cross-correlation coefficient r exceeds the predetermined threshold value Th (=0.99) (step S90 in FIG. 22).

Here, when the cross-correlation coefficient r is not more than the threshold value Th (NO in step S90 in FIG. 22), the processing of steps S74 to S90 is repeated until the cross-correlation coefficient r exceeds the threshold value Th unless the cuff pressure Pc has reached the upper limit pressure (which is predetermined to, for example, 300 mmHg for safety). When the cross-correlation coefficient r exceeds the threshold value Th (YES in step S90 in FIG. 22), the CPU 100 stops the pump 32f (step S77 in FIG. 22), and sets the cuff pressure Pc of the press cuff 21f to a value at the time point, that is, a value at the time point when the cross-correlation coefficient r exceeds the threshold value Th. In this example, the cuff pressure Pc is set to a value at the time point when the cross-correlation coefficient r exceeds the threshold value Th, that is, P1 (72 mmHg) shown in FIG. 13.

In this case, since the pulse transit time is measured based on the first and second pulse wave signals PS1 and PS2 having the same waveform, the measurement accuracy of the pulse transit time can be further enhanced. Furthermore, since the cuff pressure Pc is set to the value at the time point when the cross-correlation coefficient r exceeds the threshold value Th, the pulse transit time can be acquired without needlessly increasing the cuff pressure Pc. As a result, the physical burden on the user can be reduced.

Third Embodiment

Next, a third embodiment of the blood pressure measurement device including the pulse wave measurement device of the present invention will be described in detail with reference to the drawings. The description of the same parts as those in the first embodiment will be omitted.

(Configuration of Sphygmomanometer)

Figure 23:
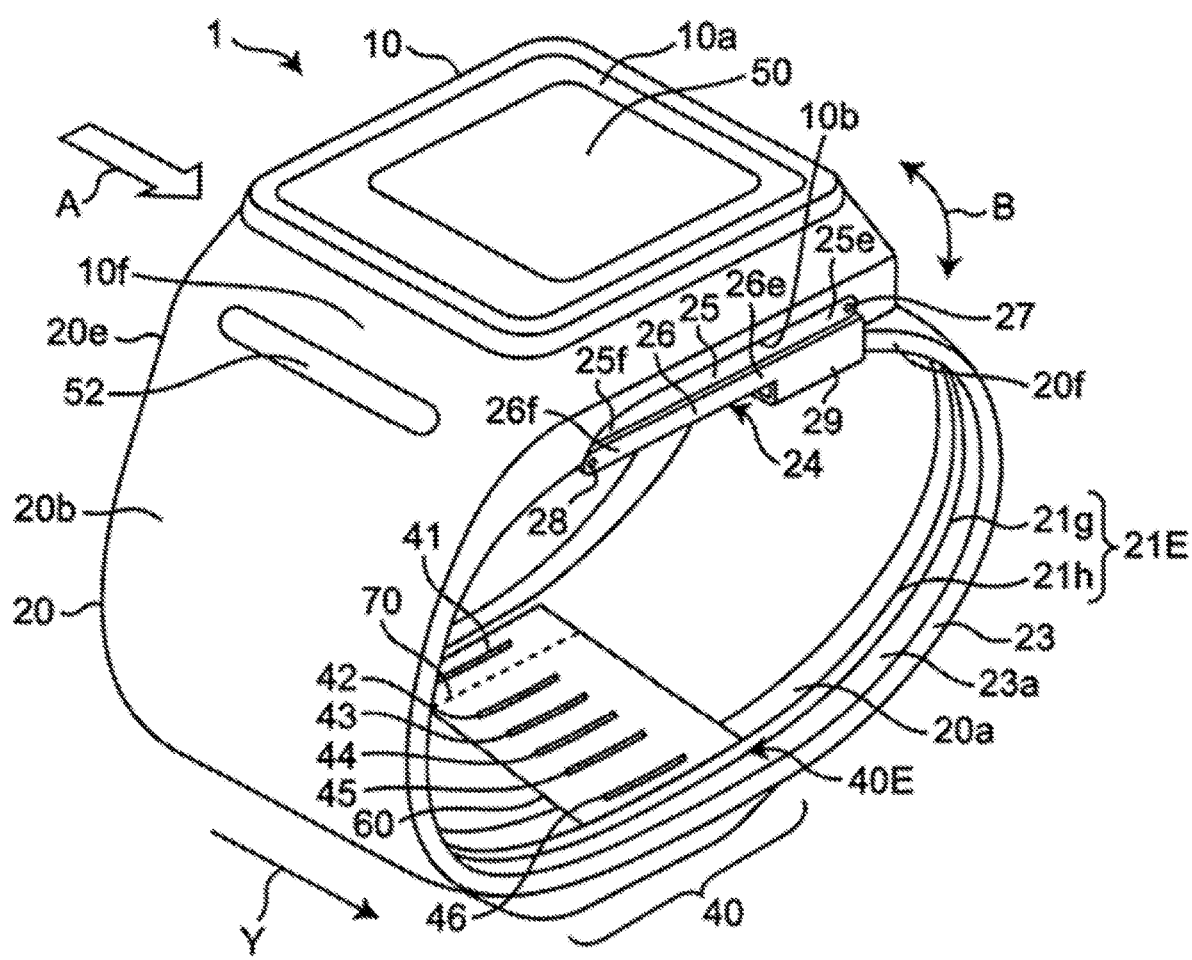
FIG. 23 is a perspective view showing an appearance of a wrist type sphygmomanometer according to a third embodiment according to the blood pressure measurement device including the pulse wave measurement device of the present invention.
Figure 24:
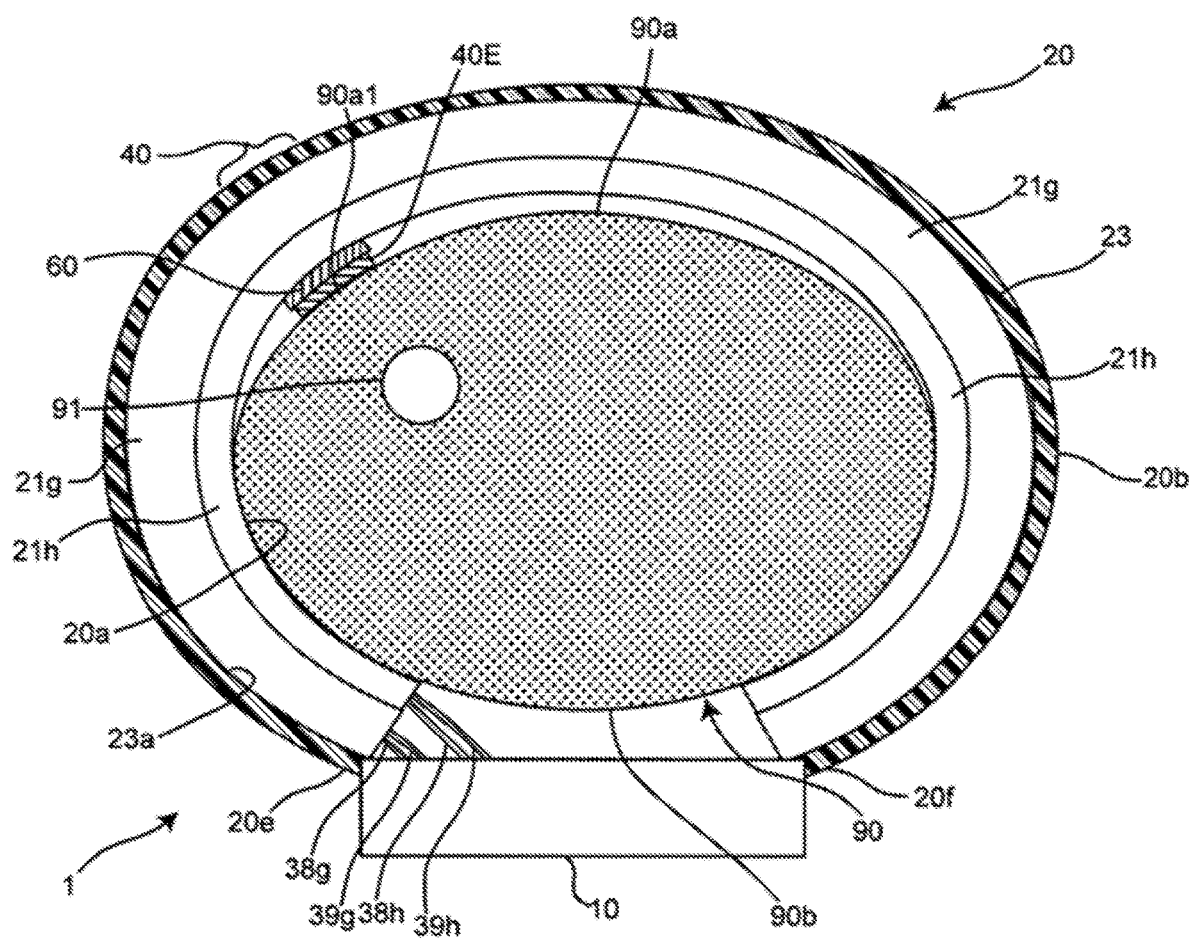
FIG. 24 is a diagram schematically showing a cross-section perpendicular to the longitudinal direction of the wrist in the state where the sphygmomanometer shown in FIG. 23 is worn on the left wrist.

FIG. 23 shows an appearance of the sphygmomanometer 1 according to the third embodiment when the sphygmomanometer 1 is viewed from an oblique side. FIG. 24 schematically shows a cross-section perpendicular to the longitudinal direction of the left wrist 90 in a state where the sphygmomanometer 1 is worn on the left wrist 90 as a measurement target site.

As well understood from FIG. 23, the press cuff group 21E serving as the pressing unit in the third embodiment includes a press cuff 21g serving as a seventh pressing member and a press cuff 21h serving as an eighth pressing member. The press cuff 21g is configured so that the width in the width direction Y of the belt 20 is set to a width over which the entire impedance measurement unit 40 is covered. The press cuff 21h is provided on the inner peripheral side of the inner peripheral surface 20a of the press cuff 21g (belt 20) and at the position corresponding to the current electrode 46 of the impedance measurement unit 40. The width in the width direction Y of the press cuff 21h is set to a width corresponding to the current electrode 46 in the impedance measurement unit 40. A spacer 70 is further provided on the inner peripheral side of the inner peripheral surface 20a of the press cuff 21g (belt 20) and at the position corresponding to the current electrode 41 of the impedance measurement unit 40. In this example, the spacer 70 is made of plate-like resin (in this example, polypropylene) having a thickness of about 1 to 2 mm. Furthermore, a solid 60 as a solid material is provided at the position corresponding to the impedance measurement unit 40 on the inner peripheral surface 20a of the spacer 70 (belt 20), the inner peripheral surface 20a of the press cuff 21g (belt 20), and the inner peripheral surface 20a of the press cuff 21h (belt 20). In this example, the solid 60 is made of plate-like resin (in this example, ABS) having a thickness of about 7 mm. An electrode group 40E is provided on the inner peripheral surface of the solid 60.

In this example, the press cuff group 21E is configured as a fluid bag by confronting two stretchable polyurethane sheets in the thickness direction and welding the peripheral edge portions thereof. As shown in FIG. 24, the solid 60 is arranged at a site corresponding to the radial artery 91 of the left wrist 90 on the inner peripheral surface 20a of the press cuff 21h (belt 20), and the electrode group 40E of the impedance measurement unit 40 is arranged on the inner peripheral surface of the solid 60. In a region where neither the press cuff 21h nor the spacer 70 is provided in the width direction Y of the belt 20, the solid 60 is arranged at a site corresponding to the radial artery 91 of the left wrist 90 on the inner peripheral surface 20a of the press cuff 21g (belt 20). In a region where the spacer 70 is provided in the width direction Y of the belt 20, the solid 60 is arranged at a site corresponding to the radial artery 91 of the left wrist 90 on the inner peripheral surface 20a of the spacer 70 (belt 20).

Figure 25:
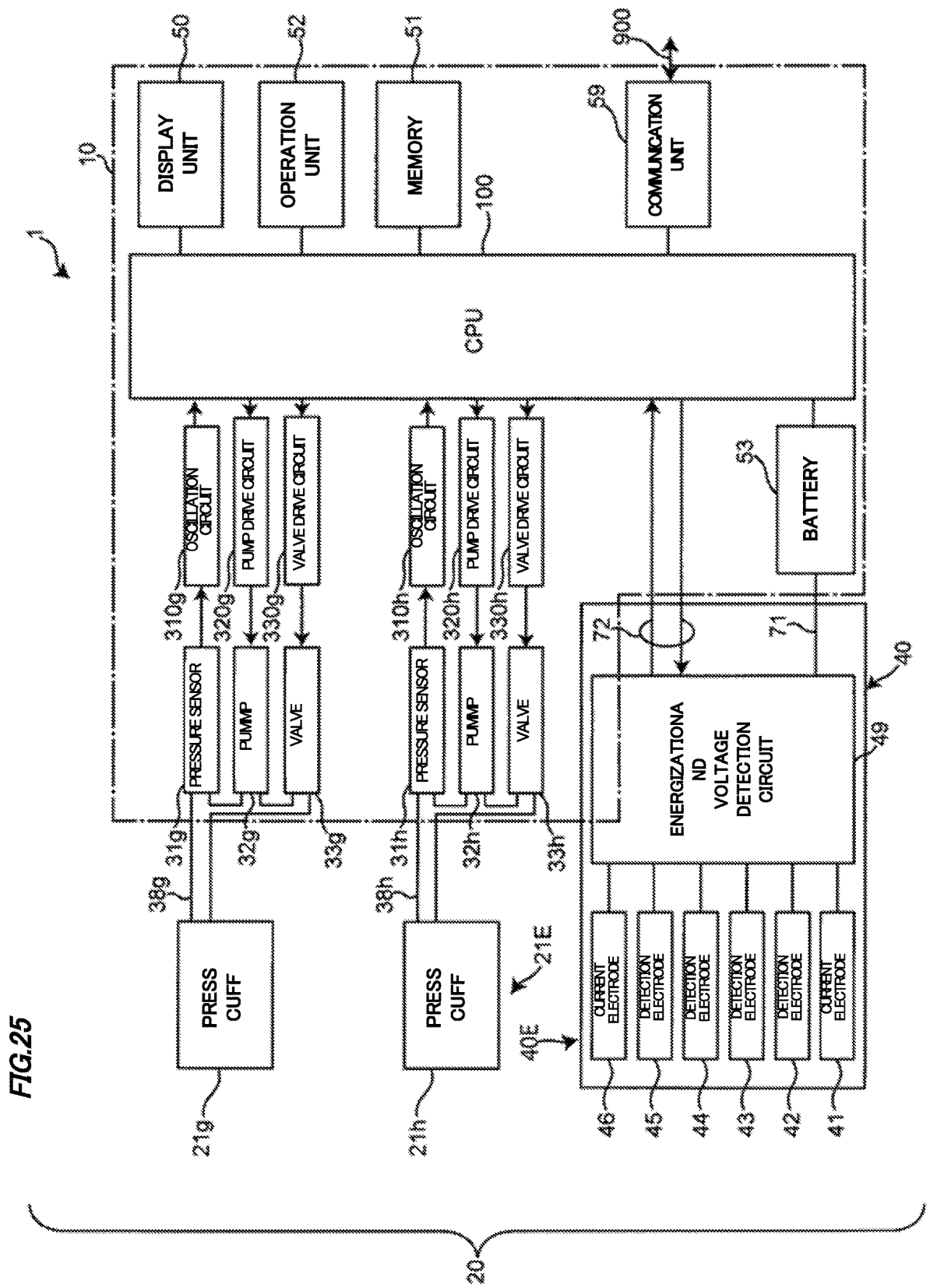
FIG. 25 is a diagram showing a block configuration of a control system of the sphygmomanometer shown in FIG. 23.

FIG. 25 shows a block configuration of a control system of the sphygmomanometer 1 according to the third embodiment. In addition to the display unit 50 and the operation unit 52, the CPU 100 as the control unit, the memory 51 as the storage unit, and the communication unit 59 are mounted in the main body 10 of the sphygmomanometer 1 as in the case of the sphygmomanometer 1 of the first embodiment. Pressure sensors 31g and 31h, pumps 32g and 32h, and valves 33g and 33h are also mounted in the main body 10 (note that in the following description, these units may be collectively referred to as the pressure sensor 31, the pump 32 and the valve 33). Oscillation circuits 310g and 310h for converting outputs from the pressure sensors 31g and 31h into frequencies, pump drive circuits 320g and 320h for driving the pumps 32g and 32h respectively, and valve drive circuits 330g and 330h for driving the valves 33g and 33h respectively are further mounted in the main body (note that in the following description, these units may be collectively referred to as the oscillation circuit 310, the pump drive circuit 320, and the valve drive circuit 330). In this example, a piezoresistive pressure sensor is also used as the pressure sensor 31, and is connected to the pump 32, the valve 33 and the press cuff group 21E via the air pipe 38 (38g, 38h).

Figure 26A:
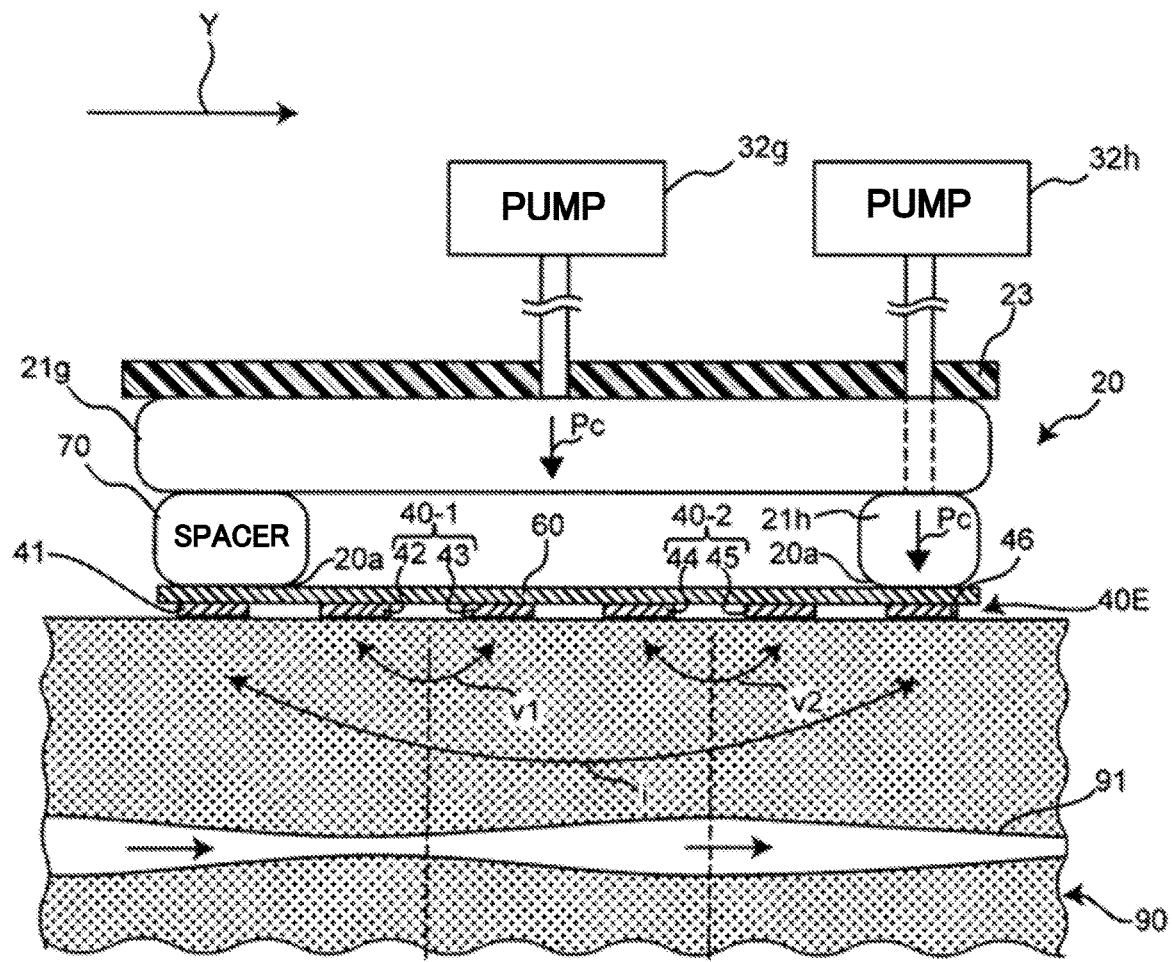
FIG. 26A is a diagram schematically showing a cross-section along the longitudinal direction of the wrist in the state where the sphygmomanometer shown in FIG. 23 is worn on the left wrist.
Figure 26B:
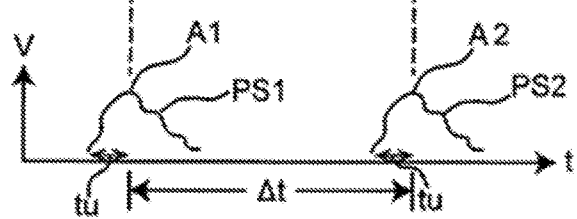
FIG. 26B is a diagram showing waveforms of first and second pulse wave signals output from the first and second pulse wave sensors, respectively.

FIG. 26A schematically shows a cross-section along the longitudinal direction of the wrist in a state where the sphygmomanometer 1 is worn on the left wrist 90. FIG. 26B shows the waveforms of the first pulse wave signal PS1 and the second pulse wave signal PS2 which are output by the first pulse wave sensor 40-1 and the second pulse wave sensor 40-2, respectively. As shown in FIG. 26A, the solid 60 as a solid material is arranged across the first pulse wave sensor 40-1 and the second pulse wave sensor 40-2 with respect to the artery direction of the radial artery 91. The press cuff 21g constituting the seventh pressing member is arranged so as to face the solid 60. In this example, the press cuff 21g is configured so that the width in the arterial direction (width direction Y) thereof is set to a width over which the entire area of the solid 60 is covered in the arterial direction (width direction Y), and provided at a position where pressing force can be generated so as to direct to the entire area of the solid 60.

The press cuff 21$h$ constituting the eighth pressing member is interposed between one side of outer portions of the solid 60 than the first pulse wave sensor 40-1 and the second pulse wave sensor 40-2 with respect to the arterial direction and the press cuff 21$g$. In this example, the press cuff 21$h$ is provided at the position corresponding to the current electrode 46. The spacer 70 is interposed between the other side of the outer portions of the solid 60 and the press cuff 21$g$. In this example, the spacer 70 is provided at the position corresponding to the current electrode 41. Therefore, under a state where the pressure of the press cuff 21$h$ is increased by the pump 32$h$, when the pressure of the press cuff 21$g$ is increased by the pump 32$g$, the press cuff 21$g$ generates pressing force toward the entire area of the solid 60 to press the spacer 70 and the press cuff 21$h$, and the spacer 70 and the press cuff 21$h$ presses the solid 60. The solid 60 presses the paired current electrodes 41 and 46, the first pulse wave sensor 40-1, and the second pulse wave sensor 40-2 against the palmar side surface 90$a$ of the left wrist 90. In this state, when the pressure of the press cuff 21$h$ is increased or reduced by the pump 32$h$ or the valve 33$h$, the pressing force to the solid 60 on only the side corresponding to the current electrode 46 changes, so that the pressing forces of the paired current electrodes 41 and 46, the first pulse wave sensor 40-1 and the second pulse wave sensor 40-2 against the left wrist 90 are different so as to follow a certain pressure gradient in the arterial direction. In this example, the pumps 32$g$ and 32$h$ can independently increase the pressures of the press cuffs 21$g$ and 21$h$ under the control of the CPU 100. Therefore, the pressing forces of the paired current electrodes 41 and 46, the first pulse wave sensor 40-1, and the second pulse wave sensor 40-2 against the palmar side surface 90$a$ of the left wrist 90 can be set to proper values along a certain pressure gradient.

(Operation of Blood Pressure Measurement by Oscillometric Method)

The blood pressure measurement by the oscillometric method in the sphygmomanometer 1 according to the third embodiment is performed according to the operation flow shown in FIG. 6 as in the case of the first embodiment.

When the CPU 100 exhausts the air in the press cuff group 21E (step S2 in FIG. 6), the CPU 100 performs control of exhaust on the press cuffs 21$g$ and 21$h$. When the CPU 100 gradually increases the cuff pressure Pc of the press cuff group 21E, the CPU 100 performs control of increasing pressure on the press cuffs 21$g$ and 21$h$. In order, the cuff pressure Pc of the press cuff 21$g$ is first gradually increased, and when the cuff pressure Pc of the press cuff 21$g$ becomes a constant cuff pressure Pc, the cuff pressure Pc of the press cuff 21$h$ may be gradually increased. Alternatively, the cuff pressures Pc of the press cuff 21$g$ and the press cuff 21$h$ may be simultaneously gradually increased. Furthermore, when the CPU 100 calculates the blood pressure value (steps S3 to S5 in FIG. 6), the cuff pressures Pc of both the press cuffs 21$g$ and 21$h$ may be monitored, or the cuff pressure Pc of either of the press cuffs 21$g$ or 21$h$ may be monitored. The other control in the operation flow of FIG. 6 is similar to the control of the first embodiment, and thus the description thereof is omitted. Note that in this example, the calculation of the blood pressure value is not limitedly performed in the pressure-increasing step, and may be performed in the pressure-reducing step.

(Operation of Blood Pressure Measurement Based on Pulse Transit Time)

Figure 27:
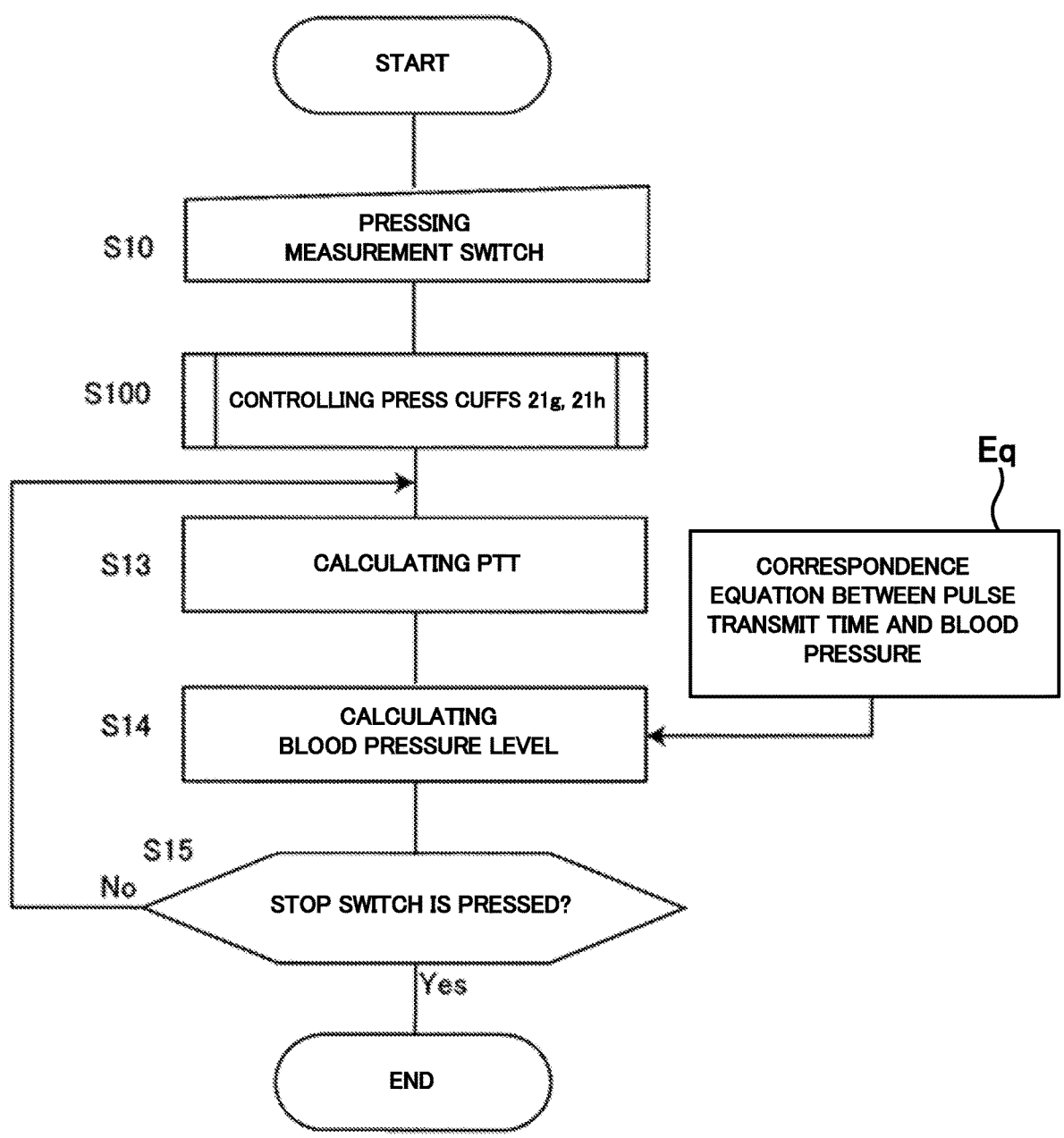
FIG. 27 is a diagram showing an operation flow when the sphygmomanometer executes the pulse wave measurement method according to an embodiment to acquire a pulse transit time (PTT) and performs blood pressure measurement (estimation) based on the pulse transit time.

FIG. 27 shows an operation flow when the sphygmomanometer 1 of the second embodiment performs the blood pressure measurement (estimation) based on the pulse transit time.

Figure 28:
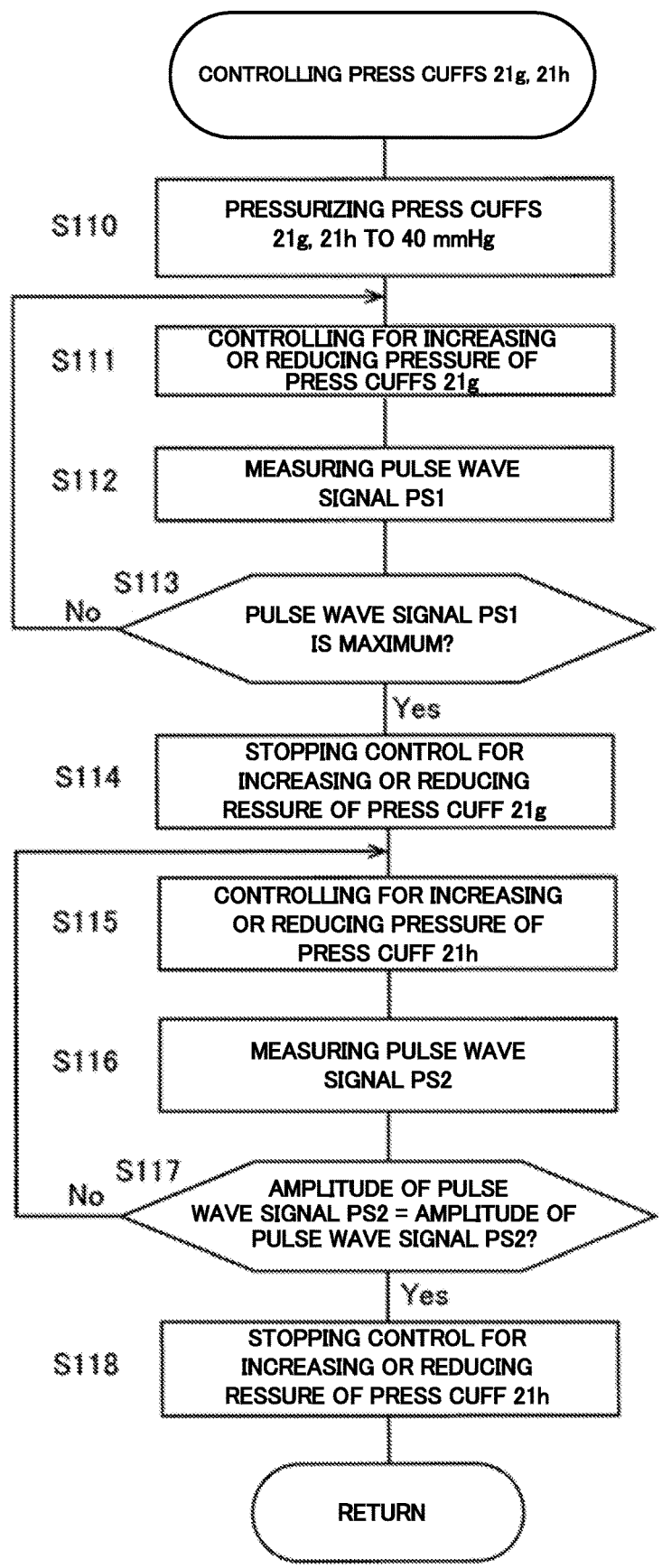
FIG. 28 is a diagram showing an example of an operation flow when cuffs for a detection electrode pair shown in the operation flow of FIG. 27 is controlled.

In the third embodiment, as shown in FIG. 27, when the user instructs the blood pressure measurement based on PTT with the push type switch as the operation unit 52 provided in the main body 10 (step S10 in FIG. 27), the CPU 100 works as a pulse wave sensor pressing force setting unit to start control of the press cuffs 21$g$ and 21$h$ (step S100 in FIG. 27). FIG. 28 shows an operation flow when the sphygmomanometer 1 controls the press cuffs 21$g$ and 21$h$.

Like the second embodiment, an operation flow shown in FIG. 28 is based on an idea that the pressing forces of the first pulse wave sensor 40-1 and the second pulse wave sensor 40-2 are set to different values so as to follow a certain pressure gradient, and the same waveform is acquired as the waveform of the first pulse wave signal PS1 and the waveform of the second pulse wave signal PS2. In this example, the pressing forces of the first pulse wave sensor 40-1 and the second pulse wave sensor 40-2 are set to different values so as to follow a certain pressure gradient via the solid 60 by changing the cuff pressure Pc of each of the press cuffs 21$g$ and 21$h$.

As shown in FIG. 28, when control of the press cuffs 21$g$ and 21$h$ is started, the CPU 100 works as a pulse wave sensor pressing force setting unit to close the valves 33$g$ and 33$h$ via the valve drive circuits 330$g$ and 330$h$ and drive the pumps 32$g$ and 32$h$ via the pump drive circuits 320$g$ and 320$h$ to increase the pressures of the press cuffs 21$g$ and 21$h$ to 40 mmHg (step S110 in FIG. 28). In this example, the cuff pressures Pc of the press cuffs 21$g$ and 21$h$ are continuously increased at a constant speed (=5 mmHg/s) to set the cuff pressures Pc of the press cuffs 21$g$ and 21$h$ to 40 mmHg.

Next, the CPU 100 drives the pump 32$g$ via the pump drive circuit 320$g$ to increase the pressure of the press cuff 21$g$ (step S111 in FIG. 28). In this example, the cuff pressure Pc of the press cuff 21$g$ is continuously increased at a constant speed (=5 mmHg/s). As a result, the press cuff 21$g$ presses the solid 60 via the spacer 70, and the solid 60 presses the current electrode 41 and the first pulse wave sensor 40-1 against the left wrist 90.

In this pressure-increasing step, the CPU 100 acquires the first pulse wave signal PS1 which is time-sequentially output by the first pulse wave sensor 40-1 (step S112 in FIG. 28), and also the CPU 100 determines whether the amplitude of the acquired first pulse wave signal PS1 is maximum (step S113 in FIG. 28).

When the amplitude of the first pulse wave signal PS1 is not maximum (NO in step S113 in FIG. 28), the CPU 100 drives or stops the pump 32$g$ via the pump drive circuit 320$g$, or opens or closes the valve 33$g$ via the valve drive circuit 330$g$ to increase or reduce the pressure of the press cuff 21$g$ (step S111 in FIG. 28). Then, the processing of steps S111 to S113 is repeated until the amplitude of the first pulse wave signal PS1 becomes maximum unless the cuff pressure Pc has reached the upper limit pressure (which is predetermined to, for example, 300 mmHg for safety). Note that as in the case of the first embodiment, not only increase of the pressure of the press cuff 21$g$, but also reduction of the pressure of the press cuff 21$g$ is performed because when the pressing force is increased even after the amplitude of the first pulse wave signal PS1 exhibits a maximum value, there is a tendency that blood vessels collapse and the amplitude of the first pulse wave signal PS1 gradually decrease.

Therefore, in this example, by performing not only increase of the pressure of the press cuff 21g, but also reduction of the pressure of the press cuff 21g, the cuff pressure Pc at which the amplitude of the first pulse wave signal PS1 becomes maximum is acquired.

When the amplitude becomes maximum (YES in step S113 in FIG. 28), the CPU 100 stops the pump 32g (step S114 in FIG. 28), and sets the cuff pressure Pc of the press cuff 21g to a value at that time point, that is, a value at the time point when the amplitude of the first pulse wave signal PS1 becomes maximum.

Next, the CPU 100 drives the pump 32h via the pump drive circuit 320h to increase the pressure of the press cuff 21h (step S115 in FIG. 28). In this example, the cuff pressure Pc of the press cuff 21h is continuously increased at a constant speed (=5 mmHg/s). As a result, the press cuff 21h presses the solid 60, and the solid 60 presses the current electrode 46 and the second pulse wave sensor 40-2. In addition, the solid 60 also presses the current electrode 41 and the first pulse wave sensor 40-1, so that a pressure gradient occurs between the pressing force of the first pulse wave sensor 40-1 and the pressing force of the second pulse wave sensor 40-2.

In this pressure-increasing step, the CPU 100 acquires the second pulse wave signal PS2 which is time-sequentially output by the second pulse wave sensor 40-2 (step S116 in FIG. 28), and also the CPU 100 works as a waveform comparing unit to determine whether the amplitude of the acquired second pulse wave signal PS2 is identical to the maximum amplitude of the first pulse wave signal PS1 set as described above (step S117 in FIG. 28). Note that in this example, an allowable range when "identical" is determined is set to a range of +10%.

When the amplitude of the second pulse wave signal PS2 is not maximum (NO in step S117 in FIG. 28), the CPU 100 drives or stops the pump 32h via the pump drive circuit 320h, or opens or closes the valve 33h via the valve drive circuit 330h to increase or reduce the pressure of the press cuff 21h (step S115 in FIG. 28). The processing of steps S115 to S117 is repeated until the amplitude of the second pulse wave signal PS2 becomes equal to the maximum amplitude of the first pulse wave signal PS1 unless the cuff pressure Pc has reached the upper limit pressure (which is predetermined to, for example, 300 mmHg for safety). Note that not only increase of the pressure of the press cuff 21h, but also reduction of the pressure of the press cuff 21h is performed because the relationship between the amplitude of the second pulse wave signal PS2 and the pressing force is similar to the relationship between the amplitude of the first pulse wave signal PS1 and the pressing force described above.

When the amplitude of the second pulse wave signal PS2 becomes equal to the maximum amplitude of the first pulse wave signal PS1 (YES in step S117 in FIG. 28), the CPU 100 stops the pump 32h (step S118 in FIG. 28), and sets the cuff pressure Pc of the press cuff 21h to a value at that time point, that is, a value at the time point when the amplitude of the second pulse wave signal PS2 becomes equal to the maximum amplitude of the first pulse wave signal PS1. The control of the press cuffs 21g and 21h (step S100 in FIG. 27) is terminated with the operation flow described above.

In this state, the CPU 100 works as a measurement processing unit to acquire the time difference Δt (see FIG. 26B) between the first and second pulse wave signals PS1 and PS2 as a pulse transit time (PTT) (step S14 in FIG. 27). More specifically, in this example, the time difference Δt between the peak A1 of the first pulse wave signal PS1 and the peak A2 of the second pulse wave signal PS2 is acquired as the pulse transit time (PTT).

In this case, since the pulse transit time is measured based on the first and second pulse wave signals PS1 and PS2 having the same waveform, the measurement accuracy of the pulse transit time can be enhanced. Furthermore, the pulse transit time can be acquired without needlessly increasing the cuff pressure Pc. As a result, the physical burden on the user can be reduced.

Next, the CPU 100 works as a first blood pressure calculation unit, and uses a predetermined correspondence equation Eq between the pulse transit time and the blood pressure to calculate (estimate) the blood pressure based on the pulse transit time (PTT) acquired in step S13 (step S14 in FIG. 27). Here, as in the case of the first embodiment, the predetermined correspondence equation Eq between the pulse transit time and the blood pressure is provided, for example, as a publicly known a fractional function including a term of $1/DT^2$ as indicated by the equation (Eq. 2) in FIG. 32.

When the blood pressure is calculated (estimated) as described above, the measurement accuracy of the pulse transit time is enhanced as described above, so that the measurement accuracy of the blood pressure can be enhanced. Note that the measurement result of the blood pressure value is displayed on the display unit 50 and recorded in the memory 51.

In this example, when stop of measurement is not instructed by the push type switch as the operation unit 52 in step S15 in FIG. 27 (NO in step S15 in FIG. 27), the calculation of the pulse transit time (PTT) (step S13 in FIG. 27) and the calculation (estimation) of the blood pressure (step S14 in FIG. 27) are periodically repeated each time the first and second pulse wave signals PS1 and PS2 are input according to the pulse wave. The CPU 100 updates and displays the measurement result of the blood pressure value on the display unit 50, and accumulates and records the measurement result in the memory 51. When the stop of measurement is instructed in step S15 in FIG. 27 (YES in step S15 in FIG. 27), the CPU 100 opens the valves 33g and 33h via the valve drive circuits 330g and 330h, performs control of discharging the air in the press cuffs 21g and 21h, and terminates the measurement operation.

According to the sphygmomanometer 1, the blood pressure can be continuously measured over a long period of time with light physical burden on users by the blood pressure measurement based on the pulse transit time (PTT).

According to the sphygmomanometer 1, the blood pressure measurement (estimation) based on the pulse transit time and the blood pressure measurement by the oscillometric method can be performed by an integrated device. Therefore, the convenience of users can be enhanced.

According to the sphygmomanometer 1, as compared with the first embodiment, the press cuff, the pressure sensor, the oscillation circuit, the pump, the pump drive circuit, the valve, and the valve drive circuit can be reduced, and thus the configuration can be simplified.

(Third Modification)

Figure 29:
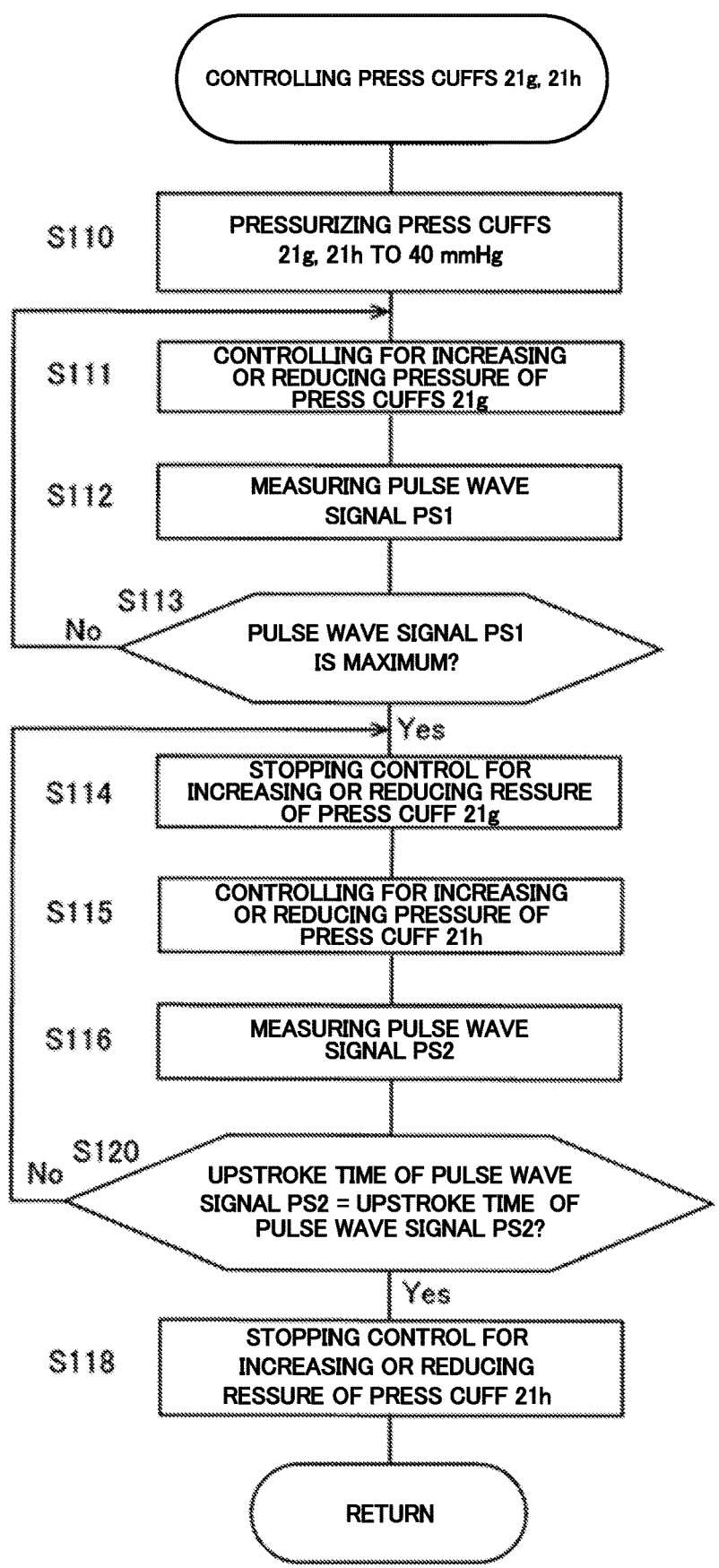
FIG. 29 is a diagram showing another example of the operation flow when the cuffs for the detection electrode pair shown in the operation flow of FIG. 27 is controlled.

FIG. 29 shows another example of the operation flow when the sphygmomanometer 1 controls the press cuffs 21g and 21h. In the example shown in FIG. 28, in step S117, whether the waveform of the second pulse wave signal PS2 and the waveform of the first pulse wave signal PS1 having the maximum amplitude are identical to each other is determined based on the amplitude of each of the waveforms. However, the determination is not limited to this manner. For example, as shown in step S120 in FIG. 29, based on whether the upstroke time of the second pulse wave signal PS2 is equal to the upstroke time of the first pulse wave signal PS1 having the maximum amplitude, it may be determined that the respective waveforms are identical to each other.

As shown in FIG. 29, in this operation flow as well as the operation flow of FIG. 28, the CPU 100 sets the cuff pressure Pc of the press cuff 21g so that the amplitude of the first pulse wave signal PS1 becomes maximum while increasing or reducing the pressure of the press cuff 21g (steps S111 to S113 in FIG. 29). In this case, when the CPU 100 determines that the amplitude of the first pulse wave signal PS1 is maximum in the operation flow of FIG. 29 (YES in step S113 of FIG. 29), the CPU 100 records the upstroke time of the first pulse wave signal PS1 in the memory 51. Note that in this example, an allowable range when it is determined that the upstroke times are "identical" is set to a range of ±1%.

Next, the CPU 100 drives the pump 32h via the pump drive circuit 320h to increase the pressure of the press cuff 21h corresponding to the second pulse wave sensor 40-2 (step S115 in FIG. 29). In this pressure-increasing step, the CPU 100 acquires the second pulse wave signal PS2 which is time-sequentially output by the second pulse wave sensor 40-2 (step S115 in FIG. 29), and also the CPU 100 works as a waveform comparing unit to determine whether the upstroke time tu of the acquired second pulse wave signal PS2 and the upstroke time tu of the first pulse wave signal PS1 recorded in the memory 51 are equal to each other (step S120 in FIG. 29). Note that in this example, an allowable range when it is determined that the upstroke times tu are "identical" is set to a range of ±1%.

Here, when the upstroke time tu of the second pulse wave signal PS2 and the upstroke time tu of the first pulse wave signal PS1 are not equal to each other (NO in step S120 of FIG. 29), the processing of steps S115 to S120 is repeated until the upstroke times tu are equal to each other unless the cuff pressure Pc has reached the upper limit pressure (which is predetermined to, for example, 300 mmHg for safety). When the upstroke times tu become equal to each other (YES in step S120 in FIG. 29), the CPU 100 stops the pump 32h (step S118 in FIG. 29), and sets the cuff pressure Pc of the press cuff 21h to a value at that time point, that is, a value at the time point when the upstroke times tu become equal to each other. As a result, since the pulse transit time is measured based on the first and second pulse wave signals PS1 and PS2 which have the same waveform, the measurement accuracy of the pulse transit time can be further enhanced.

Figure 30:
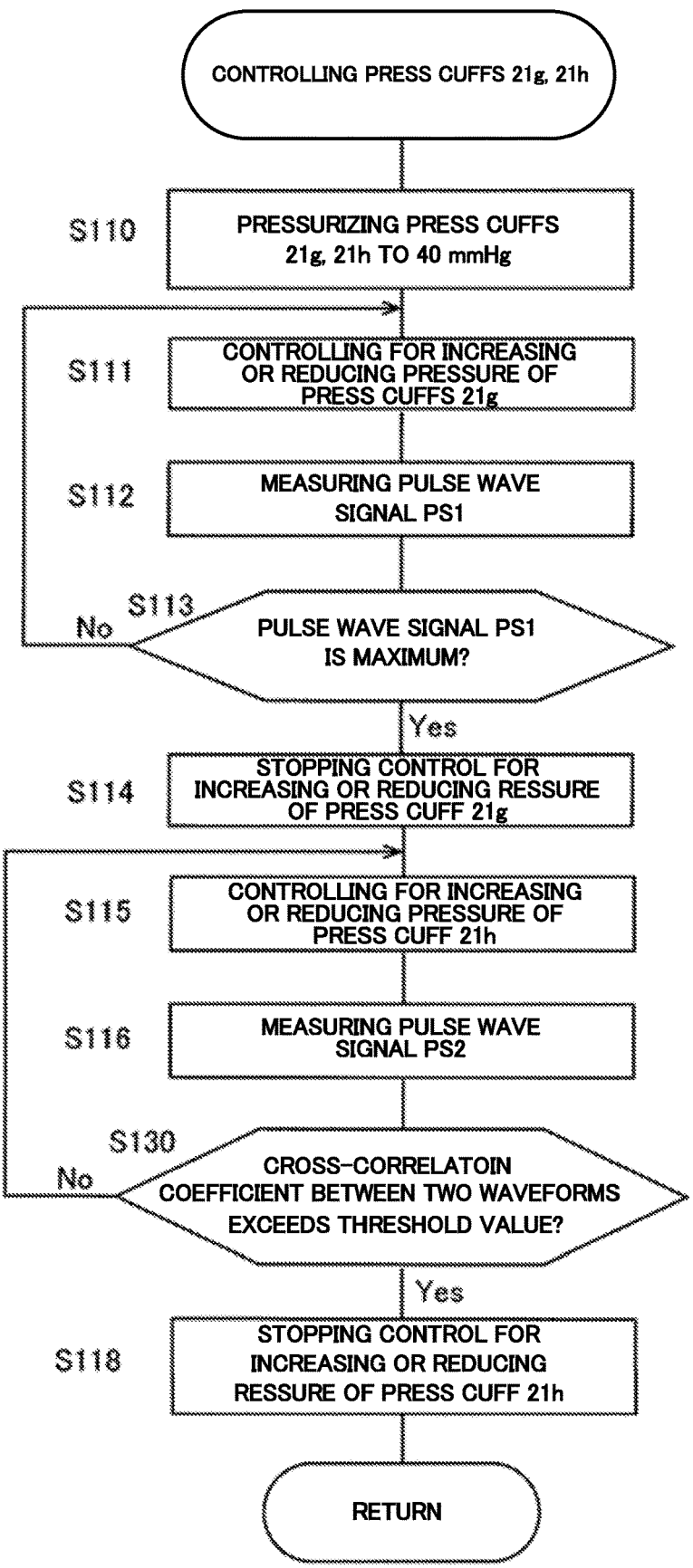
FIG. 30 is a diagram showing another example of the operation flow when the cuffs for the detection electrode pair shown in the operation flow of FIG. 27 is controlled.

FIG. 30 shows still another example of the operation flow when the sphygmomanometer 1 controls the press cuffs 21g and 21h. Whether the waveform of the second pulse wave signal PS2 and the waveform of the first pulse wave signal PS1 having the maximum amplitude are identical to each other is determined based on the amplitude of each of the respective waveforms in the operation flow of FIG. 28 or each upstroke time in the operation flow of FIG. 29. However, the determination is not limited to this manner. For example, as shown in step S130 of FIG. 30, when the cross-correlation coefficient r between the two waveforms (see the equation Eq. 1 of FIG. 36) exceeds a threshold value, it may be determined that the two waveforms are identical to each other.

The operation flow shown in FIG. 30 is also based on the idea that the range in which the cross-correlation coefficient r exceeds the predetermined threshold value Th (in this example, Th=0.99) is the proper pressing range. In this example, the proper pressing range is a range in which the pressing force (cuff pressure Pc) ranges from the lower limit value P1≅72 mmHg to the upper limit value P2≅135 mmHg.

As shown in FIG. 30, in this operation flow as well as the operation flow of FIG. 28 and FIG. 29, the CPU 100 sets the cuff pressure Pc of the press cuff 21g so that the amplitude of the first pulse wave signal PS1 becomes maximum while increasing or reducing the pressure of the press cuff 21g (steps S111 to S113 in FIG. 30). Note that in this example, the CPU 100 accumulates and records data necessary for calculation of the cross-correlation coefficient r in the memory 51 for the first pulse wave signal PS1 having the maximum amplitude.

Next, the CPU 100 drives the pump 32h via the pump drive circuit 320h to increase the pressure of the press cuff 21h corresponding to the second pulse wave sensor 40-2 (step S115 in FIG. 30). In this pressure-increasing step, the CPU 100 acquires the second pulse wave signal PS2 which is time-sequentially output by the second pulse wave sensor 40-2 (step S116 in FIG. 30), calculates the cross-correlation coefficient r between the waveforms of the first and second pulse wave signals PS1 and PS2 in real time based on the acquired data and the data of the first pulse wave signal PS1 accumulated and recorded in the memory 51, and determines whether the calculated cross-correlation coefficient r exceeds the predetermined threshold value Th (=0.99) (step S130 in FIG. 30).

Here, when the cross-correlation coefficient r is not more than the threshold value Th (NO in step S130 of FIG. 30), the processing of steps S115 to S130 is repeated until the cross-correlation coefficient r exceeds the threshold value Th unless the cuff pressure Pc has reached the upper limit pressure (which is predetermined to, for example, 300 mmHg for safety). When the cross-correlation coefficient r exceeds the threshold value Th (YES in step S113 in FIG. 30), the CPU 100 stops the pump 32h (step S118 in FIG. 30), and sets the cuff pressure Pc of the press cuff 21h to a value at that time point, that is, a value at the time point when the cross-correlation coefficient r exceeds the threshold value Th. In this example, the cuff pressure Pc is set to a value at the time point when the cross-correlation coefficient r exceeds the threshold value Th, that is, P1 (≅72 mmHg) shown in FIG. 13.

In this case, the pulse transit time is measured based on the first and second pulse wave signals PS1 and PS2 which have the same waveform, so that the measurement accuracy of the pulse transit time can be further enhanced. Furthermore, since the cuff pressure Pc is set to a value at the time point when the cross-correlation coefficient r exceeds the threshold value Th, the pulse transit time can be acquired without needlessly increasing the cuff pressure Pc. As a result, the physical burden on the user can be reduced.

Fourth Embodiment

Next, a fourth embodiment of the blood pressure measurement device including the pulse wave measurement device of the present invention will be described in detail with reference to the drawings.

(Configuration of Sphygmomanometer)

Figure 31:
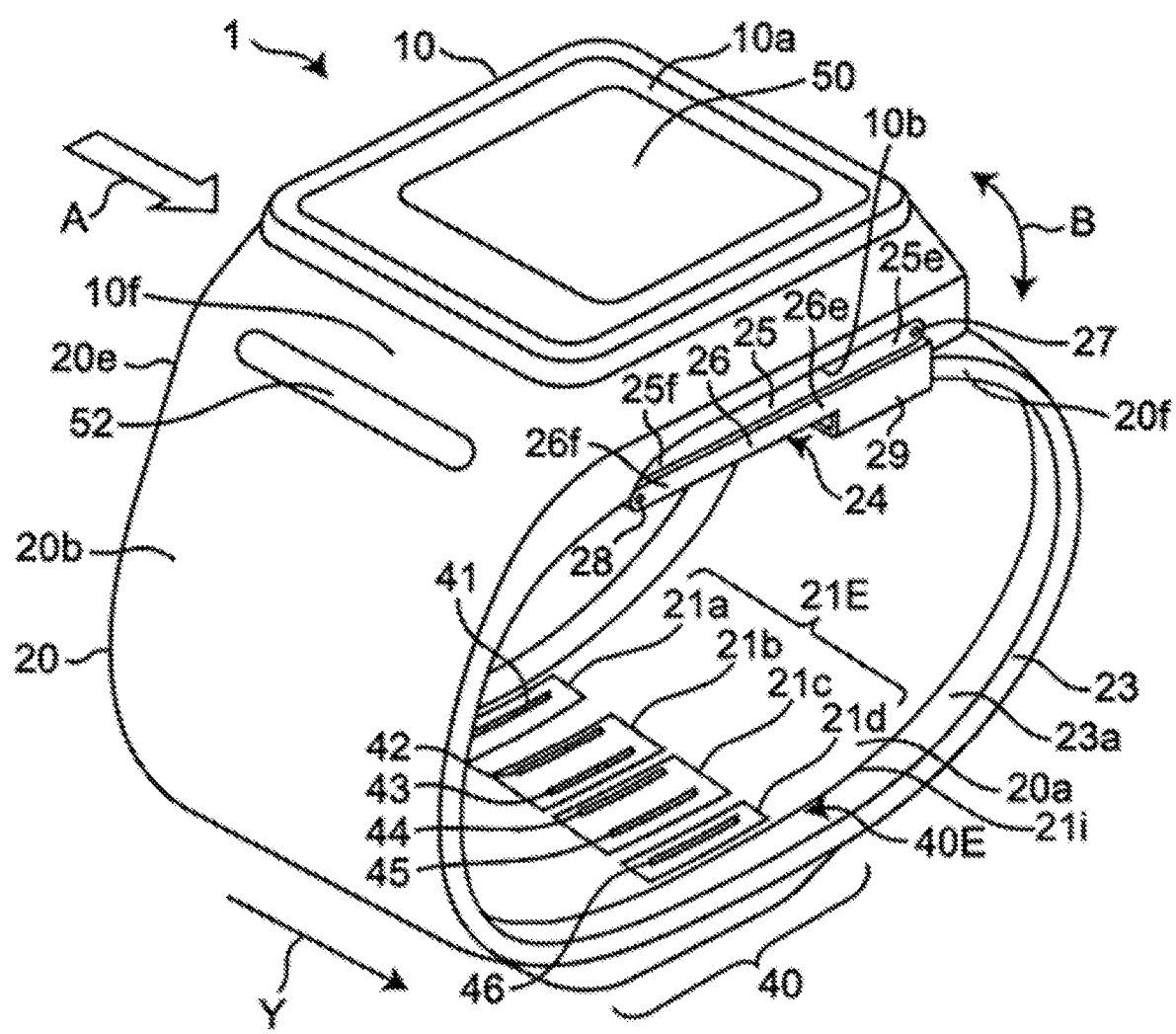
FIG. 31 is a perspective view showing an appearance of a wrist type sphygmomanometer according to a fourth embodiment according to the blood pressure measurement device including the pulse wave measurement device of the present invention.
Figure 32:
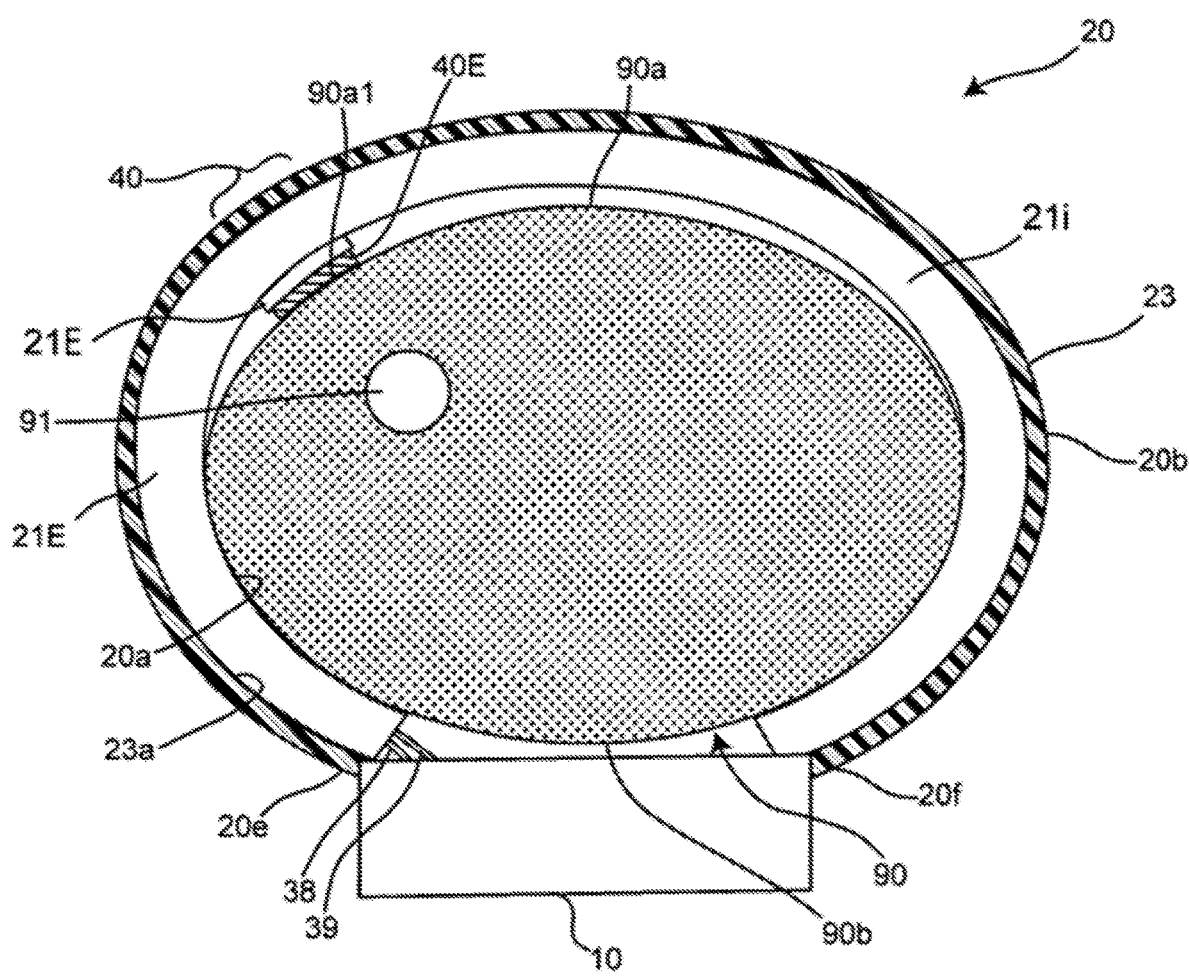
FIG. 32 is a diagram schematically showing a cross-section perpendicular to the longitudinal direction of the wrist in a state where the sphygmomanometer is worn on the left wrist.

FIG. 31 shows the appearance of the sphygmomanometer 1 according to the fourth embodiment when the sphygmomanometer 1 is viewed from an oblique side. FIG. 32 schematically shows a cross-section perpendicular to the longitudinal direction of the left wrist 90 in the case where the blood pressure measurement is performed by the oscillometric method in a state where the sphygmomanometer 1 is worn on the left wrist 90 as a measurement target site.

As shown in FIG. 31, in the sphygmomanometer 1 according to the fourth embodiment, a press cuff 21*i* working as a compressing member is interposed between the press cuff group 21E and the strip 23 of the belt 20. The press cuff group 21E is divided with respect to the width direction Y of the belt 20 as in the case of the first embodiment, and includes the press cuff 21*a* as the third pressing member, the press cuff 21*b* as the first pressing member, the press cuff 21*c* as the second pressing member, and the press cuff 21*d* as the fourth pressing member. The press cuffs 21*a* and 21*d* are separated from each other in connection with the paired current electrodes 41 and 46 as in the case of the first embodiment. The press cuffs 21*b* and 21*c* are separated from each other in connection with the paired first detection electrodes 42 and 43 constituting the first pulse wave sensor 40-1 and the paired second detection electrodes 44 and 45 constituting the second pulse wave sensor 40-2. The lengths of the press cuff 21*a*, the press cuff 21*b*, the press cuff 21*c*, and the press cuff 21*d* in the circumferential direction (longitudinal direction) of the strip 23 are set so as to be capable of pressing locally the paired current electrodes 41 and 46, the first pulse wave sensor 40-1, and the second pulse wave sensor 40-2 respectively unlike the first embodiment.

Like the other press cuffs, the press cuff 21*i* is configured as a fluid bag by confronting two stretchable polyurethane sheets in the thickness direction and welding the peripheral edge portions thereof. As shown in FIG. 32, the press cuff 21*i* has a length in the circumferential direction (longitudinal direction) along the strip 23, and can be mounted to be wound around the left wrist 90 as a measurement target site. The press cuff 21*i* is set to a pressurized state for compressing the left wrist 90 by supplying fluid thereto, and set to a depressurized state for releasing compression on the left wrist 90 by discharging the fluid therefrom. FIG. 32 schematically shows a cross-section perpendicular to the longitudinal direction of the left wrist 90 of the sphygmomanometer 1 when the press cuff 21*i* is set to the pressurized state, and the press cuff 21*a*, the press cuff 21*b*, the press cuff 21*c*, and the press cuff 21*d* are set to the depressurized state.

Figure 33:
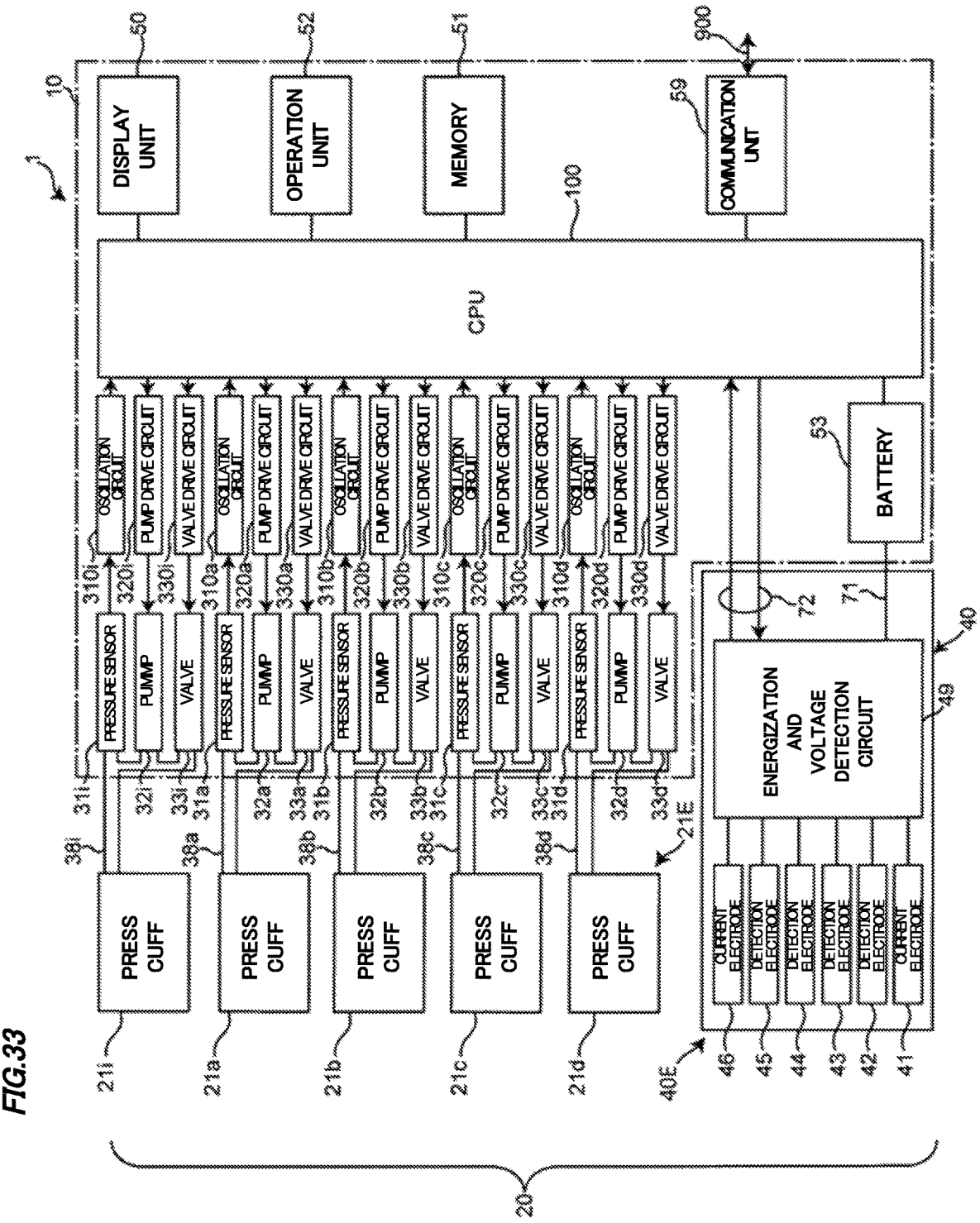
FIG. 33 is a diagram showing a block configuration of a control system of the sphygmomanometer.

FIG. 33 shows a block configuration of a control system of the sphygmomanometer 1 according to the fourth embodiment. As shown in FIG. 33, a pressure sensor 31*i*, a pump 32*i*, and a valve 33*i* are mounted in the main body 10 of the sphygmomanometer 1 according to the fourth embodiment unlike the first embodiment. Furthermore, unlike the first embodiment, an oscillation circuit 310*i* for converting an output from the pressure sensor 31*i* into a frequency, a pump drive circuit 320*i* for driving the pump 32*i*, and a valve drive circuit 330*i* for driving the valve 33*i* are mounted in the main body 10. In this example, a piezoresistive pressure sensor is also used as the pressure sensor 31*i*, and the pressure sensor 31*i* is connected to the pump 32*i*, the valve 33*i* and the press cuff 21*i* via the air pipe 38*i*.

Figure 34:
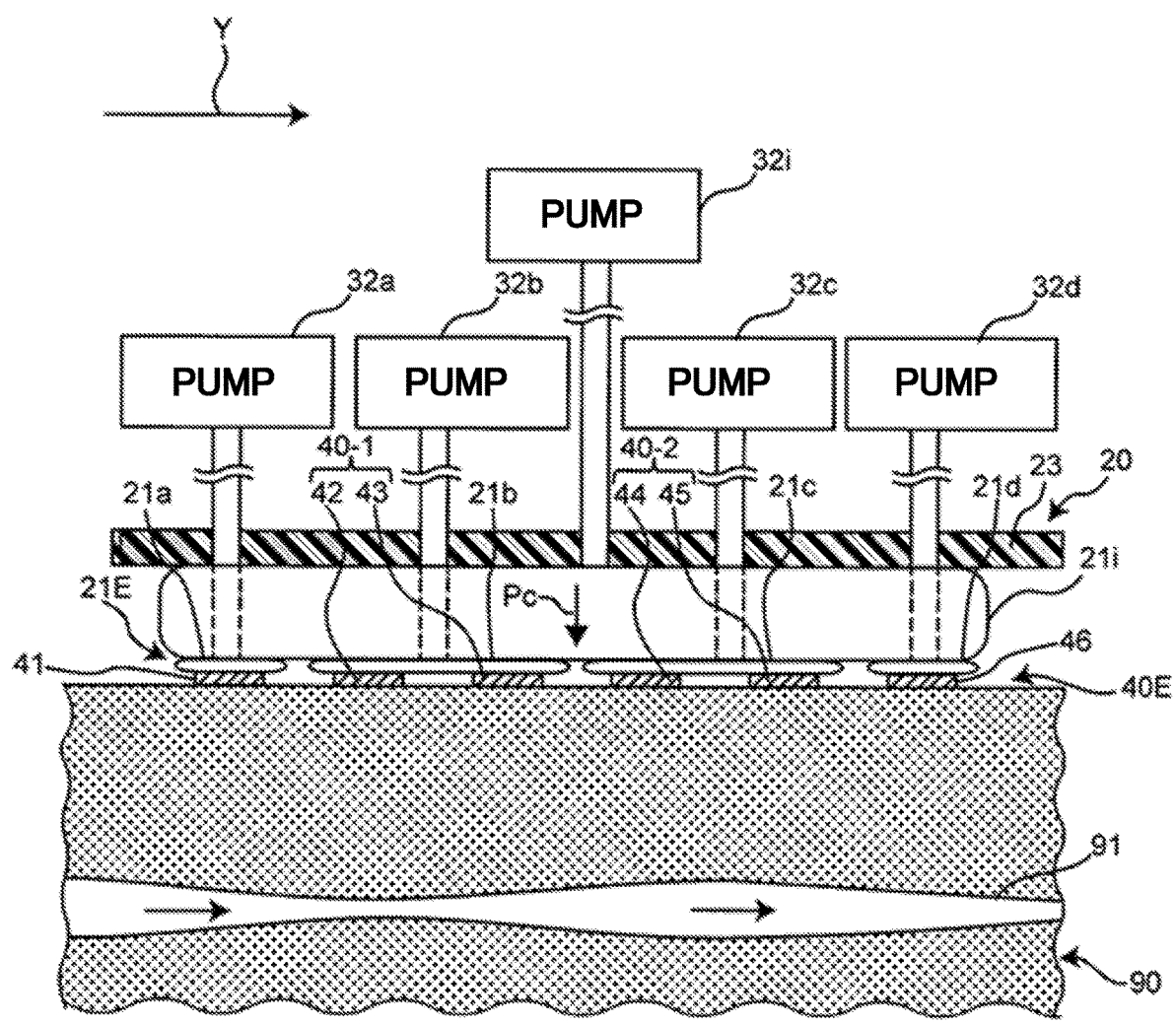
FIG. 34 is a diagram schematically showing a cross-section along the longitudinal direction of the wrist in a case where the blood pressure measurement is performed by the oscillometric method in a state where the sphygmomanometer is worn on the left wrist.

FIG. 34 schematically shows a cross-section along the longitudinal direction of the wrist in a state where the sphygmomanometer 1 is worn on the left wrist 90 when blood pressure measurement is performed by the oscillometric method. As shown in FIG. 34, the press cuff 21*i* has a width over which the press cuff 21*i* covers the entire area of the press cuff 21*a*, the press cuff 21*b*, the press cuff 21*c*, and the press cuff 21*d* in the artery direction (width direction Y) of the radial artery 91, and is provided at a position where the press cuff 21*i* can compress the left wrist 90 to sufficiently close the radial artery 91 under the pressurized state. Note that in the fourth embodiment, when the blood pressure measurement based on the pulse transit time is performed, the press cuff 21*i* is set to the depressurized state and the press cuff 21*a*, the press cuff 21*b*, the press cuff 21*c*, and the press cuff 21*d* are set to the pressurized state. In this case, the state is set to a state similar to the state of the sphygmomanometer 1 of the first embodiment shown in FIG. 5A. The sphygmomanometer 1 according to the fourth embodiment is different from the first embodiment in that the press cuff 21*i* under the depressurized state exists between the strip 23 and the outer peripheral side of the press cuff 21*a*, the press cuff 21*b*, the press cuff 21*c*, and the press cuff 21*d*.

(Operation of Blood Pressure Measurement by Oscillometric Method)

The blood pressure measurement by the oscillometric method in the sphygmomanometer 1 of the fourth embodiment is performed according to the operation flow shown in FIG. 6 as in the case of the first embodiment. In the fourth embodiment, the control of the press cuff 21*a*, the press cuff 21*b*, the press cuff 21*c*, the press cuff 21*d*, and the press cuff 21*i* in an initialization step of step S2 is different from that of the first embodiment. In the fourth embodiment, in the initialization step of step S2, the CPU 100 outputs control signals to the valve drive circuits 330*a*, 330*b*, 330*c*, 330*d* and 330*i* to open the valves 33*a*, 33*b*, 33*c*, 33*d* and 33*i* and exhaust the air in the press cuff 21*a*, the press cuff 21*b*, the press cuff 21*c*, the press cuff 21*d*, and the press cuff 21*i*. Thereafter, the CPU 100 outputs control signals to the valve drive circuits 330*a*, 330*b*, 330*c*, 330*d* to maintain the depressurized states of the press cuff 21*a*, the press cuff 21*b*, the press cuff 21*c*, and the press cuff 21*d* while keeping the valves 33*a*, 33*b*, 33*c* and 33*d* open. As described above, in the fourth embodiment, when the blood pressure measurement is performed by the oscillometric method, it is different from the first embodiment to maintain the depressurized states of the press cuff 21*a*, the press cuff 21*b*, the press cuff 21*c*, and the press cuff 21*d*.

The fourth embodiment is different from the first embodiment in that the control of the cuff pressure in step S3 is performed on the press cuff 21*i*. The CPU 100 closes the valve 33*i* via the valve drive circuit 330*i*, and then drives the pump 32*i* via the pump drive circuit 320*i* to perform control to feed air to the press cuff 21*i*. As a result, the press cuff 21*i* is expanded, and also the cuff pressure Pc (see FIG. 34) is gradually increased (step S3 in FIG. 6).

In this pressure-increasing step, in order to calculate the blood pressure value, the CPU 100 monitors the cuff pressure Pc with the pressure sensor 31*i*, and acquires a fluctuation component of an arterial volume occurring in the radial artery 91 of the left wrist 90 as the measurement target site as a pulse wave signal Pm as shown in FIG. 7.

Next, in step S4 in FIG. 6, the CPU 100 works as a second blood pressure calculation unit, and applies a publicly-known algorithm by oscillometric method based on a pulse wave signal Pm acquired at this time point to attempt calculation of a blood pressure value (systolic blood pressure SBP and diastolic blood pressure DBP).

At this time point, when the blood pressure value cannot be still calculated because of insufficient data (NO in step S5), the processing of steps S3 to S5 is repeated unless the cuff pressure Pc has reached the upper limit pressure (which is predetermined to, for example, 300 mmHg for safety).

When the blood pressure value can be calculated as described above (YES in step S5), the CPU 100 stops the pump 32*i* via the pump drive circuit 320*i*, and opens the valve 33*i* via the valve drive circuit 330*i*, thereby controlling to exhaust air in the press cuff 21*i* (step S6). Finally, a measurement result of the blood pressure value is displayed on the display unit 50 and recorded in the memory 51 (step S7).

Note that the calculation of the blood pressure value is not limitedly performed in the pressure-increasing step, but may be performed in the pressure-reducing step.

In the fourth embodiment, the entire area of the measurement target site in the arterial direction (width direction Y) can be compressed by the press cuff 21*i*, so that the blood pressure measurement based on the oscillometric method can be performed with high accuracy.

(Operation of Blood Pressure Measurement Based on Pulse Transit Time)

Figure 35:
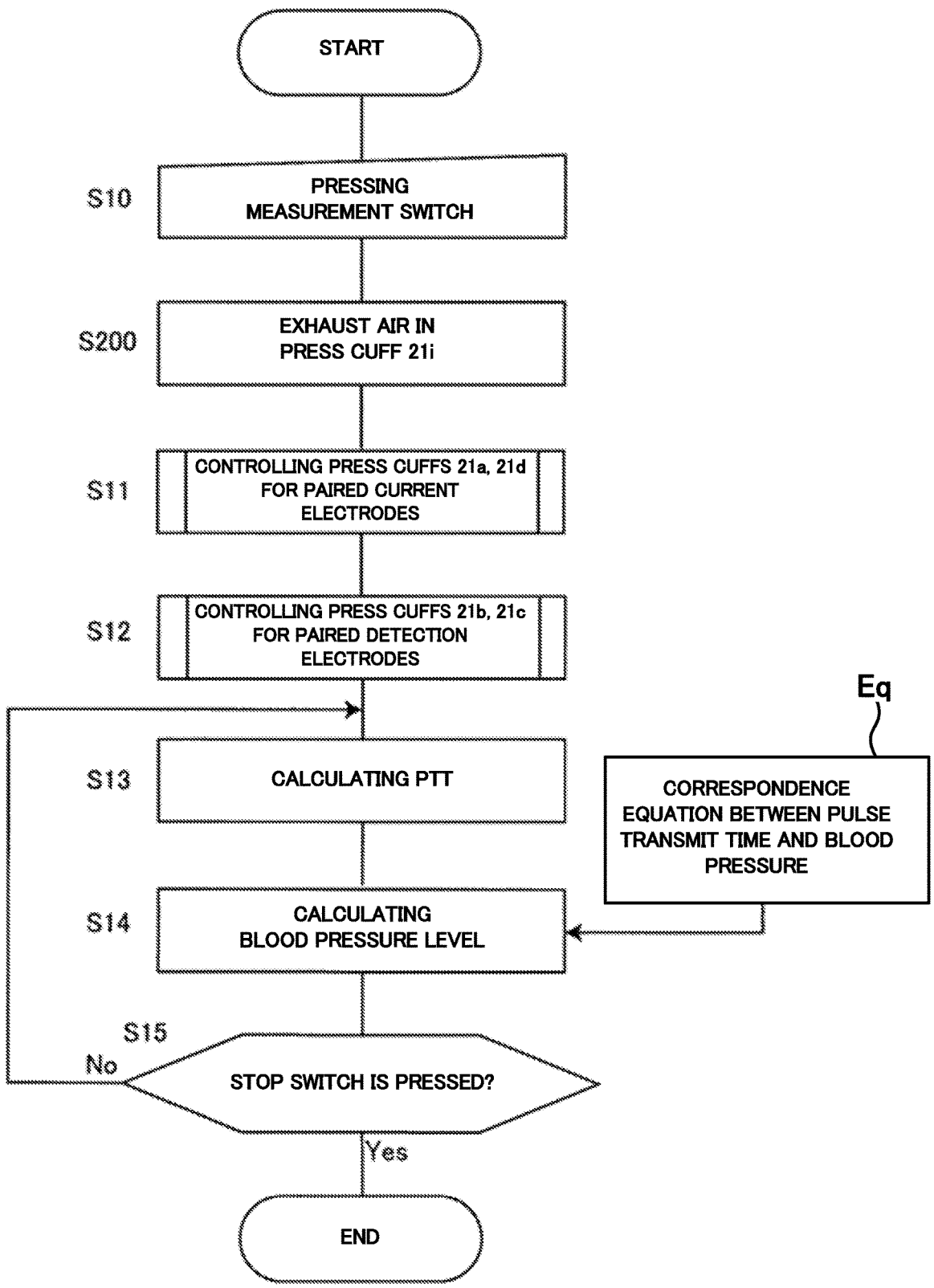
FIG. 35 is a diagram showing an operation flow when the sphygmomanometer executes the pulse wave measurement method according to an embodiment to acquire a pulse transit time (PTT) and performs blood pressure measurement (estimation) based on the pulse transit time.

FIG. 35 shows an operation flow when the sphygmomanometer 1 of the fourth embodiment performs the blood pressure measurement (estimation) based on the pulse transit time (PTT). The operation flow of the fourth embodiment shown in FIG. 35 is different from the operation flow when the blood pressure measurement (estimation) based on PTT in the first embodiment shown in FIG. 8 is performed in the exhaust control of the press cuff 21*i*. In the fourth embodiment, when the user instructs the blood pressure measurement based on PTT by the push type switch as the operation unit 52 provided in the main body 10 (step S10 in FIG. 35), the CPU 100 outputs a control signal to the valve drive circuit 330*i* to open the valve 33*i* and exhaust the air in the press cuff 21*i* (step S200 in FIG. 35). Thereafter, the CPU 100 outputs a control signal to the valve drive circuit 330*i* to maintain the depressurized state of the press cuff 21*i* while keeping the valve 33*i* open. The processing subsequent to step S11 is similar to that of the first embodiment.

That is, the CPU 100 works as the current electrode pressing force setting unit, the pulse wave sensor pressing force setting unit, the waveform comparing unit, the measurement processing unit, and the first blood pressure calculation unit, and performs the blood pressure measurement (estimation) based on PTT as in the case of the first embodiment.

Note that the determination manner as to whether the waveform of the second pulse wave signal PS2 and the waveform of the first pulse wave signal PS1 having the maximum amplitude are identical to each other described in the first modification is likewise applicable in the fourth embodiment.

According to the sphygmomanometer 1, blood pressure can be continuously measured over a long period of time with light physical burden on users by the blood pressure measurement based on the pulse transit time (PTT).

Furthermore, according to the sphygmomanometer 1, the blood pressure measurement (estimation) based on the pulse transit time and the blood pressure measurement by the oscillometric method can be performed by an integrated device. Therefore, the convenience of the users can be enhanced.

(Fourth Modification)

In the above-described embodiments, in step S50 of FIG. 12, step S90 of FIG. 22, and step S130 of FIG. 30, it is determined that the waveform of the second pulse wave signal PS2 and the waveform of the first pulse wave signal PS1 having the maximum amplitude are identical to each other with the pressing force (cuff pressure Pc) being equal to a value (the lower limit value P1 in the proper pressing range shown in FIG. 9) at the time point when the cross-correlation coefficient r between the waveforms of the first and second pulse wave signals PS1 and PS2 exceeds the threshold value Th. However, the determination is not limited to this manner. The CPU 100 may further perform control to set the pressing force (cuff pressure Pc) to a value (P3 shown in FIG. 13) at which the cross-correlation coefficient r exhibits the maximum value rmax. In the example of FIG. 13, this value is P3≅106 mmHg. As a result, the measurement accuracy of the pulse transit time can be further enhanced.

In the above-described embodiments, in order to calculate (estimate) the blood pressure based on the pulse transit time (PTT) in step S14 of FIG. 8, the equation (Eq. 2) in FIG. 37 is used as the correspondence equation Eq between the pulse transit time and the blood pressure. However, the embodiments are not limited to this manner. For example, as shown in an equation (Eq. 3) of FIG. 38, when the pulse transit time is represented by DT and the blood pressure is represented by EBP, an equation including a term of $1/DT$ and a term of DT in addition to the term of $1/DT^2$ may be used as the correspondence equation Eq between the pulse transit time and the blood pressure. In the equation (Eq. 3), $\alpha$, $\beta$, $\gamma$ and $\delta$ respectively represent known coefficients or constants.

Furthermore, for example, as shown in an equation (Eq. 4) of FIG. 39, an equation including a term of $1/DT$, a term of a cardiac cycle RR, and a term of a volume pulse wave area ratio VR may be used (for example, see Japanese Patent Laid-Open No. 2000-33078). In the equation (Eq. 4), $\alpha$, $\beta$, $\gamma$ and $\delta$ respectively represent known coefficients or constants. In this case, the CPU 100 calculates the cardiac cycle RR and the volume pulse wave area ratio VR based on the pulse wave signals PS1 and PS2.

When these equations (Eq. 3) and (Eq. 4) are used as the correspondence equation Eq between the pulse transit time and the blood pressure, the measurement accuracy of blood pressure can be enhanced as in the case of using the equation (Eq. 2). Of course, a correspondence equation other than these equations (Eq. 2), (Eq. 3) and (Eq. 4) may be used.

In the above-described embodiments, the first pulse wave sensor 40-1 and the second pulse wave sensor 40-2 detect the pulse wave of the artery (radial artery 91) passing through the measurement target site (left wrist 90) as variation of impedance (impedance method). However, these embodiments are not limited to this manner. Each of the first and second pulse wave sensors may include a light emitting element for emitting light to an artery passing through a corresponding portion of the measurement target site, and a light receiving element for receiving reflected light (or transmitted light) of the light, and detect a pulse wave of the artery as variation in volume (photoelectric method). Alternatively, each of the first and second pulse wave sensors may include a piezoelectric sensor in contact with the measurement target site, and detect a strain caused by pressure of an artery passing through a corresponding portion of the measurement target site as variation in electric resistance (piezoelectric method). Furthermore, each of the first and second pulse wave sensors may include a transmitting element for transmitting radio wave (transmitted wave) to an artery passing through a corresponding portion of the measurement target site, and a receiving element for receiving reflected wave of the radio wave, and detect variation in distance between the artery and the sensor due to an arterial pulse wave as a phase shift between the transmitted wave and the reflected wave (radio wave irradiation method).

In the above-described embodiments, it is assumed that the sphygmomanometer 1 is intended to be worn on the left wrist 90 as the measurement target site. However, the embodiments are not limited to this manner. The measurement target site may be any site through which an artery passes, and may be an upper limb such as an upper arm other than the wrist, or a lower limb such as an ankle or thigh.

In the above-described embodiments, it is assumed that the CPU 100 mounted in the sphygmomanometer 1 works as the waveform comparing unit, the pulse wave sensor pressing force setting unit, the current electrode pressing force setting unit, the measurement processing unit, and the first and second blood pressure calculation units, and performs the blood pressure measurement by the oscillometric method (the operation flow in FIG. 6) and the blood pressure measurement (estimation) based on PTT (the operation flows in FIG. 8, FIG. 19, FIG. 27, and FIG. 35). However, the embodiments are not limited to this manner. For example, a substantial computer device such as a smartphone provided outside the sphygmomanometer 1 may work as the waveform comparing unit, the pulse wave sensor pressing force setting unit, the current electrode pressing force setting unit, the measurement processing unit, and the first and second blood pressure calculation units, and cause, through a network 900, the sphygmomanometer 1 to perform the blood pressure measurement by the oscillometric method (the operation flow in FIG. 6) and the blood pressure measurement (estimation) based on PTT (the operation flows in FIG. 8, FIG. 19, FIG. 27, and FIG. 35).

As is described above, a pulse wave measurement device according to the present disclosure includes:

a belt to be worn so as to be wound around a measurement target site;

first and second pulse wave sensors that are mounted on the belt to be spaced from each other with respect to a width direction of the belt, and that detect pulse waves of opposing portions of an artery passing through the measurement target site;

a pressing unit that is mounted on the belt and is capable of changing pressing forces of the first and second pulse wave sensors against the measurement target site to press the measurement target site;

a waveform comparing unit that acquires first and second pulse wave signals which are time-sequentially output by the first and second pulse wave sensors respectively, and compares waveforms of the first and second pulse wave signals; and a pulse wave sensor pressing force setting unit that variably sets the pressing forces by the pressing unit such that the waveforms of the first and second pulse wave signals compared by the waveform comparing unit become identical to each other.

In the present specification, the "measurement target site" indicates a site through which an artery passes. The measurement target site may be, for example, an upper limb such as a wrist or an upper arm, or a lower limb such as an ankle or a thigh. Furthermore, in the present specification, "with respect to" the width direction of the belt indicates a positional relationship in the width direction of the belt.

Furthermore, "belt" indicates a belt-like member which is mounted to be wound around the measurement target site regardless of the name. For example, in place of the belt, the name such as "band" or "cuff" is possible.

The "width direction" of the belt corresponds to the longitudinal direction of the measurement target site.

In the pulse wave measurement device of the present disclosure, the first and second pulse wave sensors are mounted on the belt to be spaced from each other with respect to the width direction of the belt. Under a state where the belt is mounted to be wound around the measurement target site, the pressing unit presses the first and second pulse wave sensors against the measurement target site, for example, with a certain pressing force. Under this state, the first and second pulse wave sensors detect pulse waves of opposing portions of an artery passing through the measurement target site. The waveform comparing unit acquires first and second pulse wave signals which are time-sequentially output by the first and second pulse wave sensors respectively, and compares waveforms of the first and second pulse wave signals. Here, the pulse wave sensor pressing force setting unit variably sets pressing force by the pressing unit such that the waveforms of the first and second pulse wave signals compared by the waveform comparing unit is identical to each other. As a result, the first and second pulse wave signals can be measured under an appropriate measurement condition, and the measurement accuracy of the pulse transit time can be enhanced.

In the pulse wave measurement device according to an embodiment, the pressing unit includes first and second pressing members that are separated from each other in connection with the first and second pulse wave sensors respectively, and the pulse wave sensor pressing force setting unit variably sets the pressing forces by the first and second pressing members such that the waveforms of the first and second pulse wave signals compared by the waveform comparing unit are identical to each other.

In the pulse wave measurement device according to the embodiment, the first and second pulse wave sensors can be pressed with appropriate pressing forces by the first and second pressing members, respectively.

In the pulse wave measurement device according to the embodiment, the first and second pulse wave sensors each include paired detection electrodes for detecting voltages of the opposing portions respectively, and the pulse wave measurement device includes:

paired current electrodes that are mounted on the belt to be spaced from each other such that the first and second pulse wave sensors are sandwiched between the paired current electrodes with respect to the width direction of the belt, and that supply a current to the measurement target site;

third and fourth pressing members that are separated from each other in connection with the paired current electrodes respectively; and a current electrode pressing force setting unit that acquires first and second pulse wave signals which are time-sequentially output as voltage signals by the first and second pulse wave sensors respectively, and that variably sets pressing forces by the third and fourth pressing members such that S/N characteristics of the first and second pulse wave signals are not less than a predetermined value.

In the pulse wave measuring device according to the embodiment, the respective paired current electrodes can be pressed against the measurement target site with appropriate pressing forces by the current electrode pressing force setting unit and the third and fourth pressing members, and reliable pulse wave signals can be acquired as the first and second pulse wave signals.

In the pulse wave measurement device according to the embodiment, the pressing unit includes a solid arranged across the first and second pulse wave sensors with respect to the width direction of the belt, and fifth and sixth pressing members that press outer portions of the solid than the first and second pulse wave sensors with respect to the width direction of the belt respectively, and the pulse wave sensor pressing force setting unit variably sets pressing forces by the fifth and sixth pressing members such that the waveforms of the first and second pulse wave signals compared by the waveform comparing unit are identical to each other.

According to experiments by the present inventors, it has been found that when the pressing forces of the first and second pulse wave sensors on the measurement target site are set to different values so as to follow a certain pressure gradient, it is easy to acquire a state where the waveforms of the first and second pulse wave signals are identical to each other. Therefore, in the pulse wave measurement device according to the embodiment, the solid arranged across the first and second pulse wave sensors is pressed by the fifth and sixth pressing members which press outer portions of the solid than the first and second pulse wave sensors with respect to the width direction of the belt. The pressing forces of the fifth and sixth pressing members are variably set by the pulse wave sensor pressing force setting unit such that the waveforms of the first and second pulse wave signals compared by the waveform comparing unit are identical to each other. Accordingly, the pressing forces of the first and second pulse wave sensors are set to different values so as to follow a certain pressure gradient, which makes it easy to acquire the state where the waveforms of the first and second pulse wave signals are identical to each other. As a result, the first and second pulse wave signals can be measured under an appropriate measurement condition, and the measurement accuracy of the pulse transit time can be further enhanced.

In the pulse wave measurement device according to the embodiment, the pressing unit includes a solid arranged across the first and second pulse wave sensors with respect to the width direction of the belt, a seventh pressing member that is arranged to face the solid and is capable of generating pressing force toward the solid, an eighth pressing member interposed between the seventh pressing member and one side of the outer portions of the solid than the first and second pulse wave sensors with respect to the width direction of the belt, and a spacer interposed between the seventh pressing member and another side of the outer portions of the solid, and the pulse wave sensor pressing force setting unit variably sets pressing forces by the seventh and eighth pressing members such that the waveforms of the first and second pulse wave signals compared by the waveform comparing unit are identical to each other.

In the pulse wave measurement device according to the embodiment, the seventh pressing member is arranged to face the solid which is arranged across the first and second pulse wave sensors, and can generate pressing force toward the solid. Here, the eighth pressing member is interposed between the seventh pressing member and the one side of the outer portions of the solid than the first and second pulse wave sensors with respect to the width direction of the belt. Furthermore, a spacer is interposed between the other side of the outer portions of the solid and the seventh pressing member. The pressing forces by the seventh and eighth pressing members are variably set by the pulse wave sensor pressing force setting unit such that the waveforms of the first and second pulse wave signals compared by the waveform comparing unit are identical to each other. Therefore, the pressing forces of the first and second pulse wave sensors are set to different values so as to follow a certain pressure gradient, which makes it easy to acquire the state where the waveforms of the first and second pulse wave signals are identical to each other. As a result, the first and second pulse wave signals can be measured under an appropriate measurement condition, and the measurement accuracy of the pulse transit time can be further enhanced.

In the pulse wave measurement device according to the embodiment, the pulse wave sensor pressing force setting unit determines whether the waveforms of the first and second pulse wave signals are identical to each other based on amplitudes of the first and second pulse wave signals.

In the pulse wave measurement device of the embodiment, it is determined based on the amplitudes of the first and second pulse wave signals whether the waveforms of the first and second pulse wave signals are identical to each other. As a result, the first and second pulse wave signals can be measured under an appropriate measurement condition, and the measurement accuracy of the pulse transit time can be further enhanced.

In the pulse wave measurement device according to the embodiment, the pulse wave sensor pressing force setting unit determines whether the waveforms of the first and second pulse wave signals are identical to each other based on upstroke times of the first and second pulse wave signals.

In the pulse wave measurement device according to the embodiment, it is determined based on the upstroke times of the first and second pulse wave signals whether the waveforms of the first and second pulse wave signals are identical to each other. As a result, the first and second pulse wave signals can be measured under an appropriate measurement condition, and the measurement accuracy of the pulse transit time can be further enhanced.

In the pulse wave measurement device according to the embodiment, the pulse wave sensor pressing force setting unit determines whether the waveforms of the first and second pulse wave signals are identical to each other based on a cross-correlation coefficient between the waveforms of the first and second pulse wave signals.

In the present specification, "cross-correlation coefficient" means a sample correlation coefficient (also referred to as Pearson's product moment correlation coefficient). For example, given a data string $\{xi\}$ and a data string $\{yi\}$ consisting of two sets of numerical values (here, i=1, 2, . . . , n), the cross-correlation coefficient r between the data string $\{xi\}$ and the data string $\{yi\}$ is defined by an equation (Eq. 1) shown in FIG. 36. In the equation (Eq. 1), x and y with upper bars respectively represent average values of x and y.

In the pulse wave measurement device according to the embodiment, based on the cross-correlation coefficient between the waveforms of the first and second pulse wave signals, it is determined whether the waveforms of the first and second pulse wave signals are identical to each other. As a result, the first and second pulse wave signals can be measured under an appropriate measurement condition, and the measurement accuracy of the pulse transit time can be further enhanced.

According to another aspect, a blood pressure measurement device of the present invention includes:

the pulse wave measurement device described above;

a measurement processing unit that acquires a time difference between the first and second pulse wave signals as a pulse transit time under pressing force set by the pulse wave sensor pressing force setting unit such that the waveforms of the first and second pulse wave signals are identical to each other; and a first blood pressure calculation unit that calculates a blood pressure based on the pulse transit time acquired by the measurement processing unit by using a predetermined correspondence equation between the pulse transit time and the blood pressure.

In the blood pressure measurement device of the embodiment, the pulse transit time is acquired with high accuracy by the measurement processing unit. The first blood pressure calculation unit calculates (estimates) blood pressure based on the pulse transit time acquired by the measurement processing unit by using a predetermined correspondence equation between the pulse transit time and the blood pressure. Therefore, the measurement accuracy of blood pressure can be enhanced.

According to a further other aspect, a blood pressure measurement device of the present disclosure includes:

the pulse wave measurement device described above;

a measurement processing unit that acquires a time difference between the first and second pulse wave signals as a pulse transit time under pressing force set by the pulse wave sensor pressing force setting unit such that the waveforms of the first and second pulse wave signals are identical to each other; and a first blood pressure calculation unit that calculates a blood pressure based on the pulse transit time acquired by the measurement processing unit by using a predetermined correspondence equation between the pulse transit time and the blood pressure, wherein each of the pressing members is a fluid bag provided along the belt, and has a main body provided integrally with the belt, and in the main body, the measurement processing unit and the first blood pressure calculation unit are mounted and a pressure control unit that controls pressure by supplying air into the fluid bag and a second blood pressure calculation unit that calculates blood pressure based on the pressure in the fluid bag are mounted for blood pressure measurement by an oscillometric method.

In the present specification, the main body is "integrally provided" to the belt means that the belt and the main body may be integrally formed, or the belt and the main body may be separately formed and the main body may be integrally fitted to the belt via an engagement member (a hinge or the like, for example).

In the blood pressure measurement device of the embodiment, the blood pressure measurement (estimation) based on the pulse transit time and the blood pressure measurement by the oscillometric method can be performed by an integrated device. Therefore, the convenience of users is enhanced.

According to a further other aspect, a blood pressure measurement device of the present disclosure includes:

the pulse wave measurement device described above, wherein the pulse wave sensor pressing force setting unit is capable of setting the first pressing member, the second pressing member, the third pressing member, and the fourth pressing member to a depressurized state;

a compressing member that is interposed between the belt and the first pressing member, the second pressing member, the third pressing member, and the fourth pressing member, can be worn so as to be wound around the measurement target site, and is set to a pressurized state for compressing the measurement target site or a depressurized state for releasing compression of the measurement target site;

a measurement processing unit that sets the compressing member to a depressurized state and acquires a time difference between the first and second pulse wave signals as a pulse transit time under pressing force set by the pulse wave sensor pressing force setting unit such that the waveforms of the first and second pulse wave signals are identical to each other;

a first blood pressure calculation unit that calculates a blood pressure based on the pulse transit time acquired by the measurement processing unit by using a predetermined correspondence equation between the pulse transit time and the blood pressure; and a second blood pressure calculation unit that sets the first pressing member, the second pressing member, the third pressing member, and the fourth pressing member to a depressurized state, sets the compressing member to a pressurized state for blood pressure measurement by an oscillometric method, and calculates blood pressure based on pressure of the compressing member.

In the blood pressure measurement device of the embodiment, the blood pressure measurement (estimation) based on the pulse transit time and the blood pressure measurement by the oscillometric method can be performed by an integrated device. Therefore, the convenience of users is enhanced.

According to a further other aspect, a pulse wave measurement method of the present disclosure is a pulse wave measurement method for measuring a pulse wave by including a belt to be worn so as to be wound around a measurement target site, first and second pulse wave sensors that are mounted on the belt to be spaced from each other with respect to a width direction of the belt, and that detect pulse waves of opposing portions of an artery passing through the measurement target site, and a pressing unit that is mounted on the belt and is capable of changing pressing forces of the first and second pulse wave sensors against the measurement target site to press the measurement target site, including:

acquiring first and second pulse wave signals which are time-sequentially output by the first and second pulse wave sensors respectively to compare waveforms of the first and second pulse wave signals; and variably setting pressing force by the pressing unit such that the compared waveforms of the first and second pulse wave signals are identical to each other.

According to the pulse wave measurement method of the present invention, the first and second pulse wave signals can be measured under an appropriate measurement condition, and the measurement accuracy of the pulse transit time can be enhanced.

As is apparent from the foregoing, according to the pulse wave measurement device and the pulse wave measurement method of the present invention, the first and second pulse wave signals can be measured under an appropriate measurement condition, and the measurement accuracy of the pulse transit time can be enhanced.

Moreover, according to the blood pressure measurement device of the present invention, the measurement accuracy of blood pressure can be enhanced.

The above embodiments are illustrative, and various modifications are possible without departing from the scope of the present invention. The plural embodiments described above can be established alone, but it is possible to combine the embodiments. In addition, although various features in different embodiments can be established alone, it is possible to combine features in different embodiments.

The invention claimed is:

1. A pulse wave measurement device comprising:
a belt to be worn so as to be wound around a wrist as a measurement target site;
first and second pulse wave sensors that are mounted on the belt to be spaced from each other with respect to a width direction of the belt, and that detect pulse waves of a radial artery passing through the wrist;
a plurality of bag-shaped pressing cuffs that are mounted on the belt and are capable of changing pressing forces of the first and second pulse wave sensors against the wrist to press the wrist; and a central processing unit configured to
acquire first and second pulse wave signals which are time-sequentially output by the first and second pulse wave sensors respectively, and compare waveforms of the first and second pulse wave signals, and variably set the pressing forces by the pressing cuffs such that the waveforms of the first and second pulse wave signals compared by the central processing unit are identical to each other, wherein
the pressing cuffs include a solid arranged across the first and second pulse wave sensors with respect to the width direction of the belt, and two bag-shaped pressing cuffs, of the plurality of bag-shaped pressing cuffs, that press outer portions of the solid respectively, the outer portions being located, with respect to the width direction of the belt, closer to end portions of the solid than a portion of the solid facing the first and second pulse wave sensors, the two bag-shaped pressing cuffs being spaced from each other along the width direction of the belt, and
the central processing unit is further configured to variably set pressing forces by the two bag-shaped pressing cuffs such that the waveforms of the first and second pulse wave signals compared by the central processing unit are identical to each other.

2. The pulse wave measurement device according to claim 1, wherein
the first and second pulse wave sensors each include paired detection electrodes configured to detect voltages of the wrist respectively,
the pulse wave measurement device further comprises:
paired current electrodes that are mounted on the belt to be spaced from each other such that the first and second pulse wave sensors are sandwiched between the paired current electrodes with respect to the width direction of the belt, and that are configured to supply a current to the wrist, wherein
the two bag-shaped pressing cuffs correspond to the paired current electrodes respectively, and
the central processing unit is further configured to acquire first and second pulse wave signals which are time-sequentially output as voltage signals by the first and second pulse wave sensors respectively, and variably set pressing forces by the two bag-shaped pressing cuffs such that signal-to-noise characteristics of the first and second pulse wave signals are not less than a predetermined value.

3. A blood pressure measurement device comprising:
the pulse wave measurement device according to claim 2, wherein
the central processing unit is further configured to set the two bag-shaped pressing cuffs to a depressurized state,
the blood pressure measurement device further comprises
a bag-shaped upper pressing cuff that is interposed between the belt and the two bag-shaped pressing cuffs, is configured to be wound around the wrist, and is set to a pressurized state for compressing the wrist or a depressurized state for releasing compression of the wrist, and
the central processing unit is further configured to
set the upper pressing cuff to the depressurized state and acquire a time difference between the first and second pulse wave signals as a pulse transit time under pressing forces set by the central processing unit such that the waveforms of the first and second pulse wave signals are identical to each other,
calculate a blood pressure based on the pulse transit time acquired by the central processing unit by using a predetermined correspondence equation between the pulse transit time and the blood pressure, and
set the two bag-shaped pressing cuffs to the depressurized state, set the upper pressing cuff to the pressurized state for blood pressure measurement by an oscillometric method, and calculate the blood pressure based on pressure of the upper pressing cuff.

4. The pulse wave measurement device according to claim 1, wherein
the central processing unit is further configured to determine whether the waveforms of the first and second pulse wave signals are identical to each other based on amplitudes of the first and second pulse wave signals.

5. The pulse wave measurement device according to claim 1, wherein
the central processing unit is further configured to determine whether the waveforms of the first and second pulse wave signals are identical to each other based on upstroke times of the first and second pulse wave signals.

6. The pulse wave measurement device according to claim 1, wherein
the central processing unit is further configured to determine whether the waveforms of the first and second pulse wave signals are identical to each other based on a cross-correlation coefficient between the waveforms of the first and second pulse wave signals.

7. A blood pressure measurement device comprising:
the pulse wave measurement device according to claim 1, wherein
the central processing unit is further configured to
acquire a time difference between the first and second pulse wave signals as a pulse transit time under pressing forces set by the central processing unit such that the waveforms of the first and second pulse wave signals are identical to each other, and
calculate a blood pressure based on the pulse transit time acquired by the central processing unit by using a predetermined correspondence equation between the pulse transit time and the blood pressure.

8. The pulse wave measurement device according to claim 1, wherein
the first and second pulse wave sensors are disposed between the two bag-shaped pressing cuffs along the width direction.

9. A pulse wave measurement device comprising:
a belt to be worn so as to be wound around a wrist as a measurement target site;
first and second pulse wave sensors that are mounted on the belt to be spaced from each other with respect to a width direction of the belt, and that detect pulse waves of a radial artery passing through the wrist;
a plurality of bag-shaped pressing cuffs that are mounted on the belt and are capable of changing pressing forces of the first and second pulse wave sensors against the wrist to press the wrist; and
a central processing unit configured to
acquire first and second pulse wave signals which are time-sequentially output by the first and second pulse wave sensors respectively, and compare waveforms of the first and second pulse wave signals, and variably set the pressing forces by the pressing cuffs such that the waveforms of the first and second pulse wave signals compared by the central processing unit are identical to each other, wherein the pressing cuffs include a solid arranged across the first and second pulse wave sensors with respect to the width direction of the belt, a primary bag-shaped pressing cuff that is arranged to face the solid and is capable of generating pressing force toward the solid, a secondary bag-shaped pressing cuff interposed between the primary pressing cuff and one side of outer portions of the solid respectively, the outer portions being located, with respect to the width direction of the belt, closer to end portions of the solid than a portion of the solid facing the first and second pulse wave sensors, and a spacer interposed between the primary pressing cuff and another side of the outer portions of the solid, and the central processing unit is further configured to variably set pressing forces by the primary pressing cuff and the secondary pressing cuff such that the waveforms of the first and second pulse wave signals compared by the central processing unit are identical to each other.

10. A pulse wave measurement method for measuring a pulse wave by including a belt to be worn so as to be wound around a wrist as a measurement target site, first and second pulse wave sensors that are mounted on the belt to be spaced from each other with respect to a width direction of the belt, and that detect pulse waves of a radial artery passing through the wrist, and a plurality of bag-shaped pressing cuffs that are mounted on the belt and are capable of changing pressing forces of the first and second pulse wave sensors against the wrist to press the wrist, the method comprising:

acquiring first and second pulse wave signals which are time-sequentially output by the first and second pulse wave sensors respectively to compare waveforms of the first and second pulse wave signals; and variably setting pressing force by the pressing cuffs such that the waveforms of the first and second pulse wave signals, which are compared, are identical to each other, wherein the pressing cuffs include a solid arranged across the first and second pulse wave sensors with respect to the width direction of the belt, and two bag-shaped pressing cuffs, of the plurality of bag-shaped pressing cuffs, that press outer portions of the solid respectively, the outer portions being located, with respect to the width direction of the belt, closer to end portions of the solid than a portion of the solid facing the first and second pulse wave sensors, the two bag-shaped pressing cuffs being spaced from each other along the width direction of the belt, and the variably setting of the pressing force includes variably setting pressing forces by the two bag-shaped pressing cuffs such that the waveforms of the first and second pulse wave signals, which are compared, are identical to each other.

11. The pulse wave measurement method according to claim 10, wherein the first and second pulse wave sensors are disposed between the two bag-shaped pressing cuffs along the width direction.

* * * * *